United States Patent [19]
Askew et al.

[11] Patent Number: 6,048,861
[45] Date of Patent: Apr. 11, 2000

[54] INTEGRIN RECEPTOR ANTAGONISTS

[75] Inventors: Ben C. Askew, Lansdale; Paul J. Coleman, Wallingford; Mark E. Duggan, Schwenksville; Wasyl Halczenko; George D. Hartman, both of Lansdale; Cecilia A. Hunt, Plymouth Meeting; John H. Hutchinson, Philadelphia; Robert S. Meissner, Schwenksville; Michael A. Patane, Harleysville; Garry R. Smith, Limerick; Jiabing Wang, Lansdale, all of Pa.

[73] Assignee: Merck & Co., Inc., Rahway, N.J.

[21] Appl. No.: 09/212,082

[22] Filed: Dec. 15, 1998

Related U.S. Application Data

[60] Provisional application No. 60/069,899, Dec. 17, 1997, provisional application No. 60/083,209, Apr. 27, 1998, provisional application No. 60/092,622, Jul. 13, 1998, and provisional application No. 60/108,063, Nov. 12, 1998.

[51] Int. Cl.⁷ .................. C07D 471/04; C07D 401/06; C07D 401/12; A61K 31/44; A61K 31/435
[52] U.S. Cl. .................. 514/256; 514/300; 544/333; 546/122; 546/123
[58] Field of Search .................. 544/333; 546/122, 546/123; 514/256, 300

[56] References Cited

U.S. PATENT DOCUMENTS

| | | | |
|---|---|---|---|
| 3,843,798 | 10/1974 | Cook et al. | 424/319 |
| 5,025,025 | 6/1991 | Bhagwat et al. | 514/340 |
| 5,352,667 | 10/1994 | Lider et al. | 514/19 |
| 5,455,243 | 10/1995 | Duggan et al. | 514/218 |
| 5,668,159 | 9/1997 | Jin et al. | 514/363 |

FOREIGN PATENT DOCUMENTS

| | | |
|---|---|---|
| 0796 855 A1 | 9/1997 | European Pat. Off. . |
| WO 95/32710 | 12/1995 | WIPO . |
| WO97/26250 | 7/1997 | WIPO . |
| WO 97/37655 | 10/1997 | WIPO . |
| WO 98/08840 | 3/1998 | WIPO . |
| WO 98/18460 | 5/1998 | WIPO . |
| WO 98/18461 | 5/1998 | WIPO . |
| WO 98/31359 | 7/1998 | WIPO . |

*Primary Examiner*—Mukund J. Shah
*Assistant Examiner*—Deepak R. Rao
*Attorney, Agent, or Firm*—Philippe L. Durette; Melvin Winokur; Anthony Sabatelli

[57] ABSTRACT

The present invention relates to compounds and derivatives thereof, their synthesis, and their use as integrin receptor antagonists. More particularly, the compounds of the present invention are antagonists of the integrin receptors $\alpha v\beta 3$, $\alpha v\beta 5$, and/or $\alpha v\beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

47 Claims, No Drawings

INTEGRIN RECEPTOR ANTAGONISTS

CROSS-REFERENCE TO RELATED APPLICATIONS

The present invention is related to U.S. provisional applications Ser. Nos. 60/069,899, filed Dec. 17, 1997; 60/083,209, filed Apr. 27, 1998; 60/092,622, filed Jul. 13, 1998; and 60/108,063, filed Nov. 12, 1998; the contents of all of which are hereby incorporated by reference.

FIELD OF THE INVENTION

The present invention relates to compounds and derivatives thereof, their synthesis, and their use as integrin receptor antagonists. More particularly, the compounds of the present invention are antagonists of the integrin receptors $\alpha v\beta 3$, $\alpha v\beta 5$, and/or $\alpha v\beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts", *Journal of Endocrinology*, Vol. 154, S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely. the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin in osteoclasts, e.g., in rat, chicken, mouse and human osteoclasts, is an integrin receptor known as $\alpha v\beta 3$, which is thought to interact in bone with matrix proteins that contain the RGD sequence. Antibodies to $\alpha v\beta 3$ block bone resorption in vitro indicating that this integrin plays a key role in the resorptive process. There is increasing evidence to suggest that $\alpha v\beta 3$ ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v\beta 3$ ligands have been found to be useful in treating and/or inhibiting restenosis, i.e. recurrence of stenosis after corrective surgery on the heart valve, atherosclerosis, diabetic retinopathy, macular degeneration, and angiogenesis, i.e. formation of new blood vessels, and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, $\alpha v\beta 3$ antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Moreover, compounds of this invention can also inhibit neovascularization by acting as antagonists of the integrin receptor, $\alpha v\beta 5$. A monoclonal antibody for $\alpha v\beta 5$ has been shown to inhibit VEGF-induced angiogenesis in rabbit cornea and the chick chorioallantoic membrane model (See M. C. Friedlander, et.al., *Science* 270:1500–1502 (1995), which is incorporated by reference herein in its entirety). Thus, compounds that antagonize $\alpha v\beta 5$ are useful for treating and preventing macular degeneration, diabetic retinopathy, tumor growth, and metastasis.

Additionally, compounds of the instant invention can inhibit angiogenesis and inflammation by acting as antagonists of the integrin receptor, $\alpha v\beta 6$, which is expressed during the later stages of wound healing and remains expressed until the wound is closed (See Christofidou-Solomidou, et al., "Expression and Function of Endothelial Cell $\alpha v$ Integrin Receptors in Wound-Induced Human Angiogenesis in Human Skin/SCID Mice Chimeras, *American Journal of Pathology*, Vol. 151, No. 4, pp. 975–983 (October 1997), which is incorporated by reference herein in its entirety). It is postulated that $\alpha v\beta 6$ plays a role in the remodeling of the vasculature during the later stages of angiogenesis. Also, $\alpha v\beta 6$ participates in the modulation of epithelial inflammation and is induced in response to local injury or inflammation (See Xiao-Zhu Huang, et al., "Inactivation of the Integrin $\beta 6$ Subunit Gene Reveals a Role of Epithelial Integrins in Regulating Inflammation in the Lungs and Skin," *Journal of Cell Biology* Vol. 133, No.4, pp. 921–928 (May 1996), which is incorporated by reference herein in its entirety). Accordingly, compounds that antagonize αvβ6 are useful in treating or preventing cancer by inhibiting tumor growth and metastasis.

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammation, viral disease, tumor growth, and metastasis.

In addition, certain compounds of this invention are useful as mixed αvβ3, and αvβ5, and αvβ6 receptor antagonists.

It is therefore an object of the present invention to provide compounds which are useful as integrin receptor antagonists.

It is another object of the present invention to provide compounds which are useful as αvβ3 receptor antagonists.

It is another object of the present invention to provide compounds which are useful as αvβ5 receptor antagonists.

It is another object of the present invention to provide compounds which are useful as αvβ6 receptor antagonists.

It is another object of the present invention to provide compounds which are useful as dual αvβ3/αvβ5 receptor antagonists.

It is another object of the present invention to provide compounds which are useful as mixed αvβ3, αvβ5, and αvβ6 receptor antagonists.

It is another object of the present invention to provide pharmaceutical compositions comprising integrin receptor antagonists.

It is another object of the present invention to provide methods for maling the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammation, viral disease, diabetic retinopathy, macular degeneration, angiogenesis, tumor growth, and metastasis.

It is another object of the present invention to provide compounds and pharmaceutical compositions useful for treating osteoporosis.

It is another object of the present invention to provide methods for inhibiting bone resorption, restenosis, atherosclerosis, inflammation, viral disease, diabetic retinopathy, macular degeneration, angiogenesis, tumor growth, and metastasis.

It is another object of the present invention to provide methods for treating osteoporosis.

These and other objects will become readily apparent from the detailed description which follows.

SUMMARY OF THE INVENTION

The present invention relates to compounds of the formula

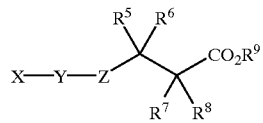

wherein X is selected from the group consisting of

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one $R^1$ substituent and the ring carbon atoms are unsubstituted or substituted with one or two $R^1$ substituents;

Y is selected from the group consisting of

—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—(CH2)m—O—(CH2)n—O—(CH2)p—,
—(CH2)m—O—(CH2)n—$NR^4$—(CH2)p—,
—(CH2)m—$NR^4$—(CH2)n—$NR^4$—(CH2)p—,
—(CH2)m—O—(CH2)n—S—(CH2)p—,
—(CH2)m—S—(CH2)n—S—(CH2)p—,
—(CH2)m—$NR^4$—(CH2)n—S—(CH2)p—,
—(CH2)m—$NR^4$—(CH2)n—O—(CH2)p—,
—(CH2)m—S—(CH2)n—O—(CH2)p—, and
—(CH2)m—S—(CH2)n—$NR^4$—(CH2)p—, wherein any methylene ($CH_2$) carbon atom in Y, other than in $R^4$, can be substituted by one or two $R^3$ substituents;

Z is selected from the group consisting of

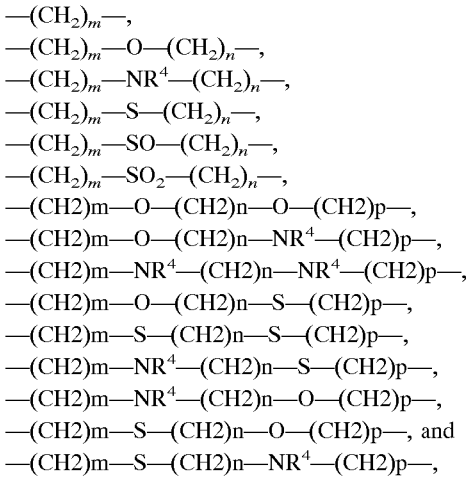

—$CH_2CH_2$— and —CH=CH—, wherein either carbon atom can be substituted by one or two $R^3$ substituents;

$R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_p$, $(C_{1-8}$ alkyl$)_p$ aminocarbonyl, $C_{1-8}$ alkyloxycarbonylamino, $(C_{1-8}$ alkyl$)_p$aminocarbonyloxy, (aryl $C_{1-8}$ alkyl$)_p$amino, (aryl$)_p$amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen, aryl, $C_{1-10}$ alkyl, aryl—$(CH_2)_r$—O—$(CH_2)_s$—, aryl—$(CH_2)_r S(O)_p$—$(CH_2)_s$—, aryl—$(CH_2)_r$—C(O)—$(CH_2)_s$—, aryl—$(CH_2)_r$—C(O)—N($R^4$)—$(CH_2)_s$—, aryl—$(CH_2)_r$—N($R^4$)—C(O)—$(CH_2)_s$—, aryl—$(CH_2)_r$N($R^4$)—$(CH_2)_s$—, halogen, hydroxyl, oxo, trifluoromethyl, $C_{1-8}$ alkylcarbonylamino, aryl $C_{1-5}$ alkoxy, $C_{1-5}$ alkoxycarbonyl, $(C_{1-8}$ alkyl$)_p$aminocarbonyl, $C_{1-6}$ alkylcarbonyloxy, $C_{3-8}$ cycloalkyl, $(C_{1-6}$ alkyl$)_p$amino, amino $C_{1-6}$ alkyl, arylaminocarbonyl, aryl $C_{1-5}$ alkylaminocarbonyl, aminocarbonyl, aminocarbonyl $C_{1-6}$ alkyl, hydroxycarbonyl, hydroxycarbonyl $C_{1-6}$ alkyl, HC≡C—$(CH_2)_t$—, $C_{1-6}$ alkyl—C≡C—$(CH_2)_t$—, $C_{3-7}$ cycloalkyl—C≡C—$(CH_2)_t$—, aryl—C≡C—$(CH_2)_t$—, $C_{1-6}$ alkylaryl—C≡C—$(CH_2)_t$—, $CH_2$=CH—$(CH_2)_t$—, $C_{1-6}$ alkyl—CH=CH—$(CH_2)_t$—, $C_{3-7}$ cycloalkyl—CH=CH—$(CH_2)_t$—, aryl—CH=CH—$(CH_2)_t$—, $C_{1-6}$ alkylaryl—CH=CH—$(CH_2)_t$—, $C_{1-6}$ alkyl—$SO_2$—$(CH_2)_t$—, $C_{1-6}$ alkylaryl—$SO_2$—$(CH_2)_t$—, $C_{1-6}$ alkoxy, aryl $C_{1-6}$ alkoxy, aryl $C_{1-6}$ alkyl, $(C_{1-6}$ alkyl$)_p$amino $C_{1-6}$ alkyl, (aryl$)_p$amino, (aryl$)_p$amino $C_{1-6}$ alkyl, (aryl $C_{1-6}$ alkyl$)_p$amino, (aryl $C_{1-6}$ alkyl$)_p$amino $C_{1-6}$ alkyl, arylcarbonyloxy, aryl $C_{1-6}$ alkylcarbonyloxy, $(C_{1-6}$ alkyl$)_p$aminocarbonyloxy, $C_{1-8}$ alkylsulfonylamino, arylsulfonylamino, $C_{1-8}$ alkylsulfonylamino $C_{1-6}$ alkyl, arylsulfonylamino $C_{1-6}$ alkyl, aryl $C_{1-6}$ alkylsulfonylamino, aryl $C_{1-6}$ alkylsulfonylamino $C_{1-6}$ alkyl, $C_{1-8}$ alkoxycarbonylamino, $C_{1-8}$ alkoxycarbonylamino $C_{1-8}$ alkyl, aryloxycarbonylamino $C_{1-8}$ alkyl, aryl $C_{1-8}$ alkoxycarbonylamino, aryl $C_{1-8}$ alkoxycarbonylamino $C_{1-8}$ alkyl, $C_{1-8}$ alkylcarbonylamino, $C_{1-8}$ alkylcarbonylamino $C_{1-6}$ alkyl, arylcarbonylamino $C_{1-6}$ alkyl, aryl $C_{1-6}$ alkylcarbonylamino, aryl $C_{1-6}$ alkylcarbonylamino $C_{1-6}$ alkyl, aminocarbonylamino $C_{1-6}$ alkyl, $(C_{1-8}$ alkyl$)_p$aminocarbonylamino, $(C_{1-8}$ alkyl$)_p$aminocarbonylamino $C_{1-6}$ alkyl, (aryl$)_p$aminocarbonylamino $C_{1-6}$ alkyl, (aryl $C_{1-8}$ alkyl$)_p$aminocarbonylamino, (aryl $C_{1-8}$ alkyl$)_p$aminocarbonylamino $C_{1-6}$ alkyl, aminosulfonylamino $C_{1-6}$ alkyl, $(C_{1-8}$ alkyl$)_p$aminosulfonylamino, $(C_{1-8}$ alkyl$)_p$aminosulfonylamino $C_{1-6}$ alkyl, (aryl$)_p$aminosulfonylamino $C_{1-6}$ alkyl, (aryl $C_{1-8}$ alkyl$)_p$aminosulfonylamino, (aryl $C_{1-8}$ alkyl$)_p$aminosulfonylamino $C_{1-6}$ alkyl, $C_{1-6}$ alkylsulfonyl, $C_{1-6}$ alkylsulfonyl $C_{1-6}$ alkyl, arylsulfonyl $C_{1-6}$ alkyl, aryl $C_{1-6}$ alkylsulfonyl, aryl $C_{1-6}$ alkylsulfonyl $C_{1-6}$ alkyl, $C_{1-6}$ alkylcarbonyl, $C_{1-6}$ alkylcarbonyl $C_{1-6}$ alkyl, arylcarbonyl $C_{1-6}$ alkyl, aryl $C_{1-6}$ alkylcarbonyl, aryl $C_{1-6}$ alkylcarbonyl $C_{1-6}$ alkyl, $C_{1-6}$ alkylthiocarbonylamino, $C_{1-6}$ alkylthiocarbonylamino $C_{1-6}$ alkyl, arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl)paminocarbonyl, and
(aryl $C_{1-8}$ alkyl$)_p$aminocarbonyl $C_{1-6}$ alkyl;
or two $R^3$ substituents, when on the same carbon atom are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
each $R^4$ is independently selected from the group consisting of
hydrogen,
aryl,
aminocarbonyl,
$C_{3-8}$ cycloalkyl,
amino $C_{1-6}$ alkyl,
(aryl$)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;
$R^5$ and $R^6$ are each independently selected from the group consisting of
hydrogen,
$C_{1-10}$ alkyl,
aryl,
aryl—$(CH_2)_r$—O—$(CH_2)_s$—,
aryl—$(CH_2)_r$S(O)$_p$—$(CH_2)_s$—,
aryl—$(CH_2)_r$—C(O)—$(CH_2)_s$—,
aryl—$(CH_2)_r$—C(O)—N(R$^4$)—$(CH_2)_s$—,
aryl—$(CH_2)_r$N(R$^4$)—C(O)—$(CH_2)_s$—,
aryl—$(CH_2)_r$—N(R$^4$)—$(CH_2)_s$—, halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—SO$_2$—$(CH_2)_t$—,
$C_{1-6}$ alkylaryl—SO$_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonlamino,
$C_{1-8}$ alkylsulfonylanmino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl, aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$amiinosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ aikyl)$_p$aminocarbonyl, and
(aryl $C_{1-8}$ alkyl)$_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen,
$C_{1-10}$ alkyl,
aryl,
aryl—$(CH_2)_r$—O—$(CH_2)_s$—,
aryl—$(CH_2)_r$—S(O)$_p$—$(CH_2)_s$—,
aryl—$(CH_2)_r$—C(O)—$(CH_2)_s$—,
aryl—$(CH_2)_r$—C(O)—N($R^4$)—$(CH_2)_s$—,
aryl—$(CH_2)_r$—N($R^4$)—C(O)—$(CH_2)_s$—,
aryl—$(CH_2)_r$N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—
aryl—C≡C—$(CH_2)_t$—
$C_{1-6}$ alkylaryl—C≡C—$(CH_2)_t$—
$CH_2$=CH—$(CH_2)_t$—
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl-$SO_2$—$(CH_2)_t$—
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino, ($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl,
(aryl $C_{1-8}$ alkyl)$_p$aminocarbonyl $C_{1-6}$ alkyl, and
$C_{7-20}$ polycyclyl $C_0$ alkylsulfonylamino,
wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and $R^8$ are attached is itself attached to no more than one heteroatom;

$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
wherein
each m is independently an integer from 0 to 6;
each n is independently an integer from 0 to 6;
each p is independently an integer from 0 to 2;
each r is independently an integer from 1 to 3;
each s is independently an integer from 0 to 3; and
each t is independently an integer from 0 to 3;
and the pharmaceutically acceptable salts thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an integrin receptor antagonizing effect in a mammal in need thereof by administering the compounds and pharmaceutical compositions of the present invention.

The present invention also relates to methods for inhibiting bone resorption, restenosis, atherosclerosis, inflammation, viral disease, diabetic retinopathy, macular degeneration, angiogenesis, wound healing, tumor growth, and metastasis by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to compounds useful as integrin receptor antagonists. Representative compounds of the present invention are described by the following structural formula:

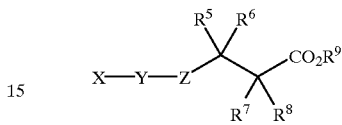

wherein X is selected from the group consisting of

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one $R^1$ substituent and the ring carbon atoms are unsubstituted or substituted with one or two $R^1$ substituents;

Y is selected from the group consisting of
—(CH$_2$)$_m$—,
—(CH$_2$)$_m$—O—(CH$_2$)$_n$—,
—(CH$_2$)$_m$—NR$^4$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH2)m—O—(CH2)n—O—(CH2)p—,
—(CH2)m—O—(CH2)n—NR$^4$—(CH2)p—,
—(CH2)m—NR$^4$—(CH2)n—NR$^4$—(CH2 )p—,
—(CH2)m—O—(CH2)n—S—(CH2)p—,
—(CH2)m—S—(CH2)n—S—(CH2)p—,
—(CH2)m—NR$^4$—(CH2)n—S—(CH2)p—,
—(CH2)m—NR$^4$—(CH2)n—O—(CH2)p—,
—CH2)m—S—(CH2)n—O—(CH2)p—, and
—(CH2)m—S—(CH2)n—NR$^4$—(CH2)p—,
wherein any methylene (CH$_2$) carbon atom in Y, other than in $R^4$, can be substituted by one or two $R^3$ substituents;

Z is selected from the group consisting of

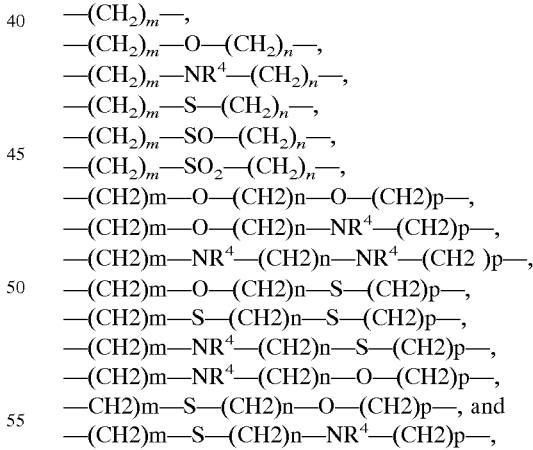

—CH$_2$CH$_2$—, and —CH=CH—, wherein either carbon atom can be substituted by one or two $R^3$ substituents;

$R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl—S(O)$_p$, $(C_{1-8}$ alkyl)$_p$aminocarbonyl, $C_{1-8}$ alkyloxycarbonylamino, $(C_{1-8}$ alkyl)$_p$aminocarbonyloxy, (aryl $C_{1-8}$ alkyl)$_p$amino, (aryl)$_p$amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen, aryl, $C_{1-10}$ alkyl, aryl—(CH$_2$)$_r$—O—(CH$_2$)$_s$—, aryl—(CH$_2$)$_r$S(O)$_p$—(CH$_2$)$_s$—, aryl—(CH$_2$)$_r$—C(O)—(CH$_2$)$_s$—, aryl—(CH$_2$)$_r$—C(O)—N(R$^4$)—(CH$_2$)$_s$—, aryl—(CH$_2$)$_r$—N(R$^4$)—C(O)—(CH$_2$)$_s$—, aryl—(CH$_2$)$_r$—N(R$^4$)—(CH$_2$)$_s$—, halogen, hydroxyl, oxo, trifluoromethyl, $C_{1-8}$ alkylcarbonylamino, aryl $C_{1-5}$ alkoxy, $C_{1-5}$ alkoxycarbonyl, $(C_{1-8}$ alkyl)$_p$aminocarbonyl, $C_{1-6}$ alkylcarbonyloxy, $C_{3-8}$ cycloalkyl, $(C_{1-6}$ alkyl)$_p$amino, amino $C_{1-6}$ alkyl, arylaminocarbonyl, aryl $C_{1-5}$ alkylaminocarbonyl, aminocarbonyl, aminocarbonyl $C_{1-6}$ alkyl, hydroxycarbonyl, hydroxycarbonyl $C_{1-6}$ alkyl, HC≡C—(CH$_2$)$_t$—, $C_{1-6}$ alkyl—C≡C—(CH$_2$)$_t$—

$C_{3-7}$ cycloalkyl—C≡C—(CH$_2$)$_t$— aryl—C≡C—(CH$_2$)$_t$—

$C_{1-6}$ alkylaryl—C≡C—(CH$_2$)$_t$—,

CH$_2$=CH—(CH$_2$)$_t$—, $C_{1-6}$ alkyl—CH=CH—(CH$_2$)$_t$—, $C_{-7}$ cycloalkyl—CH=CH—(CH$_2$)$_t$—, aryl—CH=CH—(CH$_2$)$_t$—, $C_{1-6}$ alkylaryl—CH=CH—(CH$_2$)$_t$—, $C_{1-6}$ alkyl—SO$_2$—(CH$_2$)$_t$—

$C_{1-6}$ alkylaryl—SO$_2$—(CH$_2$)$_t$—, $C_{1-6}$ alkoxy, aryl $C_{1-6}$ alkoxy, aryl $C_{1-6}$ alkyl, $(C_{1-6}$ alkyl)$_p$amino $C_{1-6}$ alkyl, (aryl)$_p$amino, (aryl)$_p$amino $C_{1-6}$ alkyl, (aryl $C_{1-6}$ alkyl)$_p$amino, (aryl $C_{1-6}$ alkyl)$_p$amino $C_{1-6}$ alkyl, arylcarbonyloxy, aryl $C_{1-6}$ alkylcarbonyloxy, $(C_{1-6}$ alkyl)$_p$aminocarbonyloxy, $C_{1-8}$ alkylsulfonylamino, arylsulfonylamino, $C_{1-8}$ alkylsulfonylamino $C_{1-6}$ alkyl, arylsulfonylamino $C_{1-6}$ alkyl, aryl $C_{1-6}$ alkylsulfonylamino, aryl $C_{1-6}$ alkylsulfonylamino $C_{1-6}$ alkyl, $C_{1-8}$ alkoxycarbonylamino, $C_{1-8}$ alkoxycarbonylamino $C_{1-8}$ alkyl, aryloxycarbonylamino $C_{1-8}$ alkyl, aryl $C_{1-8}$ alkoxycarbonylamino, aryl $C_{1-8}$ alkoxycarbonylamino $C_{1-8}$ alkyl, $C_{1-8}$ alkylcarbonylamino, $C_{1-8}$ alkylcarbonylamino $C_{1-6}$ alkyl, arylcarbonylamino $C_{1-6}$ alkyl, aryl $C_{1-6}$ alkylcarbonylamino, aryl $C_{1-6}$ alkylcarbonylamino $C_{1-6}$ alkyl, aminocarbonylamino $C_{1-6}$ alkyl, $(C_{1-8}$ alkyl)$_p$aminocarbonylamino, $(C_{1-8}$ alkyl)$_p$aminocarbonylamino $C_{1-6}$ alkyl, (aryl)$_p$aminocarbonylamino $C_{1-6}$ alkyl, (aryl $C_{1-8}$ alkyl)$_p$aminocarbonylamino, (aryl $C_{1-8}$ alkyl)$_p$aminocarbonylamino $C_{1-6}$ alkyl, aminosulfonylamino $C_{1-6}$ alkyl, $(C_{1-8}$ alkyl)$_p$aminosulfonylamino, $(C_{1-8}$ alkyl)$_p$aminosulfonylamino $C_{1-6}$ alkyl, (aryl)$_p$aminosulfonylamino $C_{1-6}$ alkyl, (aryl $C_{1-8}$ alkyl)$_p$aminosulfonylamino, (aryl $C_{1-8}$ alkyl)$_p$aminosulfonylamino $C_{1-6}$ alkyl, $C_{1-6}$ alkylsulfonyl, $C_{1-6}$ alkylsulfonyl $C_{1-6}$ alkyl, arylsulfonyl $C_{1-6}$ alkyl, aryl $C_{1-6}$ alkylsulfonyl, aryl $C_{1-6}$ alkylsulfonyl $C_{1-6}$ alkyl, $C_{1-6}$ alkylcarbonyl, $C_{1-6}$ alkylcarbonyl $C_{1-6}$ alkyl, arylcarbonyl $C_{1-6}$ alkyl, aryl $C_{1-6}$ alkylcarbonyl, aryl $C_{1-6}$ alkylcarbonyl $C_{1-6}$ alkyl, $C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one. heteroatom;

each $R^4$ is independently selected from the group consisting of
hydrogen,
aryl,
aminocarbonyl,
$C_{3-8}$ cycloalkyl,
amino $C_{1-6}$ alkyl,
(aryl)$_p$aminocarbonyl,
(aryl $C_{1-5}$ alkyl)$_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfonyl,
arylsulfonyl,
aryl $C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;

$R^5$ and $R^6$ are each independently selected from the group consisting of
hydrogen,
$C_{1-10}$ alkyl,
aryl,
aryl—$(CH_2)_r$—O—$(CH_2)_s$—,
aryl—$(CH_2)_r$S(O)$_p$—$(CH_2)_s$—,
aryl—$(CH_2)_r$—C(O)—$(CH_2)_s$—,
aryl—$(CH_2)_r$C(O)—N($R^4$)—$(CH_2)_s$—,
aryl—$(CH_2)_r$N($R^4$)—C(O)—$(CH_2)_s$—,
aryl—$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl, aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alky)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;

$R^7$ and $R^8$ are each independently selected from the group consisting of
hydrogen,
$C_{1-10}$ alkyl,
aryl,
aryl—$(CH_2)_r$—O—$(CH_2)_s$—,
aryl—$(CH_2)_r$S(O)$_p$—$(CH_2)_s$—,
aryl—$(CH_2)_r$—C(O)—$(CH_2)_s$—,
aryl—$(CH_2)_r$C(O)—N($R^4$)—$(CH_2)_s$—,
aryl—$(CH_2)_r$—N($R^4$)—C(O)—$(CH_2)_s$—,
aryl—$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl, aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl,
(aryl C$_{1-8}$ alkyl)$_p$aminocarbonyl C$_{1-6}$ alkyl, and
C$_{7-20}$ polycyclyl C$_{0-8}$ alkylsulfonylamino,
wherein any of the alkyl groups of R$^7$ and R$^8$ are either unsubstituted or substituted with one to three R$^1$ substituents, and provided that each R$^7$ and R$^8$ are selected such that in the resultant compound the carbon atom to which R$^7$ and R$^8$ are attached is itself attached to no more than one heteroatom;

R$^9$ is selected from the group consisting of
hydrogen,
C$_{1-8}$ alkyl,
aryl,
aryl C$_{1-8}$ alkyl,
C$_{1-8}$ alkylcarbonyloxy C$_{1-4}$ alkyl,
aryl C$_{1-8}$ alkylcarbonyloxy C$_{1-4}$ alkyl,
C$_{1-8}$ alkylaminocarbonylmethylene, and
C$_{1-8}$ dialkylaminocarbonylmethylene;
wherein
each m is independently an integer from 0 to 6;
each n is independently an integer from 0 to 6;
each p is independently an integer from 0 to 2;
each r is independently an integer from 1 to 3;
each s is independently an integer from 0 to 3; and
each t is independently an integer from 0 to 3;
and the pharmaceutically acceptable salts thereof In the compounds of the present invention, X is preferably a 6-membered monocyclic aromatic or nonaromatic ring system having 1 or 2 nitrogen atoms wherein each carbon atom is either unsubstituted or substituted with one R$^1$ substituent, or
a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one R$^1$ substituent and the ring carbon atoms are unsubstituted or substituted with one or two R$^1$ substituents.

More preferably X is selected from the group consisting of

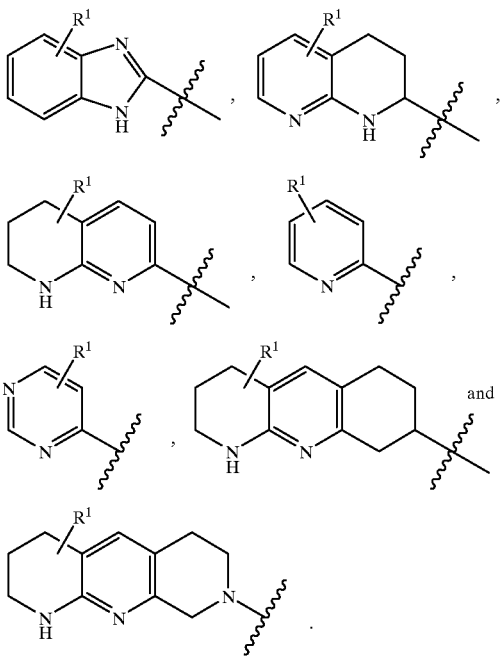

Most preferably X is

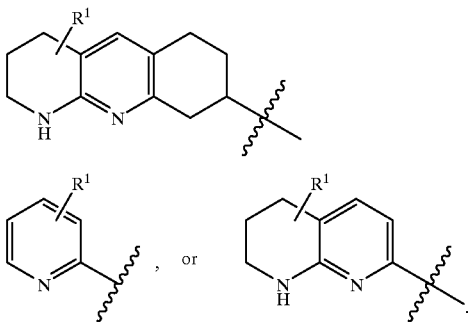

In the compounds of the present invention, Y is preferably selected from the group consisting of
—(CH$_2$)$_m$—,
—(CH$_2$)$_m$—O—(CH$_2$)$_n$—,
—(CH$_2$)$_m$—NR$^4$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH$_2$)$_m$—O—(CH2)n—O—(CH2)p—,
—(CH2)m—O—(CH2)n—NR$^4$—(CH2)p—,
—(CH2)m—NR$^4$—(CH2)n—NR$^4$—(CH2)p—, and
—(CH2)m—NR$^4$—(CH2)n—O—(CH2)p—,
wherein any methylene (CH$_2$) carbon atom in Y, other than in R$^4$, can be substituted by one or two R$^3$ substituents. More preferably, Y is selected from the group consisting of
(CH$_2$)$_m$, (CH$_2$)$_m$—S—(CH$_2$)$_n$, and (CH$_2$)$_m$—NR$^4$—(CH$_2$)$_n$,
wherein any methylene (CH$_2$) carbon atom in Y, other than in R$^4$, can be substituted by one or two R$^3$ substituents.

In the compounds of the present invention, Z is preferably selected from the group consisting of

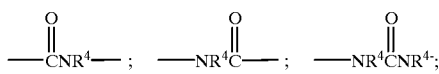

—CH$_2$CH$_2$—, and —CH=CH—, wherein either carbon atom can be substituted by one or two R$^3$ substituents.

More preferably, Z is selected from the group consisting of

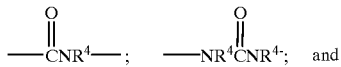 and

—CH$_2$CH$_2$—, wherein either carbon atom can be substituted by one or two R$^3$ substituents.

In the compounds of the present invention, R$^1$ and R$^2$ are preferably selected from the group consisting of hydrogen, halogen, C$_{1-10}$ alkyl, C$_{3-8}$ cycloalkyl, C$_{3-8}$ cycloheteroalkyl, hydroxy, nitro, cyano, trifluoromethyl, and trifluoromethoxy.

More preferably, R$^1$ and R$^2$ are selected from the group consisting of hydrogen, halogen, C$_{1-10}$ alkyl, C$_{3-8}$ cycloalkyl, trifluoromethyl, and trifluoromethoxy.

In the compounds of the present invention, R$^3$ is preferably selected from the group consisting of
hydrogen,
fluoro,
trifluoromethyl,
aryl,
C$_{1-8}$ alkyl,
arylC$_{1-6}$ alkyl
hydroxyl,
oxo,
arylaminocarbonyl,
aryl C$_{1-5}$ alkylaminocarbonyl,
aminocarbonyl, and
aminocarbonyl C$_{1-6}$ alkyl.

More preferably, R$^3$ is selected from the group consisting of
fluoro,
aryl,
C$_{1-8}$ alkyl,
arylC$_{1-6}$ alkyl
hydroxyl,
oxo, and
arylaminocarbonyl.

In the compounds of the present invention, R$^4$ is preferably selected from the group consisting of
hydrogen,
aryl,
C$_{3-8}$ cycloalkyl,
C$_{1-8}$ alkyl,
C$_{1-8}$ alkylcarbonyl,
arylcarbonyl,
C$_{1-6}$ alkylsulfonyl,
arylsulfonyl,
arylC$_{1-6}$alkylsulfonyl,
arylC$_{1-6}$alkylcarbonyl,
C$_{1-8}$alkylaminocarbonyl,
arylC$_{1-5}$alkylaminocarbonyl,
arylC$_{1-8}$alkoxycarbonyl, and
C$_{1-8}$alkoxycarbonyl.

More preferably, R$^4$ is selected from the group consisting of
hydrogen,
C$_{1-8}$ alkyl,
C$_{1-8}$ alkylcarbonyl,
arylcarbonyl,
aryl C$_{1-6}$alkylcarbonyl,
C$_{1-6}$ alkylsulfonyl,
arylsulfonyl, and
arylC$_{1-6}$alkylsulfonyl.

In one embodiment of the present invention, R$^5$ and R$^6$ are each independently selected from the group consisting of
hydrogen,
aryl,
C$_{1-8}$ alkyl,
aryl—C≡C—(CH$_2$)$_t$—,
aryl C$_{1-6}$ alkyl,
CH$_2$=CH—(CH$_2$)$_t$—, and
HC≡C—(CH$_2$)$_t$—.

In a class of this embodiment of the present invention, R$^6$ is hydrogen and R$^5$ is selected from the group consisting of
hydrogen,
aryl,
C$_{1-8}$ alkyl,
aryl—C≡C—(CH$_2$)$_t$—,
aryl C$_{1-6}$ alkyl,
CH$_2$=CH—(CH$_2$)$_t$—, and
HC≡C—(CH$_2$)$_t$—.

In a subclass of this class of the present invention, R$^6$, R$^7$ and R$^8$ are each hydrogen and R$^5$ is selected from the group consisting of
hydrogen,
aryl,
C$_{1-8}$ alkyl,
aryl—C≡C—(CH$_2$)$_t$—,
aryl C$_{1-6}$ alkyl,
CH$_2$=CH—(CH$_2$)$_t$—, and
HC≡C—(CH$_2$)$_t$—.

In another embodiment of the present invention, R$^7$ and R$^8$ are each independently selected from the group consisting of
hydrogen,
aryl,
C$_{1-8}$ alkylcarbonylamino,
C$_{1-8}$ alkylsulfonylamino,
arylcarbonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino, aryl $C_{1-8}$ alkoxycarbonylanmino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
arylaminocarbonylamino,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl, and
$C_{7-20}$ polycyclyl $C_{0-8}$ alkylsulfonylamino.

In a class of this embodiment of the present invention, $R^8$ is hydrogen and $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl)$_p$aminocarbonylamino,
$(C_{1-8}$ alkyl$)_p$aminosulfonylamino, and
(aryl $C_{1-8}$ alkyl)$_p$aminosulfonylamino.

In a subclass of this class of the present invention, $R^5$, $R^6$ and $R^8$ are each hydrogen and $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl)$_p$aminocarbonylamino,
$(C_{1-8}$ alkyl$)_p$aminosulfonylamino, and
(aryl $C_{1-8}$ alkyl)$_p$aminosulfonylamino.

In the compounds of the present invention, $R^9$ is preferably selected from the group consisting of hydrogen, methyl, and ethyl.

More preferably, $R^9$ is hydrogen.

In the compounds of the present invention, m is preferably an integer from 0 to 4, more preferably from 2 to 4.

In the compounds of the present invention, n is preferably an integer from 0 to 4, more preferably from 2 to 4.

In the compounds of the present invention, r is preferably an integer from 1 to 2.

In the compounds of the present invention, s is preferably an integer from 0 to 2.

In the compounds of the present invention, t is preferably an integer from 0 to 2, more preferably from 0 to 1.

Illustrative but nonlimiting examples of compounds of the present invention that are useful as integrin receptor antagonists are the following:

3-(5-(5,6,7,8-Tetrahydro[1,8]naphthyridin-2-yl)-pentanoylamino)-propionic acid;

3(S)-(Pyridin-3-yl)-3-(5-(5,6,7,8-tetrahydro[1,8]naphthyridin-2-yl)-pentanoylamino)-propionic acid;

3(S)-(5,6,7,8-Tetrahydroquinolin-3-yl)-3-(5-(5,6,7,8-tetrahydro[1,8]naphthyridin-2-yl)-pentanoylamino)-propionic acid (trifluoroacetate);

2(S)-Benzenesulfonylamino-3-(5-(5,6,7,8-tetrahydro-[1,8]naphthyridin-2-yl)-pentanoylamino)-propionic acid trifluoroacetate;

3(S)-(Quinolin-3-yl)-3-(5-(5,6,7,8-tetrahydro-[1,8]naphthyridin-2-yl)-pentanoylamino)-propionic acid;

3(R)-(Quinolin-3-yl)-3-(5-(5,6,7,8-tetrahydro-[1,8]naphthyridin-2-yl)-pentanoylamino)-propionic acid;

3-(Quinolin-3-yl)-3-(7-(5,6,7,8-tetrahydro-[1,8]naphthyridin-2-yl)-heptanoylamino)-propionic acid bis(trifluoroacetate);

3-(Quinolin-3-yl)-3-(6-(5,6,7,8-tetrahydro-[1,8]naphthyridin-2-yl)-hexanoylamino)-propionic acid;

3(S)-(3-Fluorophenyl)-3-(4(5,6,7,8-tetrahydro-[1,8]naphthyridin-2-ylamino)-butyrylamino)-propionic acid bis(trifluoroacetate);

3(S)-(5-(5,6,7,8-Tetrahydro-[1,8]naphthyridin-2-yl)-pentanoylamino)-pent-4-enoic acid;

3(S)-(3-Fluorophenyl)-3-(5-(5,6,7,8-tetrahydro-[1,8]naphthyridin-2-yl)-pentanoylamino)-propionic acid;

2-(3-Fluorophenyl)-3-(5-(5,6,7,8-tetrahydro-[1,8]naphthyridin-2-yl)-pentanoylamino)-propionic acid trifluoroacetate salt;

3(S)-(Benzo[1,3]dioxol-5-yl)-3-(5-(5,6,7,8-tetrahydro-[1,8]naphthyridin-2-yl)-pentanoylamino)-propionic acid;

3(S)-(2,3-Dihydro-benzofuran-6-yl)-3-(5-(5,6,7,8-tetrahydro-[1,8]naphthyridin-2-yl)-pentanoylamino)-propionic acid;

3(S)-(2-Oxo-2,3-dihydro-benzoxazol-6-yl)-3-(5-(5,6,7,8-tetrahydro-[1,8]naphthyridin-2-yl)-pentanoylamino)-propionic acid trifluoroacetate;

3(S)-(3-Fluorophenyl)-3{3-[(5,6,7,8-tetrahydro-[1,8]naphthyridin-2-ylmethyl)-amino]-propionylamino}-propionic acid;

3(S)-(3-Fluorophenyl)-3-(2-{propyl-[2-(5,6,7,8-tetrahydro-[1,8]naphthyridin-2-yl)-ethyl]-amino}-acetylamino)-propionic acid trifluoroacetate;

3(S)-(3-Fluorophenyl)-3-(2-{phenethyl-[2-(5,6,7,8-tetrahydro-[1,8]naphthyridin-2-yl)-ethyl]-amino}-acetylamino)-propionic acid trifluoroacetate;

3(S)-(3-Fluorophenyl)3-{3(S)-[(5,6,7,8-tetrahydro-[1,8] naphthyridin-2-ylmethyl)-amino]-pent-4-ynoylamino}-propionic acid;

3(S)-(3-Fluorophenyl)-3-{3(S)-(3-fluorophenyl)-3-[(5,6,7,8-tetrahydro-[1,8]naphthyridin-2-ylmethyl)-amino]-propionylamino}-propionic acid bis(trifluoroacetate);

3(S)-(3-Fluoro-4-phenyl-phenyl)-3-(5-(5,6,7,8-tetrahlydro-[1,8]naphthyridin-2-yl)-pentanoylamino)-propionic acid trifluoroacetate;

2(S)-(2-Thienylsulfonylamino)-3-(5-(5,6,7,8-tetrahydro-[1,8]naphthyridin-2-yl)-pentanoylamino)-propionic acid trifluoroacetate;

3(S)-(3-Fluorophenyl)-3-{3-methyl-3-[(5,6,7,8-tetrahydro-[1,8]naphthyridin-2-ylmethyl)-amino]-propionylamino}-propionic acid;

3(S)-(3-Fluorophenyl)-3-{2-[2-(5,6,7,8-tetrahydro-[1,8] naphthyridin-2-yl)-ethylamino]-acetylamino}-propionic acid;

3(S)-(3-Fluorophenyl)-3{[3-(5,6,7,8-tetrahydro-[1,8] naphthyridin-2-yl)-propyl]-ureido}-propionic acid;

2(S)-(Methanesulfonylamino)-3-(5-(5,6,7,8-tetrahydro-[1,8]naphthyridin-2-yl)-pentanoylamino)-propionic acid;

3(S)-(2,3-Dihydro-benzofuran-6-yl)-3-[3-(1,2,3,4,6,7,8(R or S),9-octahydro-benzo[b][1,8]naphthyridin-8-yl)-propionylamino]-propionic acid;

3(S)-(2,3-Dihydro-benzofuran-6-yl)-3-[3-(1,2,3,4,6,7,8(S or R),9-octahydro-benzo[b][1,8]naphthyridin-8-yl)-propionylamino]-propionic acid;

3(S)-(6-Methoxy-pyridin-3-yl)-3-[N-methyl-3-(1,2,3,4,6,7,8,9-octahydro-benzo[b][1,8]naphthyridin-8-yl-propionyl)-amino]propionic acid;

3(S)-(2,3-Dihydro-benzofuran-6-yl)-3-[3-(5,6,7,8-tetrahydro-[1,8]-naphthyridin-2-ylmethylsulfanyl) propionylamino]-propionic acid bis(trifluoroacetate);

3-(Quinolin-3-yl)-7-[(5,6,7,8-tetrahydro-[1,8]-naphthyridin-2-ylmethyl)amino]-heptanoic acid;

3-(Quinolin-3-yl)-7-[acetyl-(5,6,7,8-tetrahydro-[1,8]-naphthyridin-2-ylmethyl)amino]-heptanoic acid;

3-(Quinolin-3-yl)-7-[methanesulfonyl-(5,6,7,8-tetrahydro-[1,8]-naphthyridin-2-ylmethyl)amino]-heptanoic acid;

3-[5-(2-Amino-pyrimidin-4-yl)-pentanoylamino]-3(S)-(quinolin-3-yl)-propionic acid;

9-(5,6,7,8-Tetrahydro-[1,8]-naphthyridin-2-yl)-nonanoic acid;

2-(Benzenesulfonylamino)-9-(5,6,7,8-tetrahydro-[1,8]-naphthyridin-2-yl)-non-4-enoic acid bis (trifluoroacetate);

2(S)-(Benzenesulfonylamino)-9-(5,6,7,8-tetrahydro-[1,8] naphthyridin-2-yl)-nonanoic acid;

2(R)-(Benzenesulfonylamino)-9-(5,6,7,8-tetrahydro-[1,8] naphthyridin-2-yl)-nonanoic acid;

2(S)-(Benzenesulfonylamino)-10-(5,6,7,8-tetrahydro-[1,8]naphthyridin- 2-yl)-decanoic acid;

2(S)-(Benzenesulfonylamino)-8-(5,6,7,8-tetrahydro-[1,8] naphthyridin-2-yl)-octanoic acid;

2(S)-(Cyclohexylmethanesulfonylamino)-9-(5,6,7,8-tetrahydro-[1,8]naphthyridin-2-yl)-nonanoic acid hydrochloride;

2(S)-(7,7-Dimethyl-2-oxo-bicyclo[2.2.1]hept-1(S)-ylmethanesulfonylamino)-9-(5,6,7,8-tetrahydro-[1,8] naphthyridin-2-yl)-nonanoic acid hydrochloride;

2(S)-(Phenylmethanesulfonylamino)-9-(5,6,7,8-tetrahydro-[1,8]naphthyridin-2-yl)-nonanoic acid;

2(S)-(Cyclohexanesulfonylamino)-9-(5,6,7,8-tetrahydro-[1,8]naphthyridin-2-yl)-nonanoic acid hydrochloride;

2(S)-(Butane-1-sulfonylamino)-9-(5,6,7,8-tetrahydro-[1,8]naphthyridin-2-yl)-nonanoic acid hydrochloride;

2(S)-(3-Benzylureido)-9-(5,6,7,8-tetrahydro-[1,8] naphthyridin-2-yl)-nonanoic acid;

2(S)-(Benzyloxycarbonylamino)-9-(5,6,7,8-tetrahydro-[1,8]naphthyridin-2-yl)-nonanoic acid;

2(S)-(Phenylacetylamino)-9-(5,6,7,8-tetrahydro-[1,8] naphthyridin-2-yl)-nonanoic acid;

2(S)-(Acetylamino)-9-(5,6,7,8-tetrahydro-[1,8] naphthyridin-2-yl)-nonanoic acid;

2(S)-(Benzoylamino)-9-(5,6,7,8-tetrahydro-[1,8] naphthyridin-2-yl)-nonanoic acid;

3-(Quinolin-3-yl)-9-(5,6,7,8-tetrahydro-[1,8]-naphthyridin-2-yl)-nonanoic acid;

3(S)-(Quinolin-3-yl)-9-(5,6,7,8-tetrahydro-[1,8]-naphthyrid-2-yl)-nonanoic acid;

3(R)-(Quinolin-3-yl)-9-(5,6,7,8-tetrahydro-[1,8]-naphthyridin-2-yl)-nonanoic acid;

3-(Quinolin-3-yl)-7-(1,2,3,4,6,7,8,9-octahydro-benzo[b][1,8]-naphthyridin-8-yl)-heptanoic acid bis (hydrochloride);

6-Oxo-$^3$-(quinolin-3-yl)-9-(5,6,7,8-tetrahydro-[1,8]-naphthyridin-2-yl)-nonanoic acid;

3-(N-Oxo-quinolin-3-yl)-9-(5,6,7,8-tetrahydro-[1,8]-naphthyridin-2-yl)-nonanoic acid;

3-(Phenyl)-9-(5,6,7,8-tetrahydro-[1,8]-naphthyridin-2-yl)-nonanoic acid;

3-(Benzo[b]thiophen-2-yl)-9-(5,6,7,8-tetrahydro-[1,8]-naphthyridin-2-yl)-nonanoic acid;

3(R)-(Benzo[b]thiophen-2-yl)-9-(5,6,7,8-tetrahydro-[1,8]-naphthyridin-2-yl)-nonanoic acid;

3(S)-(Benzo[b]thiophen-2-yl)-9-(5,6,7,8-tetrahydro-[1,8]-naphthyridin-2-yl)-nonanoic acid;

3-(Pyridin-3-yl)-9-(5,6,7,8-tetrahydro-[1,8]-naphthyridin-2-yl)-nonanoic acid;

3(R)-(Pyridin-3-yl)-9-(5,6,7,8-tetrahydro-[1,8]-naphthyridin-2-yl)-nonanoic acid;

3(S)-(Pyridin-3-yl)-9-(5,6,7,8-tetrahydro-[1,8]-naphthyridin-2-yl)-nonanoic acid;

3-(3-Fluorophenyl)-9-(5,6,7,8-tetrahydro-[1,8]-naphthyridin-2-yl)-nonanoic acid;

3(R)-(3-Fluorophenyl)-9-(5,6,7,8-tetrahydro-[1,8]-naphthyridin-2-yl)-nonanoic acid;

3(S)-(3-Fluorophenyl)-9-(5,6,7,8-tetrahydro-[1,8]-naphthyridin-2-yl)-nonanoic acid;

3-(2,3-Dihydro-benzofuran-6-yl)-9-(5,6,7,8-tetrahydro-[1,8]-naphthyridin-2-yl)-nonanoic acid;

3(S)-(2,3-Dihydro-benzofuran-6-yl)-9-(5,6,7,8-tetrahydro-[1,8]-naphthyridin-2-yl)-nonanoic acid;

3(R)-(2,3-Dihydro-benzofuran-6-yl)9-(5,6,7,8-tetrahydro-[1,8]-naphthyridin-2-yl)-nonanoic acid;

3-(2,3-Dihydro-benzofuran-6-yl)-9-(5,6,7,8-tetrahydro-[1,8]-naphthyridin-2-yl)-non-4-enoic acid trifluoroacetate;

3-(2,3-Dihydro-furo[3,2-b]pyridin-5-yl)-9-(5,6,7,8-tetrahydro-[1,8]naphthyridin-2-yl)-nonanoic acid;

3(R)-(2,3-Dihydro-furo[3,2-b]pyridin-5-yl)-9-(5,6,7,8-tetrahydro-[1,8]naphthyridin-2-yl)-nonanoic acid;

3(S)-(2,3-Dihydro-furo[3,2-b]pyridin-5-yl)-9-(5,6,7,8-tetrahydro-[1,8]naphthyridin-2-yl)-nonanoic acid;

3-(Furo[2,3b]pyridin-5-yl)-9-(5,6,7,8-tetrahydro-[1,8]naphthyridin-2-yl)-nonanoic acid;

3(R)-(Furo[2,3b]pyridin-5-yl)-9-(5,6,7,8-tetrahydro-[1,8]naphthyridin-2-yl)-nonanoic acid;

3(S)-(Furo[2,3b]pyridin-5-yl)-9-(5,6,7,8-tetrahydro-[1,8]naphthyridin-2-yl)-nonanoic acid;

3-(2,3-Dihydro-furo[2,3-b]pyridin-5-yl)-9-(5,6,7,8-tetrahydro-[1,8]naphthyridin-2-yl)-nonanoic acid;

3(R)-(2,3-Dihydro-furo[2,3-b]pyridin-5-yl)-9-(5,6,7,8-tetrahydro-[1,8]naphthyridin-2-yl)-nonanoic acid;

3(S)-(2,3-Dihydro-furo[2,3-b]pyridin-5-yl)-9-(5,6,7,8-tetrahydro-[1,8]naphthyridin-2-yl)-nonanoic acid;

3-(6-Methoxy-pyridin-3-yl)-9-(5,6,7,8-tetrahydro-[1,8]-naphthyridin-2-yl)-nonanoic acid;

3(S)-(6-Methoxy-pyridin-3-yl)-9-(5,6,7,8-tetrahydro-[1,8]-naphthyridin-2-yl)-nonanoic acid;

3(R)-(6-Methoxy-pyridin-3-yl)-9-(5,6,7,8-tetrahydro-[1,8]-naphthyridin-2-yl)-nonanoic acid;

3-(Pyrimidin-5-yl)-9-(5,6,7,8-tetrahydro-[1,8]-naphthyridin-2-yl)-nonanoic acid trifluoroacetate;

3(R)-(Pyrimidin-5-yl)-9-(5,6,7,8-tetrahydro-[1,8]-naphthyridin-2-yl)-nonanoic acid trifluoroacetate;

3(S)-(Pyrimidin-5-yl)-9-(5,6,7,8-tetrahydro-[1,8]-naphthyridin-2-yl)-nonanoic acid trifluoroacetate;

3-(6-Amino-pyridin-3-yl)-9-(5,6,7,8-tetrahydro-[1,8]-naphthyridin-2-yl)-nonanoic acid;

3(R)-(6-Amino-pyridin-3-yl)-9-(5,6,7,8-tetrahydro-[1,8]-naphthyridin-2-yl)-nonanoic acid;

3(S)-(6-Amino-pyridin-3-yl)-9-(5,6,7,8-tetrahydro-[1,8]-naphthyridin-2-yl)-nonanoic acid;

3-(Benzo[b]thiazol-2-yl)-9-(5,6,7,8-tetrahydro-[1,8]-naphthyridin-2-yl)-nonanoic acid hydrochloride;

3(R)-(Benzo[b]thiazol-2-yl)-9-(5,6,7,8-tetrahydro-[1,8]-naphthyridin-2-yl)-nonanoic acid hydrochloride;

3(S)-(Benzo[b]thiazol-2-yl)-9-(5,6,7,8-tetrahydro-[1,8]-naphthyridin-2-yl)-nonanoic acid hydrochloride;

3-(6-Oxo-1,6-dihydro-pyridin-3-yl)-9-(5,6,7,8-tetrahydro-[1,8]-naphthyridin-2-yl)-nonanoic acid bis-(trifluoroacetate);

and the pharmaceutically acceptable salts thereof.

Further illustrative of the present invention are the compounds selected from the group consisting of 3(S-(Pyridin-3-yl)-3-(5-(5,6,7,8-tetrahydro[1,8]naphthyridin-2-yl)-pentanoylamino)-propionic acid;

2(S)-Benzenesulfonylamino-3-(5-(5,6,7,8-tetrahydro-[1,8]naphthyridin-2-yl)-pentanoylamino)-propionic acid trifluoroacetate;

3(S)-(Quinolin-3-yl)-3-(5-(5,6,7,8-tetrahydro-[1,8]naphthyridin-2-yl)-pentanoylamino)-propionic acid;

3(R)-(Quinolin-3-yl)-3-(5-(5,6,7,8-tetrahydro-[1,8]naphthyridin-2-yl)-pentanoylamino)-propionic acid;

2(S)-(2-Thienylsulfonylamino)-3-(5-(5,6,7,8-tetrahydro-[1,8]naphthyridin-2-yl)-pentanoylamino)-propionic acid trifluoroacetate;

3(S)-(2,3-Dihydro-benzofuran-6-yl)-3-[3-(1,2,3,4,6,7,8(R or S),9-octahydro-benzo[b][1,8]naphthyridin-8-yl)-propionylamino]-propionic acid;

3(S)-(2,3-Dihydro-benzofuran-6-yl)-3-[3-(1,2,3,4,6,7,8(S or R),9-octahydro-benzo[b][1,8]naphthyridin-8-yl)-propionylamino]-propionic acid;

3(S)-(6-Methoxy-pyridin-3-yl)-3-[N-methyl-3-(1,2,3,4,6,7,8,9-octahydro-benzo[b][1,8]naphthyridin-8-yl-propionyl)-amino]propionic acid;

3-[5-(2-Amino-pyrimidin-4-yl)-pentanoylamino]-3 (S)-(quinolin-3-yl)-propionic acid;

2-(Benzenesulfonylamino)-9-(5,6,7,8-tetrahydro-[1,8]-naphthyridin-2-yl)-non-4-enoic acid bis (trifluoroacetate);

and the pharmaceutically acceptable salts thereof.

Yet further illustrative are the compounds selected from the group consisting of 3(R)-(Quinolin-3-yl)-9-(5,6,7,8-tetrahydro-[1,8]-naphthyridin-2-yl)-nonanoic acid;

3(S)-(Quinolin-3-yl)-9-(5,6,7,8-tetrahydro-[1,8]-naphthyridin-2-yl)-nonanoic acid;

3(R)-(Benzo[b]thiophen-2-yl)-9-(5,6,7,8-tetrahydro-[1,8]-naphthyridin-2-yl)-nonanoic acid;

3(S)-(Benzo[b]thiophen-2-yl)-9-(5,6,7,8-tetrahydro-[1,8]-naphthyridin-2-yl)-nonanoic acid;

3(R)-(Pyridin-3-yl)-9-(5,6,7,8-tetrahydro-[1,8]-naphthyridin-2-yl)-nonanoic acid;

3(S)-(Pyridin-3-yl)-9-(5,6,7,8-tetrahydro-[1,8]-naphthyridin-2-yl)-nonanoic acid;

3(R)-(3-Fluorophenyl)-9-(5,6,7,8-tetrahydro-[1,8]-naphthyridin-2-yl)-nonanoic acid;

3(S)-(3-Fluorophenyl)-9-(5,6,7,8-tetrahydro-[1,8]-naphthyridin-2-yl)-nonanoic acid;

3(R)-(2,3-Dihydro-benzofuran-6-yl)-9-(5,6,7,8-tetrahydro-[1,8]-naphthyridin-2-yl)-nonanoic acid;

3(S)-(2,3-Dihydro-benzofuran-6-yl)-9-(5,6,7,8-tetrahydro-[1,8]-naphthyridin-2-yl)-nonanoic acid;

3(R)-(2,3-Dihydro-furo[3,2-b]pyridin-5-yl)-9-(5,6,7,8-tetrahydro-[1,8]naphthyridin-2-yl)-nonanoic acid;

3(S)-(2,3-Dihydro-furo[3,2-b]pyridin-5-yl)-9-(5,6,7,8-tetrahydro-[1,8]naphthyridin-2-yl)-nonanoic acid;

3(R)-(Furo[2,3b]pyridin-5-yl)-9-(5,6,7,8-tetrahydro-[1,8]naphthyridin-2-yl)-nonanoic acid;

3(S)-(Furo[2,3b]pyridin-5-yl)-9-(5,6,7,8-tetrahydro-[1,8]naphthyridin-2-yl)-nonanoic acid;

3(R)-(2,3-Dihydro-furo[2,3-b]pyridin-5-yl)-9-(5,6,7,8-tetrahydro-[1,8]naphthyridin-2-yl)-nonanoic acid;

3(S)-(2,3-Dihydro-furo[2,3-b]pyridin-5-yl)-9-(5,6,7,8-tetrahydro-[1,8]naphthyridin-2-yl)-nonanoic acid;

3(R)-(6-Methoxy-pyridin-3-yl)-9-(5,6,7,8-tetrahydro-[1,8]-naphthyridin-2-yl)-nonanoic acid;

3(S)-(6-Methoxy-pyridin-3-yl)-9-(5,6,7,8-tetrahydro-[1,8]-naphthyridin-2-yl)-nonanoic acid;

3(R)-(Pyrimidin-5-yl)-9-(5,6,7,8-tetrahydro-[1,8]-naphthyridin-2-yl)-nonanoic acid;

3(S)-(Pyrimidin-5-yl)-9-(5,6,7,8-tetrahydro-[1,8]-naphthyridin-2-yl)-nonanoic acid;

3(R)-(6-Amino-pyridin-3-yl)-9-(5,6,7,8-tetrahydro-[1,8]-naphthyridin-2-yl)-nonanoic acid;

3(S)-(6-Amino-pyridin-3-yl)-9-(5,6,7,8-tetrahydro-[1,8]-naphthyridin-2-yl)-nonanoic acid;

3(R)-(Benzo[b]thiazol-2-yl)-9-(5,6,7,8-tetrahydro-[1,8]-naphthyridin-2-yl)-nonanoic acid hydrochloride;

3(S)-(Benzo[b]thiazol-2-yl)-9-(5,6,7,8-tetrahydro-[1,8]-naphthyridin-2-yl)-nonanoic acid hydrochloride;

and the pharmaceutically acceptable salts thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by HPLC using a chiral stationary phase. Alternatively, any enantiomer of a compound of the present invention may be obtained by stereospecific synthesis using optically pure starting materials or reagents of known configuration.

Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the $\alpha v \beta 3$ receptor, the $\alpha v \beta 5$ receptor, or the $\alpha v \beta 6$ receptor, or a compound which binds to and antagonizes combinations of these receptors (for example, a dual $\alpha v \beta 3 / \alpha v \beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-10}$ alky, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrryl, pyrazolyl, pyrazinyl, pyrimidinyl, imidazolyl, benzimidazolyl, benzthiazolyl, benzoxazolyl, indolyl, thienyl, furyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^1$ substituents, when on the same carbon atom, can be taken together with the carbon atom to which they are attached to form a carbonyl group.

In the compounds of the present invention, two $R^3$ substituents, when on the same carbon atom, can be taken together with the carbon atom to which they are attached to form a carbonyl group. In such instances, the limitation, that in the resultant compound the carbon atom or atoms at which $R^3$ is attached is itself attached to no more than one heteroatom, does not apply. Also, two $R^3$ substituents, when on the same carbon atom, can be taken together with the carbon atom to which they are attached to form a cyclopropyl group.

In the compounds of the present invention, $R^5$ and $R^6$ can be taken together to form a carbonyl group. In such instances, the limitation, that in the resultant compound the carbon atom at which $R^5$ and $R^6$ is attached is itself attached to no more than one heteroatom, does not apply.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

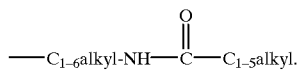

In choosing compounds of the present invention, one of ordinary skill in the art will recognize that the various substituents, i.e. X, Y, Z, $R^1$, $R^2$, $R^3$, $R^4$, $R^5$, $R^6$, $R^7$, $R^8$ and $R^9$, and the subscripts m, n, p, r, s, and t are to be chosen in conformity with well-known principles of chemical structure connectivity.

Representative compounds of the present invention typically display submicromolar affinity for the integrin receptors, particularly the αvβ3, αvβ5, and/or αvβ6 receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Further exemplifying the invention is the method wherein the integrin receptor antagonizing effect is an αvβ3 antagonizing effect. An illustration of the invention is the method wherein the αvβ3 antagonizing effect is selected from inhibition of bone resorption, restenosis, angiogenesis, diabetic retinopathy, macular degeneration, inflammation, viral disease, tumor growth, or metastasis. Preferably, the αvβ3 antagonizing effect is the inhibition of bone resorption.

An example of the invention is the method wherein the integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, tumor growth, or metastasis.

Illustrating the invention is the method wherein the integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammation, viral disease, tumor growth, or metastasis.

Illustrating the invention is the method wherein the integrin receptor antagonizing effect is an αvβ6 antagonizing effect. More particularly, the αvβ6 antagonizing effect is selected from inhibition of angiogenesis, inflammatory response, or wound healing.

Illustrating the invention is the method wherein the αvβ3 antagonizing effect is selected from inhibition of bone resorption, inhibition of restenosis, inhibition of angiogenesis, inhibition of diabetic retinopathy, inhibition of macular degeneration, inhibition of atherosclerosis, inflammation, viral disease, or inhibition of tumor growth and metastasis. Preferably, the αvβ3 antagonizing effect is the inhibition of bone resorption.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, viral disease, cancer, tumor growth, and metastasis. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an $\alpha v \beta 3$ antagonizing effect; more specifically the $\alpha v \beta 3$ antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of viral disease, or inhibition of tumor growth or metastasis. Most preferably, the $\alpha c \beta 3$ antagonizing effect is inhibition of bone resorption. Alternatively, the integrin antagonizing effect is an $\alpha v \beta 5$ antagonizing effect, an $\alpha v \beta 6$ antagonizing effect, or a mixed $\alpha v \beta 3$, $\alpha v \beta 5$, and $\alpha v \beta 6$ antagonizing effect. Examples of $\alpha v \beta 5$ antagonizing effects are inhibition of restenosis, atherosclerosis, angiogenesis, diabetic retinopathy, macular degeneration, inflammation, or tumor growth. Examples of $\alpha v \beta 6$ antagonizing effects are inhibition of angiogenesis, inflammatory response, and wound healing.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifwing the invention is the use of any of the compounds described above in the preparation of a medicament for the treatment and/or prevention of bone resorption, tumor growth, cancer, restenosis, atherosclerosis, diabetic retinopathy, macular degeneration, inflammation, viral disease, and/or angiogenesis.

Also exemplifying the invention are compositions further comprising an active ingredient selected from the group consisting of a.) an organic bisphosphonate or a pharmaceutically acceptable salt or ester thereof, b.) an estrogen receptor modulator, c.) a cytotoxic/antiproliferative agent, d.) a matrix metalloproteinase inhibitor, e.) an inhibitor of epidermal-derived, fibroblast-derived, or platelet-derived growth factors, f.) an inhibitor of VEGF, g.) an inhibitor of Flk-1/KDR, Flt-1, Tck/Tie-2, or Tie-1, h.) a cathepsin K inhibitor, and i.) a prenylation inhibitor, such as a farnesyl transferase inhibitor or a geranylgeranyl transferase inhibitor or a dual farnesyl/geranylgeranyl transferase inhibitor; and mixtures thereof.

(See B. Millauer et al., "Dominant-Negative Inhibition of Flk-1 Suppresses the Growth of Many Tumor Types in Vivo", *Cancer Research,* 56, 1615–1620 (1996), which is incorporated by reference herein in its entirety).

Preferably, the active ingredient is selected from the group consisting of:

a.) an organic bisphosphonate or a pharmaceutically acceptable salt or ester thereof, b.) an estrogen receptor modulator, and c.) a cathepsin K inhibitor; and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, or a cathepsin K inhibitor.

Additional illustrations of the invention are methods of treating tumor growth or metastasis in a mammal in need thereof, comprising administering to the mammal a therapeutically effective amount of a compound described above and one or more agents known to be cytotoxic/antiproliferative. Also, the compounds of the present invention can be administered in combination with radiation therapy for treating tumor growth and metastasis.

In addition, the integrin $\alpha v \beta 3$ antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an $\alpha v \beta 3$ receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an $\alpha v \beta 3$ antagonist.

The dosage regimen utilizing the compounds of the present invention is selected in accordance with a variety of factors including type, species, age, weight, sex and medical condition of the patient; the severity of the condition to be treated; the route of administration; the renal and hepatic finction of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg(day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic add, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:

AcOH: Acetic acid.
$BH_3$.DMS: Borane.dimethylsulfide.
BOC(Boc): t-Butyloxycarbonyl.
BOP: Benzotriazol-1-yloxytris(dimethylamino)-phosphonium hexafluorophosphate.
CBZ(Cbz): Carbobenzyloxy or benzyloxycarbonyl.
CDI: Carbonyldiimidazole.
$CH_2Cl_2$: Methylene chloride.
$CH_3CN$ Acetonitrile
$CHCl_3$: Chloroform.
DEAD: Diethyl azodicarboxylate.
DIAD: Diisopropyl azodicarboxylate.
DIBAH or
DIBAL-H: Diisobutylaluminum hydride.
DIPEA: Diisopropylethylamine.
DMAP: 4-Dimethylaminopyridine.
DME: 1,2-Dimethoxyethane.
DMF: Dimethylformamide.
DMSO: Dimethylsulfoxide.
DPFN: 3,5-Dimethyl-1-pyrazolylformamidine nitrate.
EDC: 1-(3-Dimethylaminopropyl)-3-ethylcarbodiiimide.HCl
EtOAc: Ethyl acetate.
EtOH: Ethanol.
HOAc: Acetic acid.
HOAT: 1-Hydroxy-7-azabenzotriazole
HOBT: 1-Hydroxybenzotriazole.
IBCF: Isobutylchloroformate
LDA: Lithium diisopropylamide.
MeOH: Methanol.
MMNG 1,1-methyl-3-nitro-1-nitrosoguanidine
$NEt_3$: Triethylamine.
NMM: N-methylmorpholine.
PCA.HCl: Pyrazole carboxamidine hydrochloride.
Pd/C: Palladium on activated carbon catalyst.

Ph: Phenyl.
PyCLU: Chloro-N,N,N',N'-(tetramethylene)-formamidinium hexafluorophosphate.
pTSA p-Toluenesulfonic acid.
TEA: Triethylamine.
TFA: Trifluoroacetic acid.
THF: Tetrahydrofuran.
TLC: Thin Layer Chromatography.
TMEDA: N,N,N',N'-Tetramethylethylenediamine.
TMS: Trimethylsilyl.

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published Dec. 7, 1995, and WO95/17397, published Jun. 29, 1995, both of which are incorporated by reference herein in their entirety, in conjunction with the disclosure contained herein, one of ordinary skill in the art can readily prepare additional compounds of the present invention claimed herein. Additionally, for a general review describing the synthesis of β-alanines which can be utilized as the C-terminus of the compounds of the present invention, see Cole, D. C., *Recent Stereoselective Synthetic Approaces to β-Amino Acids, Tetrahedron,* 1994, 50, 9517–9582; Juaristi, E, et al., *Enantioselective Synthesis of β-Amino Acids, Aldrichimica Acta,* 1994, 27, 3. In particular, synthesis of the 3-methyl-β-alanine is taught in Duggan, M. F. et al., *J. Med. Chem.,* 1995, 38, 3332–3341; the 3-ethynyl-β-alanine is taught in Zablocki, J. A., et al., *J. Med. Chem.,* 1995, 38, 2378–2394; the 3-(pyridin-3-yl)-β-alanine is taught in Rico, J. G. et al., *J. Org. Chem.,* 1993, 58, 7948–7951; and the 2-amino- and 2-tosylamino-β-alanines are taught in Xue, C-B, et al., *Biorg. Med. Chem. Letts.,* 1996, 6, 339–344. The references described in this paragraph are all also incorporated by reference herein in their entirety.

SCHEME 1

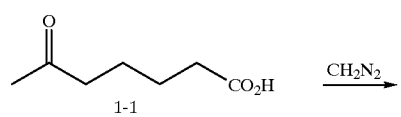

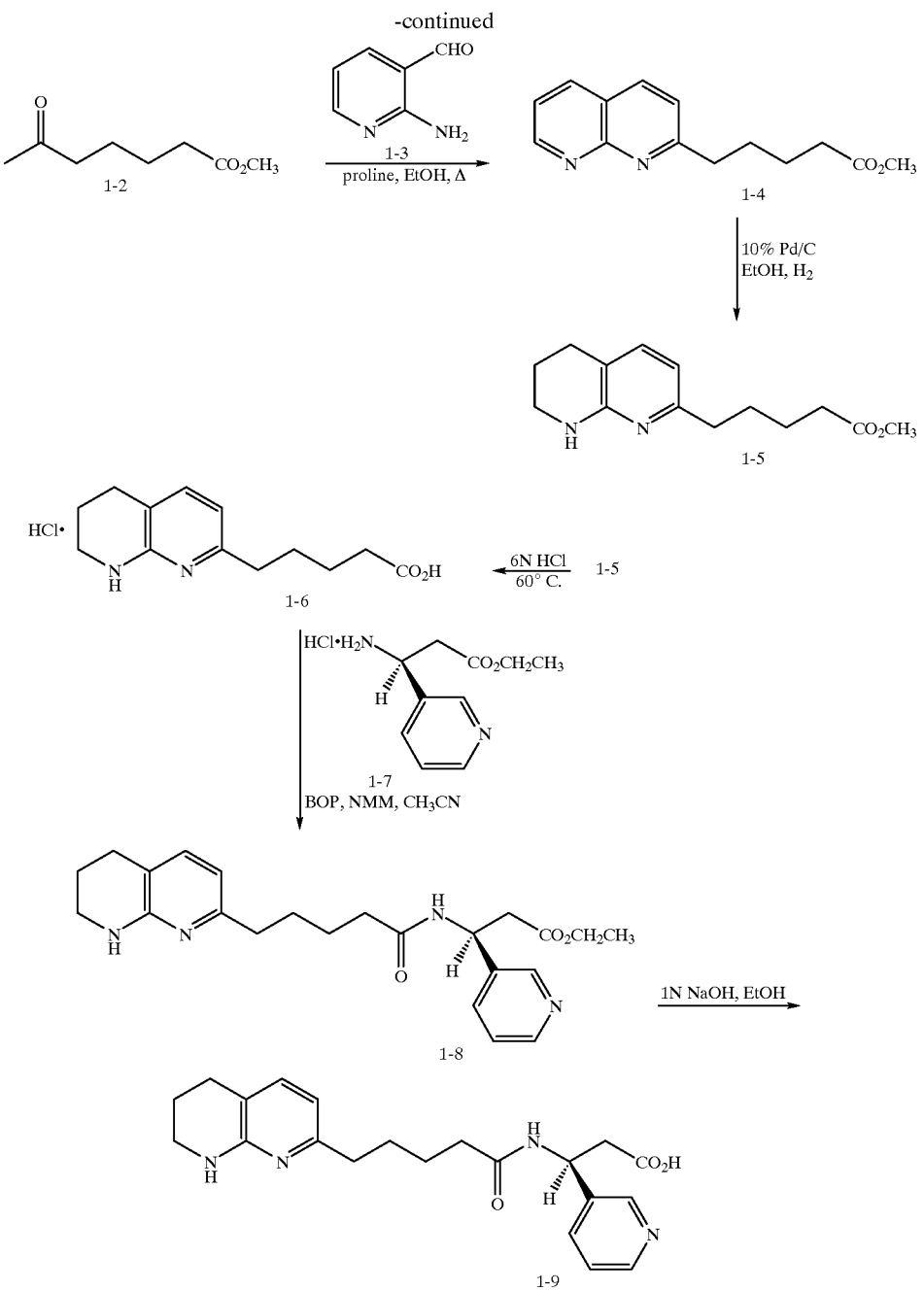

6-Oxo-heptanoic acid methyl ester (1-2)

To a rapidly stirred mixture of diethyl ether (175 ml) and 40% KOH (52 ml) at 0° C. was added MNNG (15.4 g, 105 mmol). The mixture was stirred for 10 minutes. The ethereal layer was transferred to a solution of 6-oxo-heptanoic acid 1-1 (5.0 g, 34.68 mmol) and $CH_2Cl_2$ at 0° C. The solution was purged with argon for 30 minutes and then concentrated. Flash chromatography (silica, 30% to 50% EtOAc/hexanes) gave ester 1-2 as a clear oil.

TLC $R_f$=0.88 (silica, EtOAc)

$^1$H NMR (300 MHz, $CDCl_3$) δ 3.67 (s, 3H), 2.46 (m,2H), 2.33 (m, 2H), 2.14 (s, 3H), 1.62 (m, 4H).

5-[1,8]-Naphthyridin-2-yl-pentanoic acid methyl ester (1-4)

A mixture of 1-2 (1.4 g, 9.04 mmol), 1-3, 2-amino-3-formylpyridine (552 mg, 4.52 mmol) (for preparation, see: J. Org. Chem., 1983, 48, 3401), and proline (260 mg, 2.26 mmol) in absolute ethanol (23 mL) was heated at reflux for 18 h. Following evaporative removal of the solvent, the residue was chromatographed (silica gel, 80% ethyl acetate/hexane, then ethyl acetate) to give ester 1-4 as a white solid.

TLC $R_f$=0.38 (silica, EtOAc)

$^1$H NMR (300 MHz, $CDCl_3$) δ 9.08 (m, 1H), 8.16 (d, J=8.0 Hz, 1H), 8.10 (d, J=8.3 Hz, 1H), 7.45 (m, 1H), 7.39 (d, J=8.3 Hz, 1H), 3.66 (s, 3H), 3.08 (t, J=7.6 Hz, 2H), 2.39 (t, J=7.6 Hz, 2H), 1.94 (m,2H), 1.78 (m, 2H).

5-(5,6,7,8-Tetrahydro-[1,8]naphthyridin-2-yl)-pentanoic acid methyl ester (1-5)

A mixture of 1-4 (630 mg, 2.58 mmol) and 10% Pd/carbon (95 mg) in EtOH (25 mL) was stirred under a balloon of hydrogen for 72 h. Following filtration and evaporative removal of the solvent, the residue was chromatographed (silica gel, 70% ethyl acetate/hexanes) to give 1-5 as a colorless oil.

TLC $R_f$=0.58 (silica, ethyl acetate).

$^1$H NMR (300 MHz, CDCl$_3$) δ 7.05 (d, J=7.3 Hz, 1H), 6.34 (d, J=7.3 Hz, 1H), 4.72 (s, 1H), 3.66 (s, 3H), 3.40 (m, 2H), 2.69 (t, J=6.3 Hz, 2H), 2.53 (m, 2H), 2.33 (m, 2H), 1.90 (m, 2H), 1.66 (m, 4H).

5-(5,6,7,8-Tetrahydro-[1,8]naphthyridin-2-yl)-pentanoic acid hydrochloride (1-6)

A mixture of 1-5 (620 mg, 2.50 mmol) and 6N HCl (12 mL) was heated at 50° C. for 18 h. Evaporative removal of the solvent gave 1-6 as a yellow solid.

$^1$H NMR (300 MHz, CD$_3$OD) δ 7.59 (d, J=7.3 Hz, 1H), 6.63 (d, J=7.3 Hz, 1H), 3.48 (m, 2H), 2.82 (m, 2H), 2.72 (m, 2H), 2.35 (m, 2H), 1.95 (m, 2H), 1.69 (m, 4H).

3(S)-(Pyridin-3-yl)-3-(5-(5,6,7,8-tetrahydro-[1,8]naphthyridin-2-yl)-pentanoylamino)propionic acid ethyl ester (1-8)

A mixture of 1-6 (50 mg, 0.1847 mmol), 1-7 (49 mg, 0.1847 mmol) (Rico et al., *J. Org. Chem.*, 1993, 58, 7948), BOP (90 mg, 0.2032 mmol) and NMM (0.122 mL, 1.11 mmol) in CH$_3$CN (2 mL) was stirred for 18 h. The mixture was diluted with ethyl acetate, washed with sat. NaHCO$_3$, brine, and dried over MgSO$_4$. Following evaporative removal of the solvent, the residue was chromatographed (silica gel, 20% MeOH/ethyl acetate) to give 1-8 as a yellow oil.

TLC $R_f$=0.23 (20% MeOH/ethyl acetate).

$^1$H NMR (300 MHz, CDCl$_3$) δ 8.54 (s,1H), 8.43 (d, J=4.9Hz, 1H), 8.15 (d, J=8.3 Hz, 1H), 7.85 (m, 1H), 7.39 (m, 1H), 7.15 (d, J=7.3Hz, 1H), 6.34 (d, J=7.3 Hz, 1H), 5.37 (t, J=7.3 Hz, 1H), 4.05 (q, J=7.1 Hz, 2H), 3.38 (t, J=5.5 Hz, 2H), 2.64 (m,4H),2.52 (m, 2H), 2.22 (m, 2H), 1.86 (m, 2H), 1.64 (m, 4H), 1.16 (t, J=7.1 Hz,3H).

3(S)-(Pyridin-3-yl)-3-(5-(5,6,7,8-tetrahydro-[1,8]naphthyridin-2-yl)-pentanoylamino)propionic acid (1-9)

To a solution of 1-8 (0.1847 mmol) in EtOH (2 mL) was added 1N NaOH (0.250 ml, 0.250 mmol). After stirring for 2 h, the solvents were evaporated and the residue was chromatographed (silica gel, 15:10:1:1 ethyl acetate/EtOH/water/NH$_4$OH) to give 1-9 as a white solid.

TLC $R_f$=0.15 (15:10:1:1 ethyl acetate/EtOH/water/NH$_4$OH).

$^1$H NMR (300 MHz, CD$_3$OD) δ 8.55 (s, 1H), 8.42 (d, J=4.9 Hz, 1H), 7.84 (d, J=8.1 Hz, 1H), 7.46 (d, J=7.3 Hz, 1H), 7.41 (m,1H), 6.50 (d,J=7.1 Hz, 1H), 5.42 (m, 1H,), 3.47 (t, J=5.6 Hz, 2H), 2.55 to 2.81 (m, 6H), 2.41 (m, 1H), 2.34 (m, 1H), 2.93 (m, 2H), 1.71 (m, 4H).

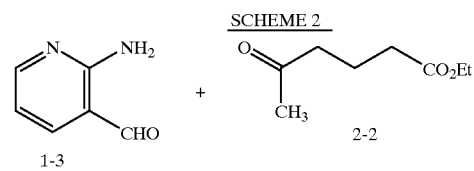

SCHEME 2

Ethyl 4-(1,8-naphthyridin-2-yl)butanoate (2-3)

Aminoaldehyde 1-3 (2.02 g, 16.6 mmol, prepared according to *Het.* 1993, 36, 2513), ketone 2-2 (5.3 mL, 33.1 mmol) and L-proline (0.48 g, 4.17 mmol) were combined in 75 mL EtOH. After heating at reflux overnight, the reaction was concentrated. Flash chromatography (silica, EtOAc) provided 2-3 as an off-white crystalline solid.

TLC $R_f$ 0.23 (silica, EtOAc)

$^1$H NMR (300 MHz, CDCl$_3$): δ9.09 (dd, J=4, 2 Hz, 1H), 8.17 (dd, J=8, 2 Hz, 1H), 8.12 (d, J=8 Hz, 1H), 7.46 (dd, J=8, 4 Hz, 1H), 7.42 (d, J=8 Hz, 1H), 4.12 (q, J=7 Hz, 2H), 3.11 (t, J=8 Hz, 2H), 2.44 (t, J=7 Hz, 1H), 2.26 (qn, J=8 Hz, 2H), 1.25 (t, J=7 Hz, 3H).

Ethyl 4-(1,2,3,4-tetrahydro-1,8-naphthyridin-7-yl)butanoate (2-4)

A solution of 2-3 (2.3 g, 9.4 mmol) in 50 mL EtOAc was treated with 10% Pd/C (230 mg) and a hydrogen balloon. After 4 days the reaction filtered through celite, concentrated, and purified by flash chromatography (silica, 70% EtOAc/hexane), providing 24 as a yellow oil.

TLC $R_f$ 0.40 (silica, EtOAc)

$^1$H NMR (300 MHz, CDCl$_3$): δ7.05 (d, J=7 Hz, 1H), 6.35 (d, J=7 Hz, 1H), 4.73 (br s, 1H), 4.12 (q, J=7 Hz, 2H), 2.69 (t, J=6 Hz, 2H), 2.57 (t, J=8 Hz, 2H), 2.33 (t, J=7 Hz, 2H), 1.98 (m, 2H), 1.90 (m, 2H), 1.25 (t, J=7 Hz, 3H).

4-(1,2,3,4-Tetrahydro-1,8-naphthyridin-7-yl)butanoic acid hydrochloride (2-5)

Ester 2-4 (1.8 g, 7.25 mmol) in 36 mL 6 N HCl was heated at 50° C. for 4 h, then concentrated, providing 2-5 as a yellow solid.

$^1$H NMR (300 MHz, CD$_3$OD): δ7.59 (d, J=7 Hz, 1H), 6.63 (d, J=7 Hz, 1H), 3.50 (t, J=5 Hz, 2H), 2.82 (t, J=6 Hz, 2H), 2.74 (t, J=8 Hz, 2H), 2.38 (t, J=7 Hz, 2H), 2.02–1.90 (m, 4H).

SCHEME 3

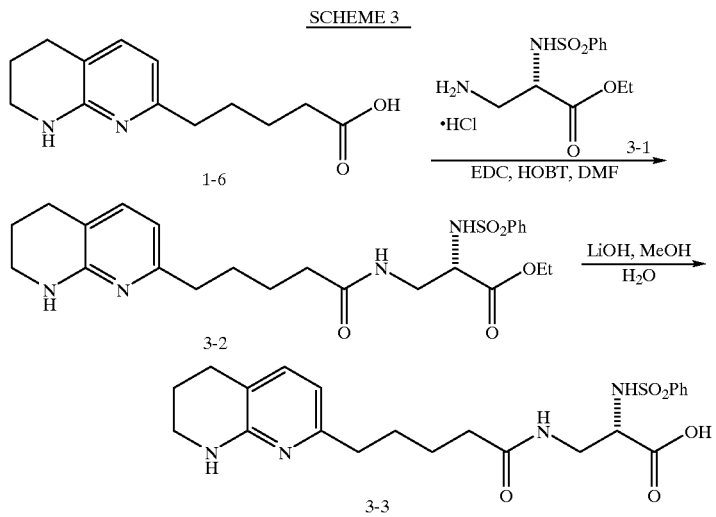

2(S)-Benzenesulfonylamino-3-(5-(5,6,7,8-tetrahydro-[1,8]naphthyridin-2-yl)-pentanoylamino)-propionic acid ethyl ester ditrifluoroacetate salt (3-2)

A solution of 5-(5,6,7,8-tetrahydro-[1,8]naphthyridin-2-yl)-pentanoic acid hydrochloride (1-6) (304 mg, 0.85 mmol) in DMF (5 mL) was treated successively with HOBT (115 mg, 0.85 mmol), the amine 3-1 (prepared in a similar fashion as intermediate A-4 but substituting benzenesulfonyl chloride in place of 4-iodo-benzenesulfonyl chloride) (263 mg, 0.85 mmol), EDC (195 mg, 1.02 mmol) and triethylamine (0.24 mL, 1.71 mmol). The resulting solution was stirred at room temperature for 18 hr., then poured into saturated NaHCO$_3$ and extracted twice with EtOAc. After washing with brine, the solvent was evaporated and the residue chromatographed (silica gel; 5% MeOH in CHCl$_3$) to give an oil.

Further purification using reverse phase HPLC afforded the title compound as a white solid.

FAB mass spectrum, found (M+H)$^+$=489.3

2(S)-Benzenesulfonylamino-3-(5-(5,6,7,8-tetrahydro-[1,8]naphthyridin-2-yl)-pentanoylamino)-propionic acid trifluoroacetate salt (3-3)

To a solution of the ester 3-2 (180 mg, 0.37 mmol) in methanol (2 mL) and water (2 mL) was added 1N LiOH (0.74 mL, 0.74 mmol) and the mixture was stirred for 4 hr. After this time, 1N HCl (1 mL) was added, and the solution was purified by reverse phase HPLC to provide the title compound as a white solid.

FAB mass spectrum, found (M+H)$^+$=461.21

SCHEME 4

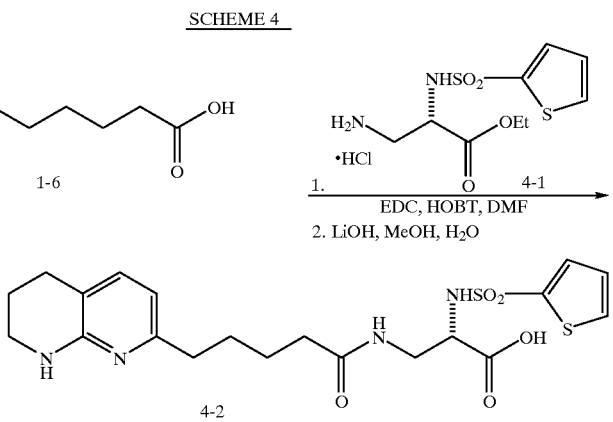

2(S)-(2-Thienylsulfonylamino)-3-(5-(5,6,7,8-tetrahydro-[1,8]naphthyridin-2-yl)-pentanoylamino)-propionic acid trifluoroacetate salt (4-2)

A solution of 5-(5,6,7,8-tetrahydro-[1,8]naphthyridin-2-yl)-pentanoic acid hydrochloride 1-6 (0.164 mg, 0.7 mmol) in DMF (5 mL) was treated successively with HOBT (104 mg, 0.77 mmol), the amine 4-1 (Egbertson, et al. *Bioorg Med Chem. Letts.,* 1996, 6, 2519; 211 mg, 0.85 mmol), EDC (161 mg, 0.84 mmol) and N-methylmorpholine (0.23 mL, 2.1 mmol). The resulting solution was stirred at room temperature for 18 hr., then poured into saturated NaHCO$_3$ and extracted twice with EtOAc. After washing with brine, the solvent was evaporated and the residue was used without further purification in the next step. To a solution of this ester (290 mg, 0.6 mmol) in 20 mL of THF, methanol and water (1:1:1) was added LiOH.H$_2$O (100 mg, 2.4 mmol) and the mixture was stirred for 20 hr. After this time, the THF and methanol were removed in vacuo and the aqueous solution was purified by reverse phase HPLC to provide the title compound as a white solid.

$^1$H NMR (CD$_3$OD) δ 7.73–7.78 (1H, dd), 7.54–7.62 (2H, m), 7.08–7.15 (1H, m), 6.60–6.67 (1H, d), 4.08–4.16 (1H, m), 3.57–3.67 (1H, dd), 3.40–3.50 (2H, t), 3.20–3.30 (1H, m), 2.75–2.85 (2H, t), 2.65–2.75 (2H, t), 2.20–2.30 (2H, t), 1.85–1.97 (2H, m), 1.60–1.80 (4H, m).

SCHEME 5

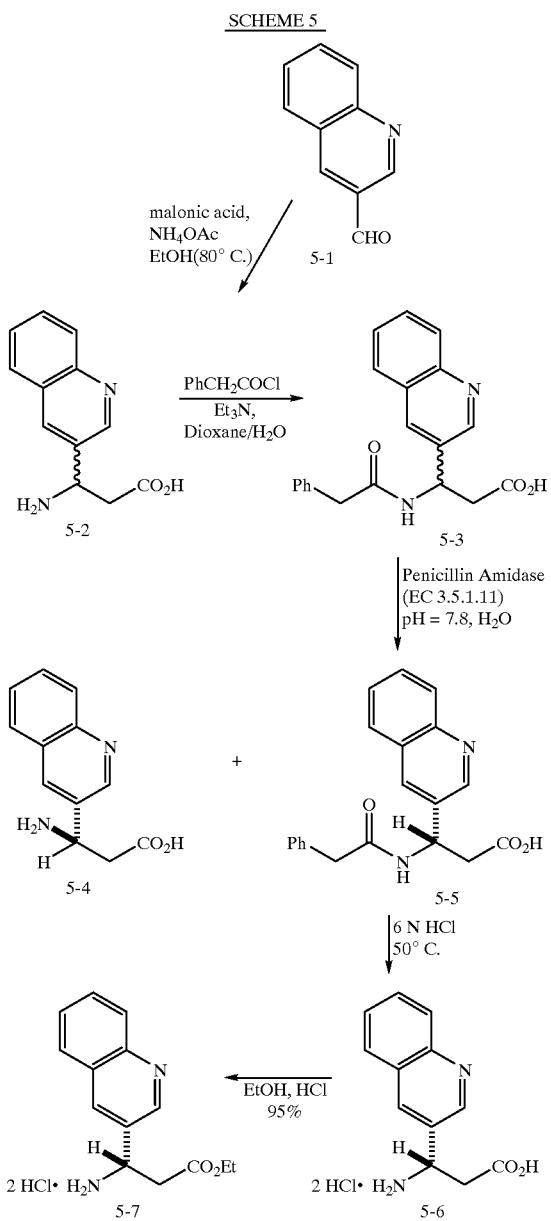

3-Amino-3-(quinolin-3-yl)-propionic acid (5-2)

A solution containing quinoline-3-carboxaldehyde 5-1 (5 g, 31.8 mmol), malonic acid (3.6 g, 35.0 mmol), and ammonium acetate (5.0 g, 63.6 mmol) in anhydrous ethanol (125 mL) was heated at reflux for 12 h. After cooling to room temperature, the resulting white solid was collected by filtration and washed with cold ethanol (150 mL) and then dried under vacuum to provide 5-2 as a white solid (3.84 g, 17.8 mmol, 56%).

$^1$H NMR (300 MHz, D$_2$O): δ8.91 (d, J=2 Hz 1H), 8.21 (d, J=2 Hz, 1H), 8.12 (d, J=8 Hz, 1H), 7.84 (d, J=7 Hz, 1H), 7.72 (t, J=7 Hz, 1H), 7.54 (t, J=7 Hz, 1,H), 4.72 (m, 1H), 2.73 (m, 2H).

3-Phenylacetylamino-3-(quinolin-3-yl)-propionic (5-3)

A 0° solution of 5-2 (3.5 g, 16.2 mmol) and NaHCO$_3$ (2.7 g, 32.4 mmol) in 50% aqueous dioxane (100 mL) was treated dropwise with a solution of phenylacetyl chloride (3.00 g, 19.4 mmol) in 25 mL of dioxane. The resulting solution was stirred at 0° for 2.5 h then warmed to room temperature, diluted with H$_2$O (50 mL) and washed with ether (2×100 mL). The aqueous layer was adjusted to pH=3 with 3N HCl and then extracted with CH$_2$Cl$_2$ (3×150 mL). The pooled organic extracts were dried, filtered and concentrated to afford 5-3 as an off white solid.

$^1$H NMR (300 MHz, CD$_3$OD): δ8.85 (d, J=2 Hz 1H), 8.20 (d, J=2 Hz, 1H), 8.00 (d, J=8 Hz, 1H), 7.86 (d, J=7 Hz, 1H), 7.76 (t, J=7 Hz, 1H), 7.52 (t, J=7 Hz, 1,H), 7.28 (m, 6H), 5.53 (t, J=6.8 Hz, 1H), 3.57 (s, 2H), 2.96 (m, 2H).

3-Amino-3(S)-(quinolin-3-yl)-propionic acid dihydrochloride (5-6)

Acid 5-3 (5.0 g, 15 mmol) was suspended in water (3.5 L) then treated with 1N NaOH (15 mL) to afford a clear solution. Penicillin amidase (Sigma, EC 3.5.1.11, 10,000 U) in 0.1 M phosphate buffer was added. The pH of the mixture was adjusted to 7.8 with 1N NaOH and the solution was stirred at room temperature for 4 days. The reaction was monitored periodically by HPLC and the reaction stopped once the 50% conversion was reached. Next, the reaction solution was cooled to 0° C. and adjusted to pH=3 with 3N HCl. An oily yellow precipitate formed and was collected by filtration then washed with water to afford crude 5-5 (1.8 g, 5.3 mmol). The filtrate was extracted with CH$_2$Cl$_2$ (3×500 mL) to afford additional 5-5 contaminated by phenylacetic acid. Both batches of crude 5-5 were combined and stirred in 3 N HCl (200 mL) at 50° for 12 h then cooled, washed with ether (2×100 mL) and evaporated to afford 5-6.

3-Amino-3-(quinolin-3-yl)-propionic acid ethyl ester dihydrochloride (5-7)

The resolved acid 5-6 was converted to 5-7 by refluxing in ethanolic HCl.

$^1$H NMR (300 MHz, CD$_3$OD): δ9.25 (d, J=2 Hz 1H), 8.31 (d, J=2 Hz, 1H), 8.15 (d, J=8 Hz, 1H), 7.84 (d, J=7 Hz, 1H), 7.72 (t, J=7 Hz, 1H), 7.54 (t, J=7 Hz, 1,H), 4.72 (m, 1H), 4.15 (q, J=6 Hz, 2H), 2.73 (m, 2H) 1.18 (t, J=6 Hz, 3H).

SCHEME 5 (CONTINUED)

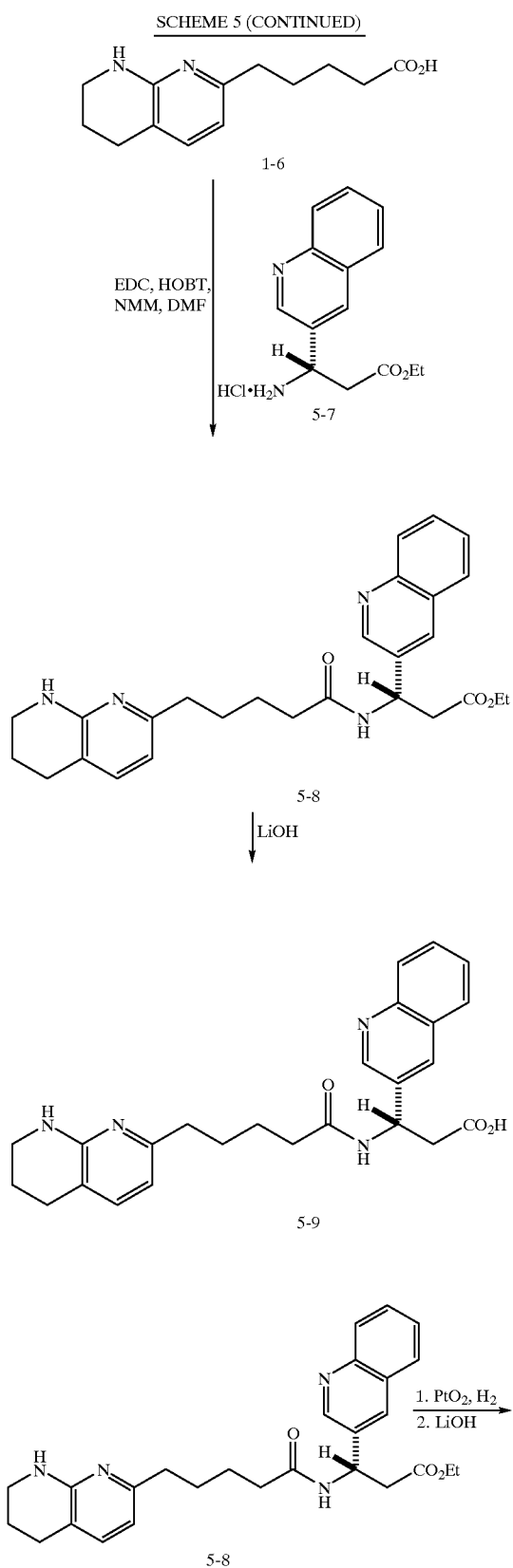

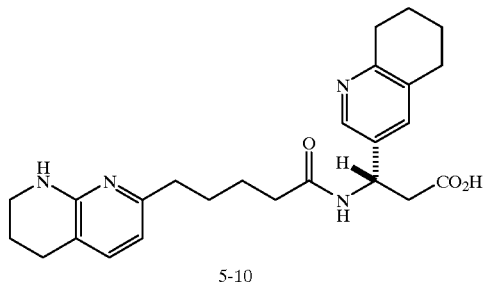

Ethyl 3-(5-(5,6,7,8-tetrahydro-[1,8]-naphthyridin-2-yl)pentanoylamino)-3(S)-(quinolin-3-yl)-propionate (5-8)

A mixture of 1-6 (200 mg, 0.74 mmol), 5-7 (202 mg, 0.74 mmol), NMM (366 mL, 3.33 mmol), HOBT (130 mg, 0.96 mmol) and EDC (184 mg, 0.96 mmol) in 2 mL DMF was stirred overnight. After diluting with EtOAc (100 mL), the mture was washed with sat. NaHCO$_3$, water, and brine, dried (MgSO$_4$), filtered and concentrated, and chromatographed on silica (10% EtOH/EtOAc) providing 5-8 as a colorless glass.

TLC R$_f$=0.6 (10% EtOH/EtOAc).

$^1$H NMR (300 MHz, CDCl$_3$) δ 8.80 (d, J=2 Hz 1H), 8.31 (d, J=2 Hz, 1H), 8.15 (d, J=8 Hz, 1H), 7.84 (d, J=7 Hz, 1H), 7.72 (t, J=7 Hz, 1H), 7.54 (t, J=7 Hz, 1,H), 7.00 (d, J=8.1 Hz, 1H), 6.53 (d, J=7.5 Hz, 1H), 5.34 (m, 1H), 4.06 (q, J=7,5 Hz, 2H),3.48 (t, J=5.7 Hz, 2H), 2.79 (m, 4H), 2.63 (m, 2H), 2.25 (m, 2H), 1.94 (m, 2H), 1.64 (m, 4H) 1.12 (t, J=7,5 Hz, 3H).

3(S)-(Quinolin-3-yl)-3-(5-(5,6,7,8-tetrahydro-[1,8]-naphthyridin-2-yl)pentanoylamino)-propionic acid (5-9)

Ester 5-8 (145 mg, 0.320 mmol) was dissolved in 1 mL EtOH and treated with 1N LiOH (352 mL, 0.35 mnmol) and stirred at room temperature overnight. The reaction solution was neutralized with 1N HCl (352 mL), evaporated, and purified by chromatography on silica gel (60% 20:1:1 EtOH/NH$_4$OH/H$_2$O—40% EtOAc) to afford 5-9 as a white solid.

TLC R$_f$=0.5 (60% 20:1:1 EtOH/NH$_4$OH/H$_2$O—40% EtOAc)

$^1$H NMR (300 MHz, CD$_3$OD) δ 8.80 (d, J=2 Hz 1H), 8.31 (d, J=2 Hz, 1H), 8.15 (d, J=8 Hz, 1H), 7.84 (d, J=7 Hz, 1H), 7.72 (t, J=7 Hz, 1H), 7.54 (t, J=7 Hz, 1,H), 7.00 (d, J=8.1 Hz, 1H), 6.53 (d, J=7.5 Hz, 1H), 5.34 (m, 1H), 3.48 (t, J=5.7 Hz, 2H), 2.79 (m, 4H), 2.63 (m, 2H), 2.25 (m, 2H), 1.94 (m, 2H), 1.64 (m, 4H).

3(S)-(5,6,7,8-Tetrahydro-quinolin-3-yl)-3-(5-(5,6,7,8-tetrahydro-[1,81]naphthyridin-2-yl)-pentanoylamino)-propionic acid trifluoroacetate (5-10)

A mixture of 5-8 (0.1 g, 0.3 mmol) and PtO$_2$ (0.04 g) in 10 mL TFA was purged with argon 3 times under vacuum, and treated under balloon hydrogenation condition for 18 hr. It was then filtered through a celite pad. The solution was concentrated. EtOH (3 mL) and LiOH (1 mL, 1 M, 1 mmol) were added. After stirring for 3 hr, the reaction mixture was treated with 2N HCl (2 mL), concentrated and purified by reverse phase HPLC (C18 column; gradient: H₂O/CH₃CN/TFA from 95:5:0.1 to 5:95:0.1 over 45 min) to give the desired product 5-10 as the TFA salt.

¹H NMR (300 MHz, CD₃OD) δ 8.50 (s, 1H), 8.23 (s, 1H), 7.52 (d, 1H), 6.54 (d, 1H), 5.33 (t, 1H), 3.50 (t, 2H), 3.08 (t, 2H), 2.94 (m, 4H), 2.80 (t, 2H), 2.68 (t. 2H), 2.28 (m, 2H), 1.96 (m, 6H), 1.66 (m, 4H).

SCHEME 6

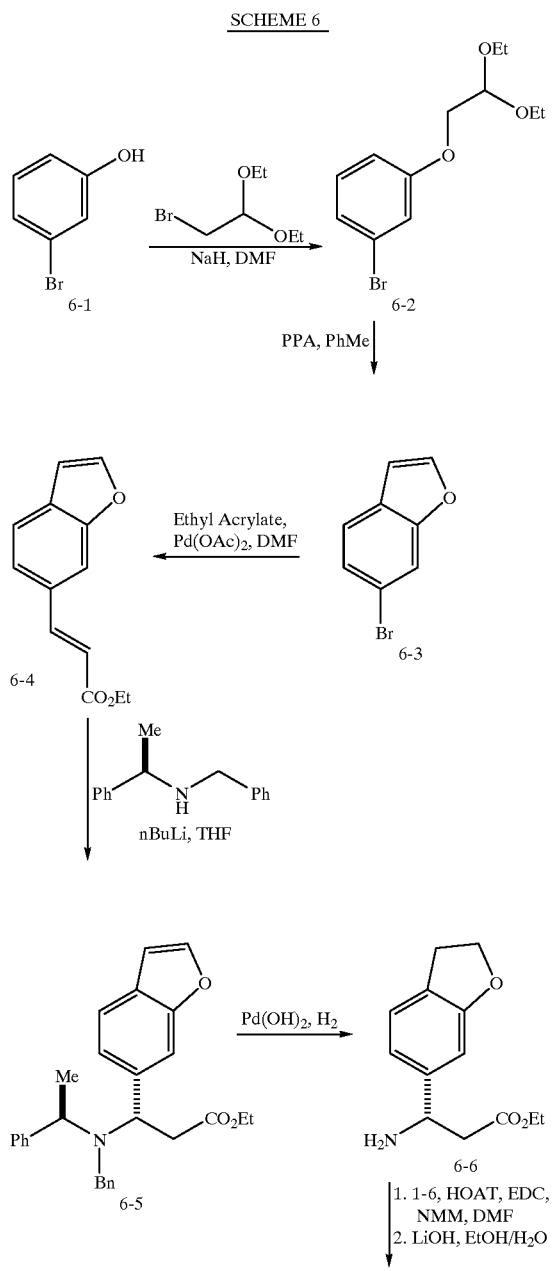

-continued

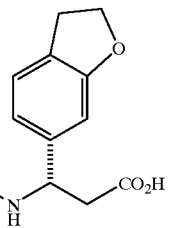

6-7

1-Bromo-3-(2,2-diethoxy-ethoxy)-benzene (6-2)

To a suspension of NaH (2.77 g, 115.6 mmol) in DMF (100 mL) at 0° C. was added a solution of 3-bromophenol 6-1 in DMF (40 mL) over 40 min. After the addition was complete, the solution was stirred for an additional 30 min. The solution was then treated with neat bromoacetaldehyde diethyl acetal (17.36 g, 115.6 mmol). The solution was heated at 100° C. for 8 h, cooled to room temperature, and extracted with Et₂O (3×200 mL). The combined organic extracts were washed with 10% aq. NaOH (100 mL) and brine (100 mL), dried over MgSO₄, filtered and concentrated to give 6-2 as a yellow oil.

TLC Rf=0.4 (10% ethyl acetate/hexanes).

¹H NMR (300 MHz, CHCl₃) δ 7.19–7.05 (m, 3H), 6.85 (d, 1H), 4.81 (t, 1H, J=6.8 Hz), 3.99 (d, 2H, J=6.8 Hz), 3.71 (m, 4H), 1.22 (t, 6H, J=7.1 Hz) ppm.

6-Bromo-benzofuran (6-3)

To a solution of the acetal 6-2 in toluene (200 mL) was added polyphosphoric acid (20 g). The biphasic mixture was heated to 100° C. and stirred at this temperature for 4 h. The mixture was cooled to room temperature, poured onto ice, and extracted with Et₂O (2×200 mL). The combined organic extracts were washed with saturated aq. NaHCO₃ and brine. The solution was dried over MgSO₄, filtered, and concentrated. The residue was purified by flash chromatography (100% hexanes) to give the product 6-3 as a yellow oil.

TLC Rf=0.3 (100% hexanes).

¹H NMR (300 MHz, CHCl₃) δ 7.68 (s, 1H ), 7.60 (d, 1H, J=2.1 Hz), 7.46 (d, 1H, J=8.4 Hz), 7.36 (dd, 1H, J=8.1, 1.5 Hz), 6.75 (dd, 1H, J=7.1, 0.9 Hz) ppm.

3-(Benzofuran-6-yl)-acrylic acid ethyl ester (6-4)

A mixture of the 6-bromo-benzofuran 6-3 (1.74 g, 8.79 mmol), ethyl acrylate (1.09 g, 10.98 mmol), Pd(OAc)₂ (0.099 g, 0.44 mmol), tri-o-tolylphosphine (0.268 g, 0.880 mmol), and sodium acetate (3.60 g, 43.9 mmol) in DMF (10 mL) was heated to 100° C. in a sealed tube for 4 h. The mixture was cooled to room temperature, diluted with water, and extracted with Et₂O (2×40 mL). The combined organic extracts were washed with brine (30 mL), dried over MgSO₄, filtered, and concentrated. The residue was purified by flash chromatography (10% ethyl acetate/hexanes) to give the ester 6-4 as an off-white solid.

TLC Rf=0.3 (10% ethyl acetate/hexanes).

¹H NMR (300 MHz, CHCl₃) δ 7.78 (d, 1H, J=15.9 Hz), 7.68 (d, 1H, J=2.4 Hz), 7.66 (s, 1H), 7.59 (d, 1H, J=8.4 Hz), 7.43 (dd, 1H, J=9.0, 1.5 Hz), 6.78 (m, 1H), 6.47 (d, 1H, J=15.9 Hz), 4.27 (q, 2H, J=7.2 Hz), 1.34 (t, 3H, J=7.2 Hz) ppm.

3(S)-(Benzofuran-6-yl)-3-[benzyl-(1(R)-phenyl-ethyl)-amino]-propionic acid ethyl ester (6-5)

A solution of N-benzyl-α-(R)-methylbenzylamine (1.32 g, 6.30 mmol) in THF (25 mL) at 0° C. was treated with n-BuLi (2.52 mL of a 2.5 M soln in hexanes). The resulting solution was stirred at 0° C. for 30 min and then cooled to −78° C. A solution of acrylate 6-4 (0.681 g, 3.15 mmol) in THF (5 mL) was added. After stirring for 15 min at −78° C., satd. aq. NH$_4$Cl soln (5 mL) was added and the cold bath removed. The mixture was warmed to room temperature, and extracted with Et$_2$O (2×40 mL). The combined organic extracts were washed with brine (30 mL), dried over MgSO$_4$, filtered, and concentrated. The residue was purified by flash chromatography (10% ethyl acetate/hexanes) to give the β-aminoester 6-5 as a yellow oil.

TLC Rf=0.8 (10% ethanol/dichloromethane).

$^1$H NMR (300 MHz, CHCl$_3$) δ 7.58 (m, 3H), 7.41 (m, 2H), 7.22 (m, 9H), 7.59 (s, 1H), 4.58 (m, 1H), 4.05 (m, 1H), 3.91 (q, 2H, J=7.1 Hz), 3.72 (m, 2H), 2.62 (m, 2H), 1.21 (d, 3H, J=7.2 Hz), 1.03 (t, 3H, J=7.1 Hz) ppm.

3(S)-Amino-3-(2,3-dihydro-benzofuran-6-yl)-propionic acid ethyl ester (6-6)

A mixture of the dibenzylamine 6-5 (1.19 g, 2.78 mmol) in EtOH/H$_2$O/AcOH (26 mL/3 mL/1.0 mL) was degassed with argon and treated with Pd(OH)$_2$ (1.19 g). The mixture was placed under 1 atm of H$_2$. After stirring for 18 h, the mixture was diluted with EtOAc, and filtered through celite. The filtrate was concentrated and the residue purified by flash chromatography (10% ethyl acetate/dichloromethane) to give the ester 6-6 as a white solid.

TLC Rf=0.25 (10% ethanol/dichloromethane).

$^1$H NMR (300 MHz, CDl$_3$OD) as the trifluoroacetate salt: δ 7.25 (d, 1H, J=8.1 Hz), 6.88 (m, 1H), 7.66 (s, 1H), 6.82 (s, 1H), 4.58 (m, 3H), 4.12 (m, 2H), 3.30 (m, 1H), 3.19 (m, 2H), 2.98 (m, 2H), 1.11 (t, 3H, J=7.2 Hz) ppm.

3(S)-(2,3-Dihydro-benzofuran-6-yl)-3-(5-(5,6,7,8-tetrahydro-[1,8]naphthyridin-2-yl)-pentanoylamino)-propionic acid (6-7)

A solution of the amine 6-6 (0.162 g, 0.596 mmol), acid 1-6 (0.183 g, 0.775 mmol), EDC (0.148 g, 0.775 mmol), N (0.156 g, 1.55 mmol), and HOAT (0.105 g, 0.775 mmol) in DMF (6 mL) was stirred at room temperature for 12 h. The solution was concentrated and the residue purified by preparative HPLC (gradient conditions: 95:05 to 50:50 H$_2$O/MeCN with 0.1% TFA) to give the ester (0.227 g) as a yellow oil. The ester was dissolved in a solution of EtOH/H$_2$O (6 mL of a 9:1 mixture) and treated with LiOH (0.065 g, 1.55 mmol). After stirring for 3 h, the solution was concentrated to a paste which was purified by preparative HPLC (gradient conditions: 95:05 to 50:50 H$_2$O/MeCN with 0.1% HCl) to give 6-7 as a white solid.

TLC R$_f$=0.24 (5% MeOH/CH$_2$Cl$_2$).

$^1$H NMR (300 MHz, CD$_3$OD) δ 7.57 (d, J=7.2 Hz, 1H), 7.12 (d, J=7.8 Hz, 1H), 6.79 (dd, J=1.5, 7.2 Hz, 1H), 6.70 (s, 1H), 6.58 (d, J=7.2 Hz, 1H), 5.27 (t, J=8.4 Hz, 1H), 4.50 (t, J=8.7 Hz, 2H), 3.49 (t, J=5.7 Hz, 2H), 3.14 (t, J=8.7 Hz, 2H), 2.81 (t, J=6.0 Hz, 2H), 2.76 (m, 2H), 2.66 (m, 2H), 2.26 (m, 2H), 1.94 (m, 2H), 1.64 (m, 4H) ppm.

SCHEME 7

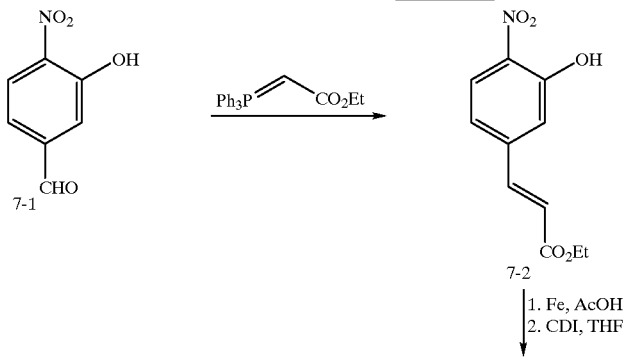

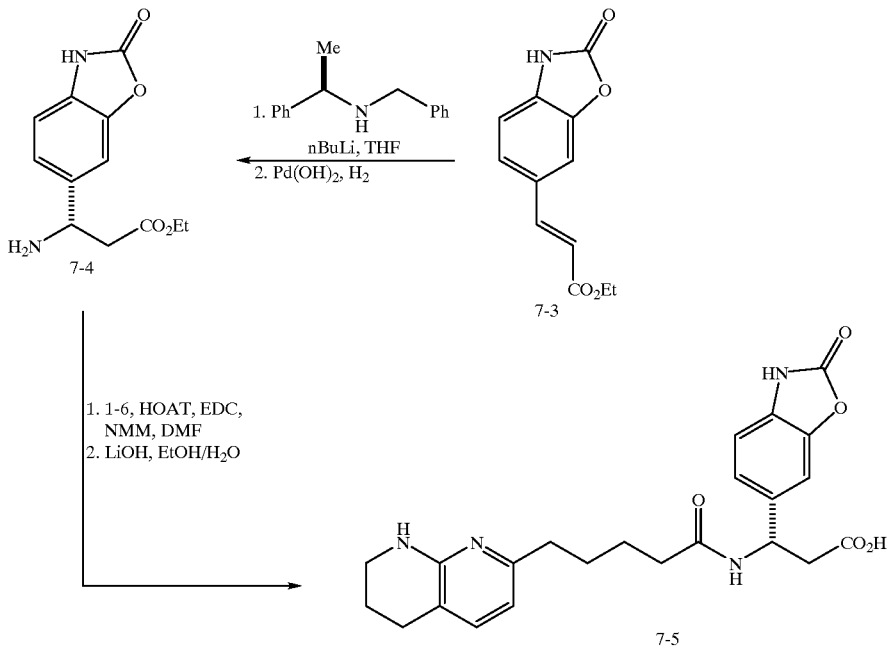

3-(3-Hydroxy-4-nitro-phenyl)-acrylic acid ethyl ester (7-2)

To a solution of aldehyde 7-1 (15.0 g, 98.0 mmol) in CH$_2$Cl$_2$ (300 mL) was slowly added carboethoxymethylenetriphenylphosphorane (34.1 g, 98.0 mmol). The orange solution was stirred for 12 h at ambient temperature. The solution was concentrated to a paste and purified by flash chromatography (10% EtOAc/CH$_2$Cl$_2$) to give 7-2 as a yellow solid.

TLC R$_f$=0.51 (30% ethyl acetate/hexanes).

$^1$H NMR (300 MHz, CD$_3$OD) δ 8.08 (d, J=8.4 Hz, 1H), 7.63 (d, J=16.2 Hz, 1H), 7.35 (d, J=1.5 Hz, 1H), 7.27 (dd, J=8.4, 1.5 Hz, 1H), 6.65 (d, J=15.9 Hz, 1H), 4.25 (q, J=7.2 Hz, 2H), 1.32 (t, J=6.9 Hz, 3H) ppm.

3-(2-Oxo-2,3-dihydro-benzooxazol-6-yl)-acrylic acid ethyl ester (7-3)

To a solution of the nitrophenol 7-2 (12.0 g, 57.4 mmol) in warm (70° C.) AcOH/H$_2$O (200 mL) was added iron dust (9.61 g, 172.2 mmol). The brown heterogeneous mixture was stirred for 30 min at 70–80° C. The mixture was filtered hot through celite, and the celite bed washed with EtOAc (2×200 mL). The filtrate was cautiously neutralized with satd. aq. NaHCO$_3$ (3×100 mL). The solution was dried over MgSO$_4$, filtered, and concentrated. The residue was purified by flash chromatography (5% MeOH in CH$_2$Cl$_2$) to give an orange solid (9.6 g, 81%). A portion of this solid (4.5 g, 21.7 mmol) was dissolved in THF (150 mL) and treated with 1,1-carbonyldiimidazole (3.87 g, 23.8 mmol), and the solution was stirred at ambient temperature for 24 h. The solution was diluted with EtOAc (100 mL) and washed with 10% HCl (50 mL) and brine (50 mL). The solution was dried over MgSO$_4$, filtered, and concentrated. The residue was purified by flash chromatography (5% MeOH in CH$_2$Cl$_2$) to give 7 as a yellow solid.

TLC R$_f$=0.49 (5% MeOH/CH$_2$Cl$_2$).

$^1$H NMR (300 MHz, CD$_3$OD) δ 7.77 (d, J=15.9 Hz, 1H), 7.55 (s, 1H), 7.41 (d, J=8.4 Hz, 1H), 7.09 (d, J=8.1 Hz, 1H), 6.47 (d, J=15.9 Hz, 1H), 4.22 (q, J=7.2 Hz, 2H), 1.31 (t, J=7.2 Hz, 3H) ppm.

3(S)-Amino-3-(2-oxo-2,3-dihydro-benzooxazol-6-yl)-propionic acid ethyl ester (7-4)

A solution of N-benzyl-α-(R)-methylbenzylamine (4.08 g, 19.3 mmol) in THF (120 mL) at 0° C. was treated with n-BuLi (7.72 mL of a 2.5 M soln in hexanes). The resulting solution was stirred at 0° C. for 30 min and then cooled to −78° C. A solution of acrylate 7-3 (1.5 g, 6.43 mmol) in THF (20 mL) was added. After stirring for 15 min at −78° C., satd. aq. NH$_4$Cl soln (25 mL) was added and the cold bath removed. The mixture was warmed to room temperature, and extracted with Et$_2$O (2×40 mL). The combined organic extracts were washed with brine (30 mL), dried over MgSO$_4$, filtered, and concentrated. The residue was purified by flash chromatography (30% ethyl acetate/hexanes) to give 2.74 g of the β-aminoester as a yellow oil. The aminoester was dissolved in EtOH/H$_2$O/AcOH (54 mL/4.8 mL/1.2 mL), degassed with argon, and treated with Pd(OH)$_2$ (2.74 g). The mixture was placed under 1 atm of H$_2$. After stirring for 18 h, the mixture was diluted with EtOAc and filtered through celite. The filtrate was concentrated to give 7-4 as an off-white solid.

TLC R$_f$=0.10 (5% MeOH/CH$_2$Cl$_2$).

$^1$H NMR (300 MHz, CD$_3$OD) δ 7.34 (s, 1H), 7.26 (dd, J=1.2, 8.1 Hz, 1H), 7.12 (d, J=8.1 Hz, 1H), 4.65 (t, J=7.2 Hz, 1H), 4.13 (q, J=6.9 Hz, 2H), 2.98 (m, 2H), 1.20 (t, J=7.2 Hz, 3H) ppm.

3(S)-(2-Oxo-2,3-dihydro-benzoxazol-6-yl)-3-(5-(5,6,7,8-tetrahydro-[1,8]naphthyridin-2-yl)-pentanoylamino)-propionic acid trifluoroacetate (7-5)

A solution of the amine 7-4 (0.196 g, 0.784 mmol), acid 1-6 (0.222 g, 0.941 mmol), EDC (0.189 g, 0.988 mmol), NMM (0.190 g, 1.88 mmol), and HOAT (0.134 g, 0.988 mmol) in DMF (6 mL) was stirred at room temperature for 12 h. The solution was concentrated and the residue purified by preparative HPLC (gradient conditions: 95:05 to 50:50 H₂O/MeCN with 0.1% TFA) to give the ester (0.144 g) as a yellow oil. The ester was dissolved in a solution of EtOH/H₂O (6 mL of a 9:1 mixture) and treated with LiOH (0.065 g, 1.55 mmol). After stiring for 3 h, the solution was concentrated to a paste which was purified by preparative HPLC (gradient conditions: 95:05 to 50:50 H₂O/MeCN with 0.1% TFA) to give 0.068 g (14% for two steps) of acid 7-5 as a white solid.

TLC R$_f$=0.11 (5% MeO/CH$_2$Cl$_2$).

$^1$H NMR (300 MHz, CD$_3$OD) δ .54 (d, J=8.7 Hz, 1H), 7.19 (s, 1H), 7.16 (d, J=8.4, 1H), 7.00 (d, J=8.1 Hz, 1H), 6.53 (d, J=7.5 Hz, 1H), 5.34 (t, J=6.9 Hz, 1H), 3.48 (t, J=5.7 Hz, 2H), 2.79 (m, 4H), 2.63 (m, 2H), 2.25 (m, 2H), 1.94 (m, 2H), 1.64 (m, 4H) ppm.

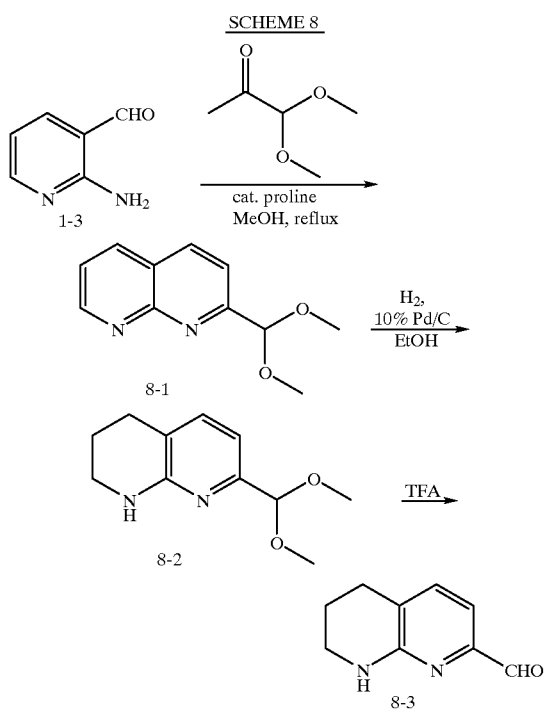

SCHEME 8

2-Dimethoxymethyl-[1,8]naphthyridine (8-1)

A mixture containing 1-3 (30 g, 0.245 mol), pyruvaldehyde dimethylacetal (87 g, 0.737 mol), and L-proline (7.0 g, 0.062 mol) in MeOH (300 mL) was refluxed under argon for 16 h. The cooled solution was filtered, evaporated and the residue dissolved in CH$_2$Cl$_2$ (500 mL) and washed with water and brine then dried and concentrated to a volume of ca. 100 mL. Hexane (300 mL) was added and the mixture was kept at 0° C. for 3 h, then filtered affording 8-1 as an off-white crystalline solid.

$^1$H NMR (300 MHz, CDCl$_3$) δ 9.14 (d, J=2.2 Hz, 1H); 8.26 (d, J=8.7 Hz, 1H); 8.21 (dd, J=8.7, 2.2 Hz, 1H); 7.8 (d, J=8.3 Hz, 1H); 7.5 (m, 1H); 5.48 (s, 1H); 3.53 (s, 6H).

2-Dimethoxymethyl-5,6,7,8-tetrahydro-[1,8] naphthyridine (8-2)

A solution of 8-1 (10 g, 0.049 mol) in ethanol (100 ml) was treated with 10% Pd on C (1.5 g) and the resulting mixture stirred under a H$_2$ filled balloon for 12.5 h. The catalyst was removed by filtration through celite and the solution concentrated to afford 8-2 as a yellow crystalline solid.

$^1$H NMR (300 MHz, CDCl$_3$) δ 7.18 (d, J=7.12 Hz, 1H); 6.71 (d, J=7.12 Hz, 1H); 5.18 (s, 1H); 4.96 (br, s, 1H); 3.43 (s, 6H); 3.4 (m, 2H); 2.65 (m, 2H); 1.91 (m, 2H).

5,6,7,8-tetrahydro-[1,8]naphthyridine-2-carboxaldehyde (8-3)

8-2 (10 g, 0.048 mol) was treated with trifluoroacetic acid (50 mL) and the resulting solution stirred under argon for 12.5 h. The TFA was removed at reduced pressure and the residue partitioned between sat. NaHCO$_3$ and CH$_2$Cl$_2$. The organic layer was dried, concentrated and passed through a 3 in. pad of silica gel (10% acetone/CH$_2$Cl$_2$) and concentrated to afford 8-3 as a yellow crystalline solid.

$^1$H NMR (300 MHz, CDCl$_3$) δ 9.80 (s, 1H); 7.31 (d, J=7.32 Hz, 1H); 7.16 (d, J=7.32 Hz, 1H); 5.31 (br, s, 1H); 3.48 (m, 2H); 2.81 (m, 2H); 1.94 (m, 2H).

SCHEME 9

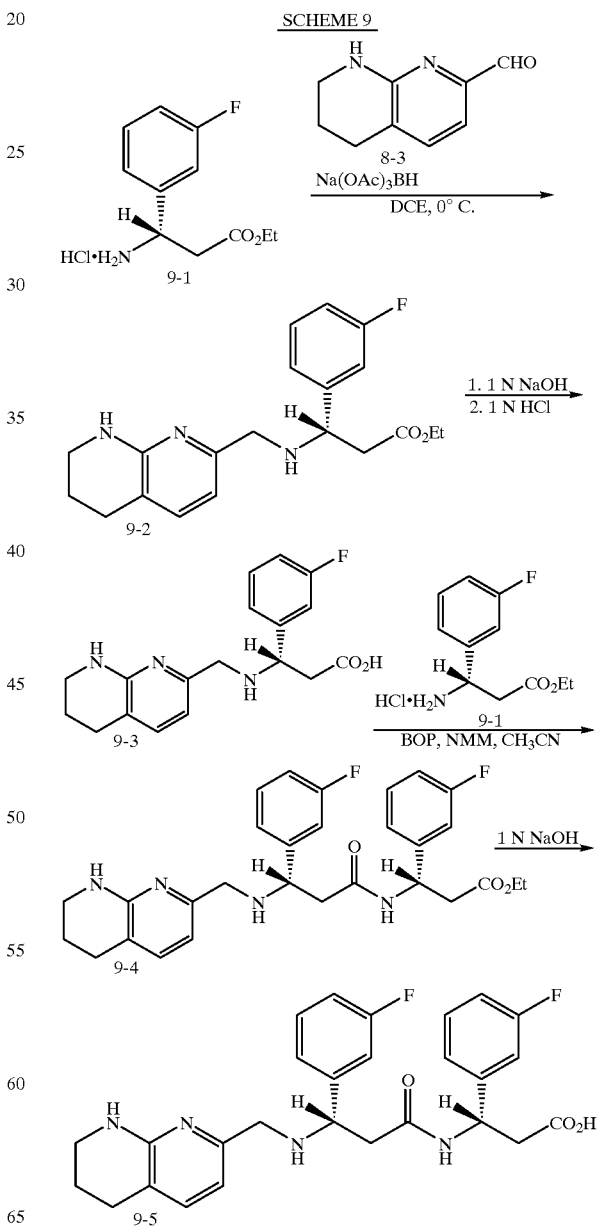

3(S)-Fluorophenyl-β-alanine ethyl ester hydrochloride (9-1)

The title compound 9-1 was prepared from 3-fluorobenzaldehyde as described for preparing 7-4 from 7-1.

$^1$H NMR (CD$_3$OD) δ 1.21 (3H, t), 3.0–3.2 (2H, m), 4.16 (2H, q), 4,76 (1H, t), 7.2–7.35 (3H, m), 7.5 (1H, m).

3(S)-(3-Fluorophenyl)-3-[(5,6,7,8-tetrahydro-[1,8] naphthyridin-2-ylmethyl)-amino]-propionic acid ethyl ester (9-2)

To a stirred solution of 8-3 (300 mg, 1.85 mmol), 9-1 (458 mg, 1.85 mmol) in dichloroethane (10 ml) at 0° C. was added sodium triacetoxyborohydride (570 mg, 2.59 mmol). After 1 hour, the reaction was diluted with EtOAc and then washed with 10% K$_2$CO$_3$, brine, and dried over MgSO$_4$. Following evaporative removal of the solvent, the residue was chromatographed (silica gel, 5% [10:1:1 ethanol/NH$_4$OH/H$_2$O]: 95% [70:25:5 chloroform/ethyl acetate/methanol]) to give ester 9-2 as a yellow solid.

TLC R$_f$=0.50 (silica, 5% [10:1:1 ethanol/NH$_4$O/H$_2$O]: 95% [70:25:5 chloroform/ethyl acetate/methanol])

$^1$H NMR (300 MHz, CDCl$_3$) δ 7.26 (m,1H), 7.07 (m, 3H), 6.95 (m, 1H), 6.37 (d, J=7.1 Hz, 1H), 4.76 (bs, 1H), 4.10 (m, 3H), 3.47 (d, J=7.1 Hz, 2H), 3.38 (m, 2H), 2.68 (m, 4H), 1.90 (m, 2H), 1.18 (t, J=7.1 Hz, 3H).

3(S)-(3-Fluorophenyl)-3-[(5,6,7,8-tetrahydro-[1,8] naphthyridin-2-ylmethyl)-amino]-propionic acid (9-3)

To a solution of ester 9-2 (450 mg, 1.26 mmol) in EtOH (3 mL) was added 1N NaOH (1.39 ml, 1.39 mmol). After stirring for 1 h, the solvents were evaporated and the residue was dissolved in 1N HCl (1.39 ml, 1.39 mmol). The solution was concentrated and then azeotroped with CH$_3$CN to give the acid 9-3 as a brown solid.

$^1$H NMR (300 MHz, CD$_3$OD) δ 7.45 (m,1H), 7.10 to 7.28 (m, 4H), 6.36 (d, J=7.3 Hz, 1H), 4.41 (m, 1H), 3.80 (s, 2H), 3.31 (m, 2H), 2.62 to 2.85 (m, 4H), 1.90 (m, 2H).

3(S)-(3-Fluorophenyl)-3-{3(S)-(3-fluorophenyl)3-[(5,6,7,8-tetrahydro-[1,8]naphthyridin-2-ylmethyl)-amino]-propionylamino}-propionic acid ethyl ester (94)

A mixture of acid 9-3 (235 mg, 0.6056 mmol), amine 9-1 (150 mg, 0.6056 mmol), BOP (350 mg, 0.7873 mmol) and NMM (0.333 mL, 3.03 mmol) in CH$_3$CN (5 mL) was stirred for 20 h. The mixture was diluted with ethyl acetate, washed with 10% K$_2$CO$_3$, brine, and dried over MgSO$_4$. Evaporative removal of the solvent gave 9-4 as a brown oil.

TLC R$_f$=0.15 (75:10:15 chloroform/ethyl acetate/MeOH).

$^1$H NMR (300 MHz, CDCl$_3$) δ 6.85 to 7.28 (m, 9H), 6.34 (d, J=7.3 Hz, 1H), 5.40 (m, 1H), 4.92 (s, 1H), 4.10 (m,3H), 3.52 (d,J=5.4 Hz, 2H), 3.38 (m, 2H,), 2.48 to 2.84 (m, 7H), 1.26 (t, J=7.1 Hz, 3H).

3(S)-(3-Fluorophenyl)-3-{3(S)-(3-fluorophenyl)-3-[(5,6,7,8-tetrahydro-[1,8]naphthyridin-2-ylmethyl)-amino]-propionylamino}-propionic acid bis (trifluoroacetate) (9-5)

To a solution of 9-4 (0.6056 mmol) in EtOH (3 mL) was added 1N NaOH (1.21 ml, 1.21 mmol). After stirring for 1 h, the solvents were evaporated and the residue was purified by Preparative HPLC (Waters Delta Pak C18: 100:0:0.1 to 5:95:0.1 H$_2$O/CH$_3$CN/TFA) to give 9-5 as a white solid.

$^1$H NMR (300 MHz, CD$_3$OD) δ 7.45 (d, J=6.8 Hz, 1H), 7.38(d, J=6.1 Hz, 1H), 7.29 (m, 1H), 6.94 to 7.18 (m, 6H), 6.51 (d, J=7.6 Hz, 1H), 5.43 (m,1H), 4.26 (m, 1H,), 3.81 (m, 2H), 3.49 (m, 2H), 2.69 to 2.90 (m, 4H), 1.92 (m, 2H).

SCHEME 10

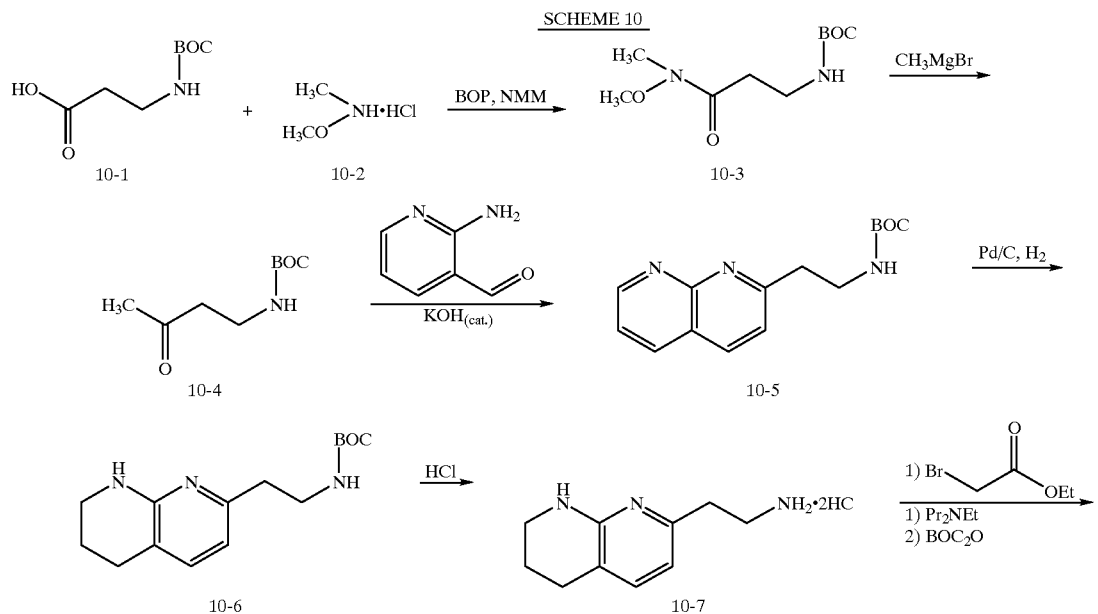

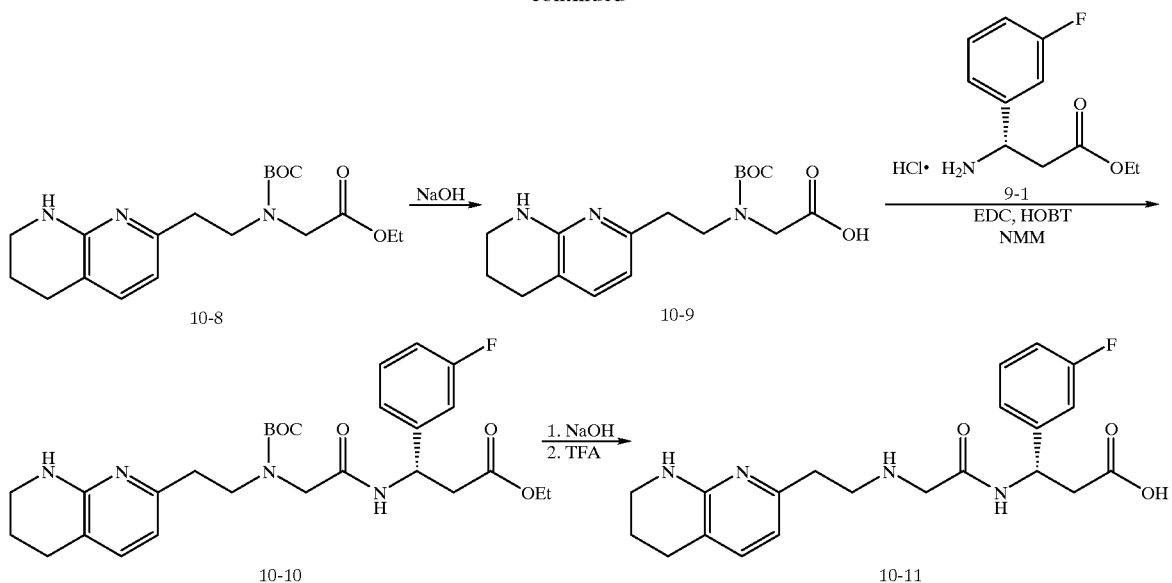

(3-Oxo-butyl)-carbamic acid tert-butyl ester (10-4)

A solution of BOC-beta-alanine (20 g, 105 mmol), 10-2 (10.3 g, 105 mmol), BOP reagent (46.5 g, 105 mmol), and N-methylmorpholine (46 mL, 420 mmol) in acetonitrile (500 mL) was stirred for 15 h. The reaction was diluted with EtOAc, washed with H$_2$O, 10% KHSO$_4$(aq.), sat. NaHCO$_3$, dried (MgSO$_4$) and concentrated to give crude [2-(methoxy-methyl-carbamoyl)-ethyl]-carbamic acid tert-butyl ester 10-3 as a yellow oil. TLC R$_f$=0.42 (silica, 20% EtOAc/hexanes). To a solution of this crude amide in THF (500 mL) at 0° C. was added CH$_3$MgBr (100 mL of 3M in ether, 300 mmol) over 30 minutes. After 2 h, 10% KHSO$_4$(aq.) was added, the mixture warmed to 25° C., and diluted with EtOAc. The organics were washed with sat. NaHCO$_3$, dried (MgSO$_4$) and concentrated. Flash chromatography (silica, 20% EtOAc/hexanes) gave 10-4 as a yellow oil.

TLC R$_f$=0.35 (silica, 20% EtOAc/hexanes).

$^1$H NMR (300 MHz, CDCl$_3$) δ 5.02 (br s, 1H), 3.32 (q, 2H, J=6.8 Hz), 2.66 (q, 2H, J=6Hz), 2.16 (s, 3H), 1.43 (s, 9H).

(2-[1,8]Naphthyridin-2-yl-ethyl)-carbamic acid tert-butyl ester (10-5)

A solution of 10-4 (10 g, 53.4 mmol), 2-amino-3-formylpyridine 1-3 (7.2 g, 64 mmol), 20% aq. KOH (1 mL), and ethanol (200 mL) was heated at reflux for 3 h. Evaporation of the solvents and flash chromatography (silica, 70 CHCl$_3$/28 EtOAc/2 MeOH) gave 10-5 as a solid.

TLC R$_f$=0.29 (silica, 70 CHCl$_3$/28 EtOAc/2 MeOH).

$^1$H NMR (300 MHz, CDCl$_3$) δ 9.11 (m, 1H), 8.16 (m, 2H), 7.45 (m, 2H), 5.27 (s, 1H), 3.75 (m, 2H), 3.27 (m, 2H), 1.40 (s, 9H).

[2-(5,6,7,8-Tetrahydro-[1,8]naphthyridin-2-yl)-ethyl]-carbamic acid tert-butyl ester (10-6)

A mixture of 10-5 (5.0 g, 20.4 mmol), 10% Pd/C (2.5 g), and EtOH (200 mL) was stirred under a balloon of hydrogen for 15 h. The mixture was filtered, and the filtrate concentrated to give 10-6 as a yellow oil.

TLC R$_f$=0.29 (silica, 70 CHCl$_3$/25 EtOAc/5 MeOH).

$^1$H NMR (300 MHz, CDCl$_3$) δ 7.16 (d, 1H, J=6.8 Hz), 6.48 (d, 1H, J=4.9 Hz), 5.12 (br s, 2H), 3.45 (m, 4H), 2.72 (m, 4H), 1.88 (m, 2H), 1.43 (s, 9H).

2-(5,6,7,8-Tetrahydro-[1,8]naphthyridin-2-yl)-ethylamine dihydrochloride (10-7)

Through a solution of 10-6 (4.0 g, 16 mmol) in EtOAc (200 mL) at 0° C. was bubbled a stream of HCl gas for 10 minutes. After an additional 30 minutes, the mixture was purged with argon for 1 h and then concentrated. The residue was dissolved in acetonitrile and concentrated to give 10-7 as a yellow solid.

$^1$H NMR (300 MHz, CD$_3$OD) δ 7.62 (d, 1H, J=7 Hz), 6.70 (d, 1H, J=7 Hz), 3.53 (t, 2H, J=6 Hz), 3.34 (m, 2H), 3.11 (m, 2H), 2.84 (m, 2H), 1.96 (m, 2H).

[tert-Butoxycarbonyl-[2-(5,6,7,8-tetrahydro-[1,8]naphthyridin-2-yl)-ethyl]-amino]-acetic acid ethyl ester (10-8)

To a solution of 10-7 (2.0 g, 7.8 mmol) and N,N-diisopropylethylamine (6.8 mL) in acetonitrile (50 mL) at 0° C. was added ethyl bromoacetate (0.975 mL, 8.6 mmol). The mixture was stirred at 50° C. for 15 h, then cooled to 25° C. and BOC$_2$O (1.7 g, 7.8 mmol) was added. After 1 h, the mixture was diluted with ethyl acetate, washed with sat. NaHCO$_3$, brine, dried (MgSO$_4$) and concentrated. Flash chromatography (silica, 50–60% EtOAc/hexanes) gave 10-8 as a colorless oil.

TLC R$_f$=0.5 (silica, EtOAc).

$^1$H NMR (300 MHz, CDCl$_3$) mixture of rotamers: δ7.04 (d, 2H, J=7 Hz), 6.35 (dd, 1H, J=7 Hz), 4.73 (br s, 1H), 4.16 (m, 2H), 3.89 (s, 1H), 3.82 (s, 1H), 3.56 (m, 2H), 3.39 (m, 2H), 2.76 (m, 4H), 1.90 (m, 2H), 1.44 (m, 9H), 1.25 (m, 3H).

3-(2-[tert-Butoxycarbonyl-[2-(5,6,7,8-tetrahydro-[1,8]naphthyridin-2-yl)-ethyl]-amino]-acetylamino)-3 (S)-(3-fluorophenyl)-propionic acid ethyl ester (10-10)

To a solution of 10-8 (0.8 g (2.20 mmol) in EtOH (10 mL) was added 1N NaOH (2.4 mL, 2.4 mmol) and the mixture stirred for 1 h. The solvents were evaporated, and the residue was dissolved in 1N HCl, evaporated, and additionally evaporated from acetonitrile to give crude [tert-butoxycarbonyl-[2-(5,6,7,8-tetrahydro-[1,8]naphthyridin-2-yl)-ethyl]-amino]-acetic acid 10-9 (0.820 g, 95%). To a mixture of the crude 10-9 in acetonitrile (2 mL) was added 3-amino-3-(S)[3-fluorophenyl]propionic acid (9-1) (0.1 g, 0.404 mmol), EDC (93 mg, 1.2 eq), HOBT (55 mg, 1 eq), and NMM (0.222 mL, 5 eq). After stirring for 12 h, the mixture was diluted with ethyl acetate, washed with water, sat. NaHCO$_3$, brine, dried (MgSO$_4$) and concentrated to give 10-10 as a yellow oil.

TLC R$_f$=0.18 (silica, 70: CHCl$_3$/25: EtOAc/5: MeOH).

$^1$H NMR (300 MHz, CDCl$_3$) mixture of rotamers: δ9.52 (m, 0.5 H), 9.07 (m, 0.5 H), 7.38–6.91 (m, 6H), 6.36 (m, 1H), 5.48 (m, 1H), 4.67 (m, 1H), 4.10 (m, 3H), 3.82 (m, 1H), 3.66 (m, 1H), 3.44 (m, 1H), 3.21 (m, 1H), 2.82 (m, 1H), 2.63 (m, 1H), 1.78 (m, 4H), 1.51–1.13 (m, 12H).

3(S)-(3-Fluorophenyl)-3-{2-[2-(5,6,7,8-tetrahydro-[1,8]naphthyridin-2-yl)-ethylamino]-acetylamino}-propionic acid (10-11)

To a solution of 10-10 (0.23 g (0.404 mmol) in EtOH (2 mL) was added 1N NaOH (0.6 mL, 0.6 mmol) and the mixture stirred for 1 h. The solvents were evaporated, and the residue was dissolved in dichloromethane (2 mL), and TFA (2 mL) added. After 1 h, the solution was concentrated from toluene. Flash chromatography (silica, 20:10:1:1 to 10:10:1:1 EtOAc/EtOH/NH$_4$OH/H$_2$O) gave 10-11 as a white solid.

TLC R$_f$=0.21 (silica, 10:10:1:1 EtOAc/EtOH/NH$_4$OH/H$_2$O).

$^1$H NMR (300 MHz, CD$_3$OD): δ7.28 (m, 1H), 7.13 (m, 3H), 6.91 (m, 1H), 6.38 (d, 1H, J=7 Hz), 5.37 (m, 1H), 3.36 (m, 4H), 2.82 (m, 2H), 2.68 (m, 4H), 2.61 (m, 2H), 1.87 (m, 2H).

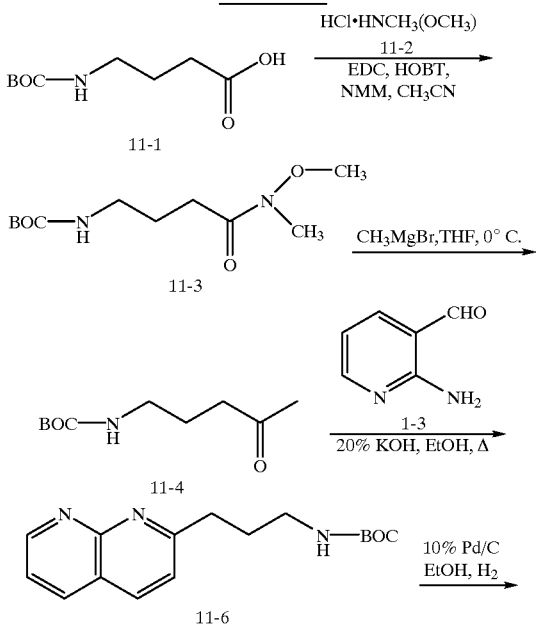

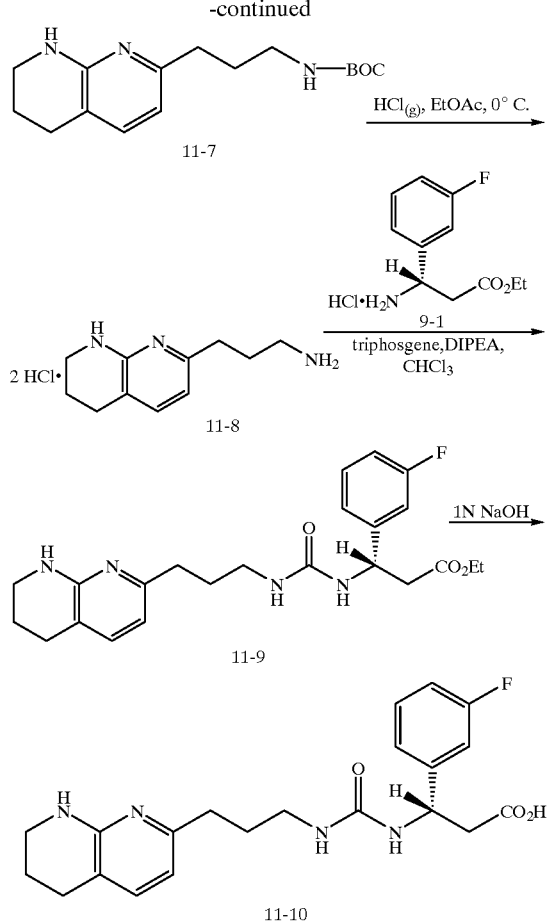

[3-(N-Methoxy-N-methyl-carbamoyl)-propyl] carbamic acid tert-butyl ester (11-3)

A mixture of 11-1 (10 g, 49.2 mmol), 11-2 (4.8 mg, 49.2 mmol), EDC (9.40 g, 49.2 mmol), HOBT (6.6 g, 49.2 mmol) and NMM (2.7 mL, 246 mmol) in CH$_3$CN (200 mL) was stirred for 20 h. The reaction was concentrated. The residue was dissolved in ethyl acetate, washed with H$_2$O, 10% KHSO$_4$, sat. NaHCO$_3$, brine, and dried over MgSO$_4$. Evaporative removal of the solvent gave 11-3 as a colorless oil.

TLC R$_f$=0.15 (50% ethyl acetate hexanes).

$^1$H NMR (300 MHz, CDCl$_3$) δ 4.96 (bs,1H), 3.55 (s, 3H), 3.46 (m, 5H), 2.48 (t, J=7.3 Hz, 2H), 1.83 (m, 2H), 1.46 (s, 9H).

(4-Oxo-pentyl)carbamic acid tert-butyl ester (11-4)

To a stirred solution of 11-3 (10.0 g, 40.5 mmol) and THF (200 ml) at 0° C. was added methylmagnesium bromide (27.0 ml, 91.0 mmol; 3M in ether) dropwise over 20 minutes. After 2.0 hours, 10% KHSO$_4$ was added slowly. The mixture was extracted with EtOAc. The organic portion was washed with sat. NaHCO$_3$, brine, and dried over MgSO$_4$. Evaporative removal of the solvent gave 11-4 as a colorless oil.

TLC R$_f$=0.53 (silica, 40% EtOAc/hexanes)

$^1$H NMR (300 MHz, CDCl$_3$) δ 4.62 (bs,1H), 3.13 (m, 2H), 2.49 (t, J=7.1 Hz, 2H), 2.16 (s, 3H), 1.78 (m, 2H), 1.44 (s, 9H).

(3-[1,8]Naphthyridin-2-yl)-N-Boc-propylamine (11-6)

A mixture of 11-4 (5.0 g, 24.8 mmol), 1-3, 2-amino-3-formylpyridine (3.6 g, 29.8 mmol) and 20% KOH (1 ml) in absolute ethanol (100 mL) was heated at reflux for 8 h. Following evaporative removal of the solvent, the residue was chromatographed (silica gel, 70:28:2 chloroform/ethyl acetate/methanol) to give 11-6 as a yellow oil.

TLC $R_f$=0.40 (silica, 70:20:10 chloroform/ethyl acetate/methanol)

$^1$H NMR (300 MHz, CDCl$_3$) δ 9.08 (m, 1H), 8.16 (d, J=8.1 Hz, 1H), 8.10 (d, J=8.1 Hz, 1H), 7.41 (m, 2H), 4.82 (bs, 1H), 3.21 (m, 2H), 3.06 (m, 2H), 2.12 (m,2H), 1.43 (s, 9H).

3-(5,6,7,8-Tetrahydro-[1,8]naphthyridin-2-yl)-N-Boc-propylamine (11-7)

A mixture of 11-6 (4.0 g, 13.9 mmol) and 10% Pd/carbon (4.0 g) in EtOH (100 mL) was stirred under a balloon of hydrogen for 4 h. Following filtration and evaporative removal of the solvent, the residue was chromatographed (silica gel, 70:28:2 chloroform/ethyl acetate/methanol) to give 11-7 as a white solid.

TLC $R_f$=0.30 (silica, 70:25:5 chloroform/ethyl acetate/methanol)

$^1$H NMR (300 MHz, CDCl$_3$) δ 7.05 (d, J=7.3 Hz, 1H), 6.34 (d, J=7.3 Hz, 1H), 5.48 (s, 1H), 4.79 (s, 1H), 3.37 (m, 2H), 3.15 (m, 2H), 2.69 (t, J=6.3 Hz, 2H), 2.59 (t, J=7.3 Hz, 2H), 1.88 (m, 4H), 1.44 (s, 9H).

3-(5,6,7,8-Tetrahydro-[1,8]naphthyridin-2-yl)-propylamine dihydrochloride (11-8)

HCl gas was rapidly bubbled through a solution of 11-7 (2.5 g, 8.6 mmol) in EtOAc (100 ml) at 0° C. for 10 minutes. After 30 minutes, the solution was purged with argon for 30 minutes. The solution was concentrated and then azeotroped with CH$_3$CN to give the amine 11-8 as a yellow solid.

$^1$H NMR (300 MHz, CD$_3$OD) δ 7.61 (d, J=7.3 Hz, 1H), 6.67 (d, J=7.3 Hz, 1H), 3.52 (t, J=5.6 Hz, 2H), 2.99 (m, 2H), 2.83 (m, 4H), 2.08 (m, 2H),1.96 (m, 2H).

3(S)-(3-Fluorophenyl)-3-{3-[3-(5,6,7,8-tetrahydro-[1,8]naphthyridin-2-yl)-propyl]-ureido}-propionic acid ethyl ester (11-9)

To a stirred solution of 9-1 (100 mg, 0.4037 mmol), DIPEA (0.380 ml, 2.42 mmol) and CHCl$_3$ (5 ml) was added triphosgene (42 mg, 0.1413 mmol). After 30 minutes, 11-8 was added. After 1 hour, the reaction was diluted with EtOAc and then washed with sat NaHCO$_3$, brine, and dried over MgSO$_4$. Evaporative removal of the solvent gave 11-9 as a yellow solid.

TLC $R_f$=0.37 (silica, 75:10:15 chloroform/ethyl acetate/methanol)

$^1$H NMR (300 MHz, CDCl$_3$) δ 7.22 (m,2H), 7.11 (m, 2H), 6.99 (m, 1H), 6.36 (d, J=7.1 Hz, 1H), 6.00 (m, 1H), 5.78 (m, 1H), 5.27 (m, 1H), 4.08 (m, 2H), 3.66 (m, 1H), 3.44 (m, 2H), 3.21 (m, 2H), 2.63 to 2.91 (m, 6H), 1.92 (m, 2H), 1.85 (m, 2H), 1.18 (t, J=7.1 Hz,3H).

3(S)-(3-Fluorophenyl)-3-{([3-(5,6,7,8-tetrahydro-[1,8]naphthyridin-2-yl)-propyl]-ureido}-propionic acid (11-10)

To a solution of 11-9 (0.4037 mmol) in EtOH (3 mL) was added 1N NaOH (0.600 ml, 0.600 mmol). After stirring for 2 h, the solvents were evaporated and the residue was chromatographed (silica gel, 20:10:1:1 to 10:10:1:1 ethyl acetate/EtOH/water/NH$_4$OH) to give 11-10 as a white solid.

TLC Rf=0.21 (10:10:1:1 ethyl acetate/EtOH/water/NH$_4$O).

$^1$H NMR (300 MHz, CD$_3$OD) δ 7.41 (d, J=7.3 Hz, 1H), 7.31 (m, 1H), 7.17 (d, J=7.5 Hz, 1H), 7.09 (d, J=10.2 Hz, 1H), 6.95 (m,1H), 6.49 (d,J=7.3 Hz, 1H), 5.23 (m, 1H,), 3.45 (t, J=5.6 Hz, 2H), 3.04 (m, 1H), 2.46 to 2.79 (m, 7H), 1.76 to 1.96 (m,4H).

SCHEME 12

3-(5-(5,6,7,8-Tetrahydro-[1,8]naphthyridin-2-yl)-pentanoylamino)-propionic acid (12-2)

A mixture of acid 1-6 (10.8 mg, 0.04 mmol), EDC (7.7 mg, 0.04 mmol), HOBT (5.4 mg, 0.04 mmol) and NMM (0.026 mL, 0.24 mmol) in DMF (1 mL) was agitated until clear solution. After 30 minutes, amine 12-1 was added. The solution was agitated for one minute and then let stand for 18 h. The solution was diluted with ethyl acetate, washed with sat. NaHCO$_3$ and H$_2$O. Following evaporative removal of the solvent, the residue was dissolved in 90:10 TFA/H2O (1 ml). After 2 h, the solvents were evaporated to give acid 12-2.

TLC Rf=0.49 (silica, 10:10:1:1 ethyl acetate/EtOH (NH$_4$OH/H$_2$O).

Mass calculated for C$_{16}$H$_{23}$N$_3$O$_3$=305, found M+1=306

SCHEME 13
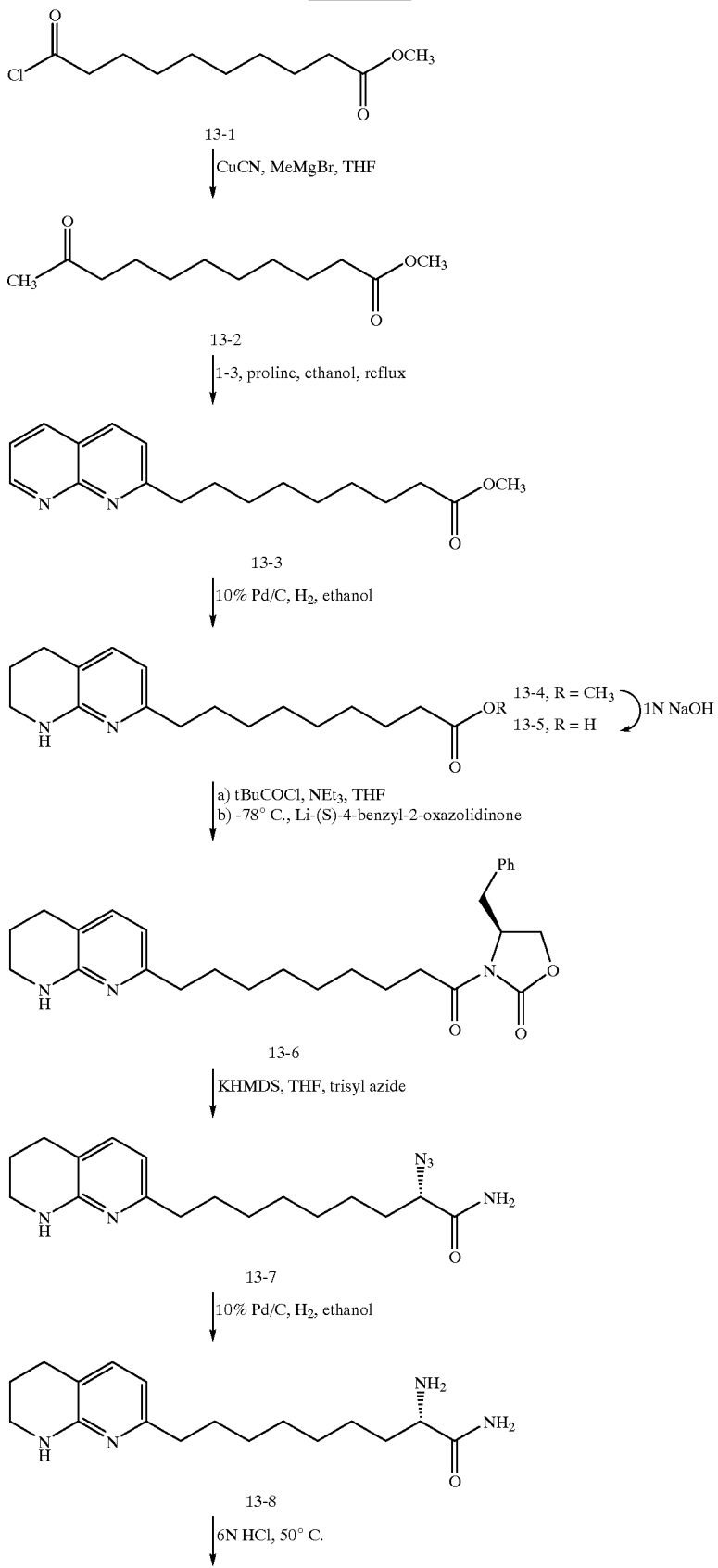

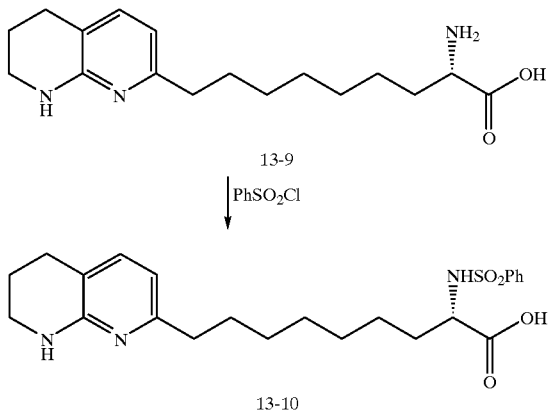

10-Oxo-undecanoic methyl ester (13-2)

To a suspension of CuCN (5.0 g, 56 mmol) in THF (200 mL) at −78° C. was added MeMgBr (17.4 mL, 3M solution in THF) dropwise. After addition was complete, the reaction misture was warmed to −15° C. for 5 min, recooled to −78° C. and then treated dropwise with 13-1 (9.3 mL, 42 mmol). The reaction mixture was then warmed to −10° C. for 1.5 h and then quenched with 90% sat. NH$_4$Cl (300 mL) and EtOAc (400 mL). The organic phase was washed with sat. NH$_4$Cl, sat. NaHCO$_3$, and brine, dried (MgSO$_4$), and concentrated to furnish 13-2 as a pale yellow oil.

TLC Rf=0.52 (silica, 30% EtOAc/hexanes);

$^1$H NMR (300 MHz, CDCl$_3$) δ 3.65 (s, 3H), 2.43 (t, J=7 Hz, 2H), 2.30 (t, J=7 Hz, 2H), 2.13 (s, 3H), 1.60 (m, 4H), 1.29 (m, 8H).

9-([1,8]-Naphthyridin-2-yl)-nonanoic acid methyl ester (13-3)

A mixture of 13-2 (9.2 g, 43 mmol), 1-3 (5.3 g, 43 mmol), proline (2.5 g, 22 mmol), and ethanol (215 mL) was heated to reflux for 20 h. The cooled reaction mixture was concentrated and the residue purified by flash chromatography (silica, EtOAc) to give 13-3 as a yellow oil.

TLC Rf=0.37 (silica, EtOAc);

$^1$H NMR (300 MHz, CDCl$_3$) δ 9.08 (m, 1H), 8.16 (m, 1H), 8.10 (d, J=8 Hz, 1H), 7.44 (m, 1H), 7.40 (d, J=8 Hz, 1H), 3.68 (s, 3H), 3.04 (m, 2H), 2.30 (m, 2H), 1.90 (m, 2H), 1.60 (m, 2H), 1.50–1.20 (m, 8H).

9-(5,6,7,8-Tetrahydro-[1,8]naphthyridin-2-yl)-nonanoic acid methyl ester (13-4)

A mixture of 13-3 (8.5 g, 28 mmol), 10% Pd/C (1.7 g), and ethanol (140 mL) was stirred under a hydrogen atmosphere for 20 h. The reaction mixture was then filtered through a celite pad and concentrated to give 13-4 as a pale yellow oil.

TLC Rf=0.45 (silica, EtOAc);

$^1$H NMR (300 MHz, CDCl$_3$) δ 7.06 (d, J=8 Hz, 1H), 6.33 (d, J=8 Hz, 1H), 3.68 (s, 3H), 3.40 (m, 2H), 2.70 (m, 2H), 2.53 (m, 2H), 2.30 (m, 2H), 1.90 (m, 2H), 1.60 (m, 4H), 1.50–1.20 (m, 8H).

9-(5,6,7,8-Tetrahydro-[1,8]-naphthyridin-2-yl)-nonanoic acid(13-5)

A solution of 13-4 (8.2 g, 27 mmol), 1N NaOH (30 mL), and methanol (134 mL) was stirred at 0° C. for 72 h. The methanol was evaporated and the residue dissolved in H$_2$O (30 mL) and neutralized with 1N HCl to effect a white precipitate. The solid was collected by filtration and dried at 50° C. to give 13 -5.

TLC Rf=0.53 (silica, 20:1:1 ethanol/NH$_4$OH/H$_2$O);

$^1$H NMR (300 MHz, CD$_3$OD) δ 7.36 (d, J=8 Hz, 1H), 6.46 (d, J=8 Hz, 1H), 3.44 (m, 2H), 2.75 (m, 2H), 2.60 (m, 2H), 2.22 (m, 2H), 1.90 (m, 2H), 1.62 (m, 4H), 1.40–1.30 (m, 8H).

9-(5,6,7,8-Tetrahydro-[1,8]naphthyridin-2-yl)-nonanoyl [(−)-4-benzyl-2-oxazolidinone (13-6)

To a suspension of 13-5 (5.6 g, 19 mmol), THF (97 mL), and NEt$_3$ (3.2 mL, 23 mmol) at −78° C. was added trimethylacetyl chloride (2.6 mL, 21 mmol) dropwise. After addition was complete, the reaction mixture was warmed to 0° C. for 2 h then recooled to −78° C. and treated with lithium (S)-(−)-4-benzyl-2-oxazolidinone (18 mL, 29 mmol; 1.6M solution in THF). The reaction mixture was then warmed to 0° C. for 1 h and poured into EtOAc (300 mL) and sat. NaHCO$_3$ (30 mL). The organic phase was washed with sat. NaHCO$_3$, H$_2$O, and brine, dried (MgSO$_4$), and concentrated. Flash chromatography (silica, EtOAc) gave 13-6 as an oil.

TLC Rf=0.31 (silica, EtOAc);

$^1$H NMR (300 MHz, CDCl$_3$) δ 7.40–7.15 (m, 5H), 7.03 (d, J=8 Hz, 1H), 6.33 (d, J=8 Hz, 1H), 4.67 (m, 1H), 4.13 (m, 2H), 3.40 (m, 2H), 3.29 (1H), 3.00–2.73 (m, 3H), 2.68 (m, 2H), 2.53 (m, 2H), 1.90 (m, 2H), 1.63 (m, 4H), 1.40–1.30 (m, 8H).

2-Azido-9-(5,6,7,8-tetrahydro-[1,8]naphthyridin-2-yl)-nonanoyl amide (13-7)

To a solution of 13-6 (19.4 mmol) and THF (65 mL) at −78° C. was added KHMDS (89 mL, 44.6 mmol; 0.5 M solution in THF). After 30 min., trisyl azide (9.0 g, 29 mmol) in THF (50 mL) was added via cannula. After 3 min., the reaction was quenched with AcOH (6.9 mL) dropwise followed by removal of the cooling bath. After 20 h, the reaction mixture was poured into EtOAc (300 mL) and sat. NaHCO$_3$ (60 mL). The organic phase was washed with sat. NaHCO$_3$, H$_2$O, and brine, dried (MgSO$_4$), and concentrated. Flash chromatography (silica, 5–20% isopropanol/EtOAc) gave 13-7 as an oil.

TLC Rf=0.47 (silica, 5% NH$_3$ sat. ethanol/EtOAc);

$^1$H NMR (300 MHz, CDCl$_3$) δ 7.03 (d, J=8 Hz, 1H), 6.34 (d, J=8 Hz, 1H), 6.30 (bs, 1H), 5.77 (bs, 1H), 4.82 (bs, 1H), 3.97 (m, 1H), 3.40 (m, 2H), 2.68 (m, 2H), 2.50 (m, 2H), 2.00–1.20 (m, 14H).

2-Amino-9-(5,6,7,8-tetrahydro-[1,8]naphthyridin-2-yl)-nonanoyl amide (13-8)

A mixture of 13-7 (0.4 g, 1.2 mmol), ethanol (6 mL), and 10% Pd/C (0.4 g) was stirred under a hydrogen atmosphere for 30 min. The reaction mixture was then filtered through a celite pad and concentrated to give 13-8 as an oil.

TLC Rf=0.82 (silica, 10:1:1 ethanol/NH$_4$OH/H$_2$O);

$^1$H NMR (300 MHz, CDCl$_3$) δ 7.10 (m, 1H), 7.08 (d, J=8 Hz, 1H), 6.35 (d, J=8 Hz, 1H), 6.30 (bs, 1H), 5.48 (bs, 1H), 5.13 (bs, 1H), 3.40 (m, 4H), 2.70 (m, 2H), 2.53 (m, 2H), 2.00–1.20 (m, 14H).

2-Amino-9-(5,6,7,8-tetrahydro-[1,8]naphthyridin-2-yl)-nonanoic acid (13-9)

A solution of 13-8 (0.3 g, 1.0 mmol) and 6N HCl (10 mL) was heated at 50° C. for 20 h. The reaction was then treated with conc. HCl (1 mL) and heated for an additional 5 h. The reaction mixture was then concentrated, the residue dissolved in H$_2$O and neutralized with conc. NH$_4$OH to form a precipitate. Filtration followed by drying under vacuum at 40° C. gave 13-9 as a gray solid.

TLC Rf=0.90 (silica, 10:1:1 ethanol/NH$_4$OH/H$_2$O);

$^1$H NMR (300 MHz, D$_2$O) δ 7.00 (d, J=8 Hz, 1H), 6.37 (d, J=8 Hz, 1H), 3.10 (m, 2H), 3.00 (m, 1H), 2.45 (m, 2H), 2.27 (m, 2H), 1.63 (m, 2H), 1.30 (m, 4H), 1.05 (m, 8H).

2(S)-(Benzenesulfonylamino)-9-(5,6,7,8-tetrahydro-[1,8]naphthyridin-2-yl)-nonanoic acid (13-10)

A solution of 13-9 (0.27 g, 0.88 mmol) in H$_2$O/dioxane (2:1, 4.4 mL) was cooled to 0° C. and then treated dropwise with 1N NaOH to attained a pH of 10.5. The reaction mixture was then treated with with PhSOCl (0.23 g, 1.3 mmol) in dioxane (750 μL) while maintaining a pH of 10.5 by adding 1N NaOH. After 15 min, the pH was adjusted to 7 with 1N HCl to effect a white precipitate. The precipitate was collected by filtration and triturated with EtOAc and then ether to give 13-10 as a colorless solid.

$^1$H NMR (300 MHz, D$_2$O) δ 7.50 (m, 2H), 7.10 (m, 3H), 6.95 (d, J=8 Hz, 1H), 6.20 (d, J=8 Hz, 1H), 4.60 (m, 1H), 3.04 (m, 2H), 2.40 (m, 2H), 2.23 (m, 2H), 1.63 (m, 2H), 1.20 (m, 4H), 0.08 (m, 8H).

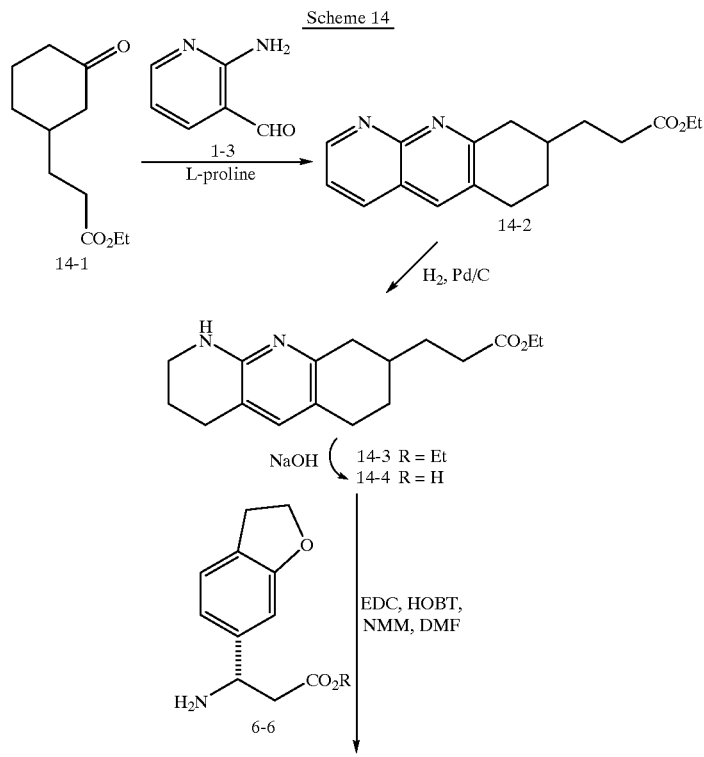

Scheme 14

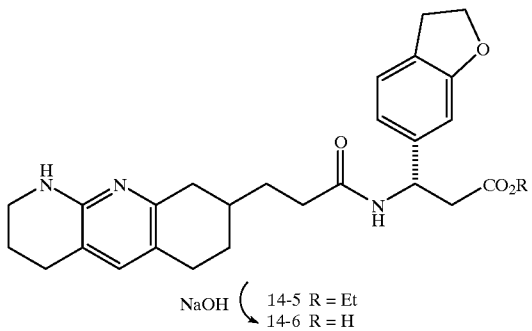

3-(6,7,8,9-tetrahydro-benzo[b]-[1,8]naphthyridin-8-yl)-propionic acid ethyl ester (14-2)

A solution of 2-amino-pyridine-3-carbaldehyde (1-3) (0.244 g, 2.0 mmol) and 3-(3-oxo-cyclohexyl)-propionic acid ethyl ester (14-1) (0.245 g, 2.00 mmol; for prep., see J. R. Wiseman et.al., *J. Am. Chem. Soc.*, 1970, 92, 956–962) in ethanol (10 mL) was treated with L-proline (0.230 g, 2.00 mmol) and heated at reflux for 12 h. The solution was cooled to ambient temperature and concentrated. The residue was purified by flash chromatography (10% acetone in $CH_2Cl_2$) to give 14-2.

$^1$H NMR (300 MHz, $CDCl_3$) δ 9.02–9.00 (m, 1H), 8.09–8.06 (m, 1H), 7.84–7.37 (m, 1H), 7.27(s, 1H), 4.15 (q, J=7.2 Hz, 2H), 3.43–3.35 (m, 1H), 3.31–2.98 (m, 4H), 2.84–2.75 (dd, J=11, 16 Hz, 1H), 2.47 (t, J=7.8 Hz, 2H), 2.10–1.77 (m, 3H), 1.57–1.51 (m, 1H), 1.27 (t, J=7.2 Hz, 3H) ppm.

3-(1,2,3,4,6,7,8,9-octahydro-benzo[b]-[1,8]naphthyridin-8-yl)-propionic acid ethyl ester (14-3)

A mixture of 14-2 (0.298 g, 1.05 mmol) and Pd on carbon (0.060 g) in ethanol (10 mL) was placed under 1 atm of $H_2$ and stirred for 12 h. The solution was concentrated. The residue was purified by flash chromatography (5% MeOH in $CH_2Cl_2$) to give 14-3.

$^1$H NMR (300 MHz, $CDCl_3$) δ 6.88 (s, 1H), 4.70 (s, 1H), 4.13 (q, J=7.2 Hz, 2H), 3.37 (m, 2H), 2.80–2.58 (m, 5 H), 2.42–2.27 (m, 3H), 1.93–1.65 (m, 6H), 1.25 (t, J=7.2 Hz, 3H) ppm.

3-(1,2,3,4,6,7,8,9-octahydro-benzo[b][1,8]naphthyridin-8-yl)-propionic acid (14-4)

A solution of 14-3 (0.180 g, 0.62 mmol) and NaOH (1.24 mL of a 1N soln, 1.24 mmol) in $THF/H_2O$ (5 mL./5 mL) was stirred at room temperature for 12 h. The solution was concentrated. The residue was triturated with $Et_2O$ to give 14-4.

$^1$H NMR (300 MHz, $CD_3OD$) δ 6.91 (s, 1H), 2.75–2.58 (m, 6H), 2.29–2.15 (m, 5H), 1.96–1.62 (m, 5H), 1.34–1.27 (m, 1H) ppm.

3(S)-(2,3-Dihydro-benzofuran-6-yl)-3-(3-(1,2,3,4,6,7,8,9-octahydro-benzo[b][1,8]naphthyridin-8-yl)-propionylamino)-propionic acid ethyl ester (14-5)

A solution of 14-4 (0.110 g, 0.39 mmol), β-aminoester 6-6 (0.106 g 0.39 mmol), EDC (0.075 g, 0.39 mmol), HOBT (0.053 g, 0.39 mmol) and N-methylmorpholine (0.164 mL, 1.17 mmol) in degassed DMF (5 mL) was stirred at room temperature for 12 h. The solution was concentrated. The residue was purified by flash chromatography to give 14-5.

$^1$H NMR (300 MHz, $CD_3OD$) δ 7.19 (s, 1H), 7.12–7.07 (m, 1H), 6.79–6.76 (m, $^1$H), 6.69 (br s, 1H), 5.49–5.26 (m, 1H), 4.52–4.45 (m, 2H), 4.05 (q, J=7.0 Hz, 2H), 3.41–3.38 (m, 2H), 3.15–3.10 (t, J=8.5 Hz, 2H), 2.78–2.68 (m, 3H), 3.59 (m, 2H), 2.37–2.21 (m, 5H), 1.61–1.70 (m, 5H), 1.38 (m, 1H), 1.18–1.14 (t, J=7.0 Hz, 3H) ppm.

3(S)-(2,3-Dihydro-benzofuran-6-yl)-3-(3-(1,2,3,4,6,7,8,9-octahydro-benzo[b][1,8]naphthyridin-8-yl)-propionylamino)-propionic acid (14-6)

A solution of 14-5 (0.050 g, 0.105 mmol) and aqueous 1N NaOH (0.210 mL, 0.210 mmol) was stirred at room temperature for 3 h. The solution was concentrated. The residue was triturated with $Et_2O$ and the white solid collected by to give 14-6.

$^1$H NMR (300 MHz, $CD_3OD$) δ 7.41 (s, 1H), 7.12–7.10 (d, J=7.3 Hz, 1H), 6.80–6.78 (d, J=7.3 Hz, 1H), 6.70 (s, 1H), 5.38 (m, 1H), 4.43 (m, 2H), 3.43 (m, 4H), 3.17 (m, 2H), 2.78 (m, 3H), 2.61 (m, 2H), 2.36 (m, 3H), 1.95 (m, 2H), 1.77 (m, 4H), 1.40 (m, 1H) ppm.

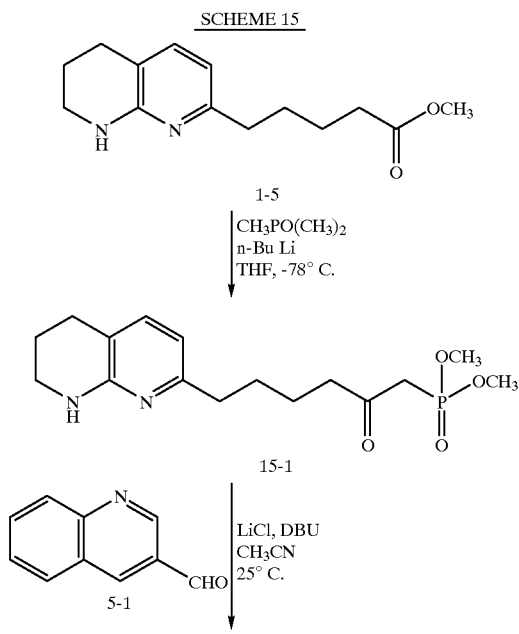

SCHEME 15

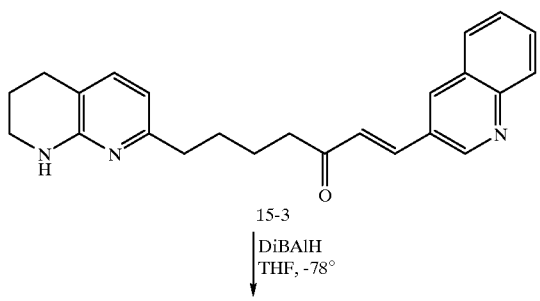

15-3

DiBAlH
THF, -78°

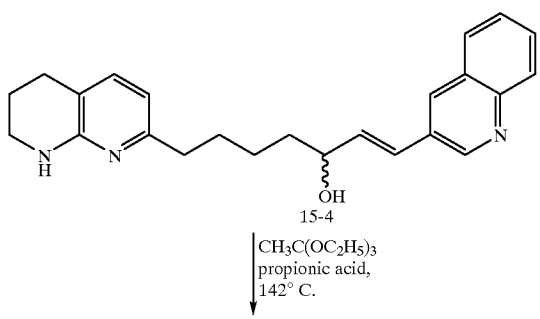

15-4

CH₃C(OC₂H₅)₃
propionic acid,
142° C.

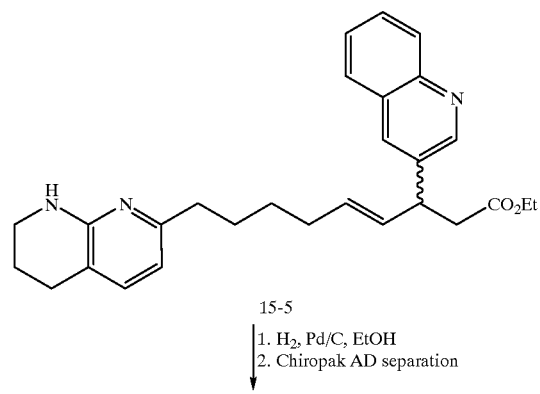

15-5

1. H₂, Pd/C, EtOH
2. Chiropak AD separation

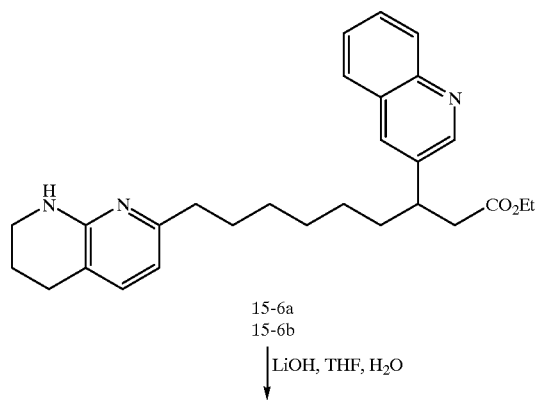

15-6a
15-6b

LiOH, THF, H₂O

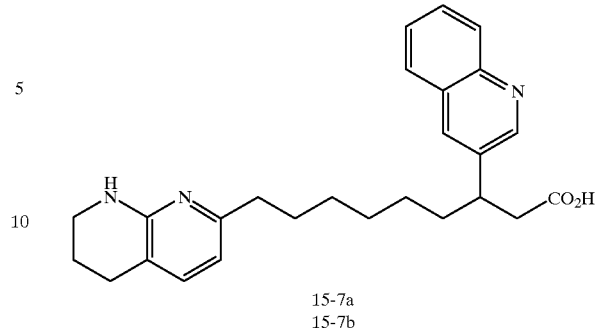

15-7a
15-7b

2-Oxo-6-(5,6,7,8-tetrahydro-[1,8]-naphthyridin-2-yl)-hexyl-phosphonic acid dimethyl ester (15-1)

A solution of dimethyl methylphosphonate (13.20 g, 106.5 mmol) in anhydrous THF (165 mL) was cooled to −78° and treated dropwise with 2.5 M n-BuLi (42.3 mL). After stirring at −78° for 45 min, a solution of ester 1-5 (6.6 g, 26.6 mmol) in THF (35 mL) was added dropwise and the resulting solution stirred for 30 min −78°, quenched with sat. NH₄Cl (100 mL), then extracted with ethyl acetate (3×150 mL). The combined organic extracts were dried (MgSO₄), filtered, and concentrated to afford a yellow oil. Chromatography on silica gel (5% MeOH/CH₂Cl₂) afforded 15-1 as a yellow oil.

$R_f$ (silica, 5% MeOH/CH₂Cl₂)=0.20.

¹H NMR (300 MHz, CDCl₃) δ 7.05 (d, J=7.3 Hz, 1H), 6.34 (d, J=7.32 Hz, 1H), 4.80 (br, s, 1H), 3.81 (s, 3H), 3.75 (s, 3H), 3.4 (m, 2H), 3.08 (d, J=22.7 Hz), 2.7-2.5 (m, 6 H), 1.91 (m, 2H), 1.68 (m, 4H).

3-(Quinolin-3-yl)-7-(5,6,7,8-tetrahydro-[1,8]-naphthyridin-2-yl)-(E)-hept-1-en-3-one (15-3)

Ketophosphonate 15-1 (2.0 g, 5.9 mmol), anhydrous LiCl (250 mg, 5.9 mmol), and 3-quinoline-carboxaldehyde 5-1 (0.77 g, 4.9 mmol) in anhydrous acetonitrile (60 mL) were treated with DBU (0.73 mL, 5.88 mmol) and the resulting suspension stirred at room temperature for 1 h. The solvent was removed at reduced pressure and the resulting residue partitioned between brine and methylene chloride. The organic layer was removed, dried, and concentrated to afford a yellow solid which was recrystallized from ethyl acetate/hexanes to afford 15-3 as an off-white solid.

$R_f$ (silica, 5% MeOH/CH₂Cl₂)=0.45.

¹H NMR (300 MHz, CDCl₃) δ 9.05 (d, J=1.8 Hz, 1H), 8.23 (d, J=1.8 Hz, 1H), 8.05(d, J=8.5 Hz, 1H), 7.87 (d, J=7.5 Hz, 1H), 7.81 (t, J=7.5 Hz, 1H), 7.68 (d, J=16 Hz, 1H), 7.58 (t, J=7.5 Hz, 1H), 7.05 (d, J=7.3 Hz, 1H), 6.95 (d, J=16 Hz, 1H), 6.34 (d, J=7.32 Hz, 1H), 4.80 (br, s, 1H), 3.4 (m, 2H), 2.7-2.5 (m, 6 H), 1.91 (m, 2H), 1.68 (m, 4H).

3-(Quinolin-3-yl)-7-(5,6,7,8-tetrahydro-[1,8]-naphthyridin-2-yl)-(E)-hept-1-en-3-ol (15-4)

A solution of 15-3 (1.33 g, 3.58 mmol) in anhydrous THF (150 mL) was cooled to −78°, then treated dropwise with i-Bu$_2$AlH (10.75 mL, 10.75 mmol). The resulting solution was stirred at −78° for 20 min., then quenched with ethyl acetate (20 mL), warmed to room temperature, treated with 1 M potassium sodium tartrate (25 mL) and stirred for 4 h. The mixture was extracted with ethyl acetate (2×150 mL) dried, filtered and evaporated to afford 15-4 as an off-white solid.

R$_f$ (silica, 10% MeOH/CH$_2$Cl$_2$)=0.10.

$^1$H NMR (300 MHz, CDCl$_3$) δ 9.05 (d, J=1.8 Hz, 1H), 8.15 (d, J=8.5 Hz, 1H), 8.13 (d, J=1.8 Hz, 1H), 7.87 (d, J=7.5 Hz, 1H), 7.81 (t, J=7.5 Hz, 1H), 7.58 (t, J=7.5 Hz, 1H), 7.05 (d, J=7.3 Hz, 1H), 6.86 (d, J=16 Hz, 1H), 6.45 (dd, J=16,6.5 Hz, 1H) 6.37 (d, J=7.32 Hz, 1H), 4.80 (br, s, 1H), 4.4 (m, 1H) 3.4 (m, 2H),2.75 (m, 2 H), 2.62 (m, 2H), 1.91 (m, 2H), 1.72 (m, 4H) 1.55(m, 2 H).

3-(Quinolin-3-yl)-9-(5,6,7,8-tetrahydro-[1,8]-naphthyridin-2-yl)-(E)-non-4-enoic acid ethyl ester (15-5)

A solution of the allylic alcohol 15-4 (1.4 g, 3.75 mmol) in triethyl orthoacetate (64 mL) was treated with propionic acid (0.014 mL, 0.19 mmol) and refluxed for 1.5 h. The cooled mixture was treated with a solution of 1:1 sat. brine/1N HCl (50 mL), then extracted with CH$_2$Cl$_2$ (3×125 mL). The pooled organic extracts were washed with sat. NaHCO$_3$, dried, filtered and evaporated. Chromatography on silica gel (5% MeOH/CH$_2$Cl$_2$) afforded 15-5 as a yellow glass.

R$_f$ (silica, 5% MeOH/CH$_2$Cl$_2$)=0.25.

$^1$H NMR (300 MHz, CDCl$_3$) δ 9.08 (br, s, 1H), 8.92 (d, J=1.8 Hz, 1H), 8.15 (d, J=8.5 Hz, 1H), 7.96 (d, J=1.8 Hz, 1H), 7.82 (d, J=7.5 Hz, 1H), 7.71 (t, J=7.5 Hz, 1H), 7.54 (t, J=7.5 Hz, 1H), 7.05 (d, J=7.3 Hz, 1H), 6.25 (d, J=7.32 Hz, 1H), 5.6 (m, 2H), 4.05 (m, 2H), 4.05 (m, 1H), 3.40 (m, 2H), 2.75 (m, 2 H), 2.65 (m, 2H),2.58 (m, 2H), 2.01 (m, 2H), 1.91 (m, 2H), 1.65 (m, 2H), 1.45(m, 2 H), 1.08 (t, J=7.5 Hz, 3H).

3(S or R)-(Quinolin-3-yl)-9-(5,6,7,8-tetrahydro-[1,8]-naphthyridin-2-yl)-nonanoic acid ethyl ester & 3 (R or S)-(quinolin-3-yl)-9-(5,6,7,8-tetrahydro-[1,8]-naphthyridin-2-yl)-nonanoic acid ethyl ester (15-6a & 15-6b)

A solution of 15-5 (1.0 g, 2.25 mmol) in EtOH was treated with 10% Pd on C (200 mg) and the mixture stirred under a hydrogen gas-filled balloon for 3 hours. The catalyst was removed by filtration through celite and the solvent evaporated to afford the mixture of enantiomers as a colorless glass.

R$_f$ (silica, 5% MeOH/CH$_2$Cl$_2$)=0.25.

$^1$H NMR (300 MHz, CDCl$_3$) δ 8.81 (d, J=1.8 Hz, 1H), 8.60 (br, s, 1H), 8.15 (d, J=8.5 Hz, 1H), 7.96 (d, J=1.8 Hz, 1H), 7.82 (d, J=7.5 Hz, 1H), 7.71 (t, J=7.5 Hz, 1H), 7.54 (t, J=7.5 Hz, 1H), 7.15 (d, J=7.3 Hz, 1H), 6.25 (d, J=7.32 Hz, 1H), 4.05 (m, 2H), 3.40 (m, 2H), 3.25 (m, 1H), 2.75 (m, 2 H), 2.65 (m, 2H),2.58 (m, 2H), 1.87 (m, 2H), 1.81 (m, 2H), 1.75 (m, 2H), 1.25(m, 4 H), 1.08 (t, J=7.5 Hz, 3H).

The enantiomers 15-6a and 15-6b were separated on a 250×20 mm Chiralpak AD column (flow=8 mL/min, A:B= 50:50) (A=0.1% diethylamine/hexane, B=1-propanol). R$_t$ (15-6a)=18.8 min, (15-6b)=20.9 min.

3(R or S)-(Quinolin-3-yl)-9-(5,6,7,8-tetrahydro-[1,8]-naphthyridin-2-yl)-nonanoic acid (15-7a)

A solution of 15-6a (193 mg, 0.43 mmol) in 50% aqueous THF (10 mL) was treated with solid LiOH (27 mg, 0.65 mmol), and the mixture stirred at room temperature for 18 h, then neutralized with 1N HCl. Chromatography on silica gel (50% A:50% EtOAc) (A=20:1:1 EtOH:NH$_4$OH:H$_2$O) afforded 15-7a as a colorless glass.

R$_f$ (silica, 50% A: EtOAc)=0.45

$^1$H NMR (300 MHz, CDCl$_3$) δ 10.2 (br, s, 1H), 8.92 (d, J=1.8 Hz, 1H), 8.15 (d, J=8.5 Hz, 1H), 7.96 (d, J=1.8 Hz, 1H), 7.82 (d, J=7.5 Hz, 1H), 7.71 (t, J=7.5 Hz, 1H), 7.54 (t, J=7.5 Hz, 1H), 7.05 (d, J=7.3 Hz, 1H), 6.25 (d, J=7.32 Hz, 1H), 5.6 (m, 2H), 3.56 (m, 1H), 3.40 (m, 2H), 2.75 (m, 2 H), 2.65 (m, 2H),2.58 (m, 2H), 2.01 (m, 2H), 1.91 (m, 2H), 1.65 (m, 2H), 1.45(m, 2 H).

3(S or R)-(Quinolin-3-yl)-9-(5,6,7,8-tetrahydro-[1,8]-naphthyridin-2-yl)-nonanoic acid (15-7b)

This compound was prepared from 15-6b as described above for 15-7a.

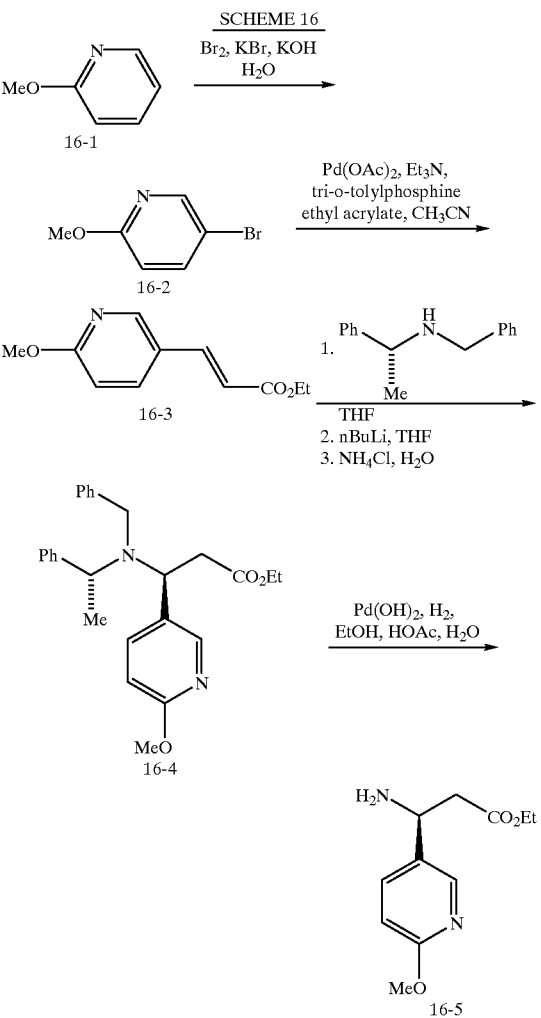

SCHEME 16

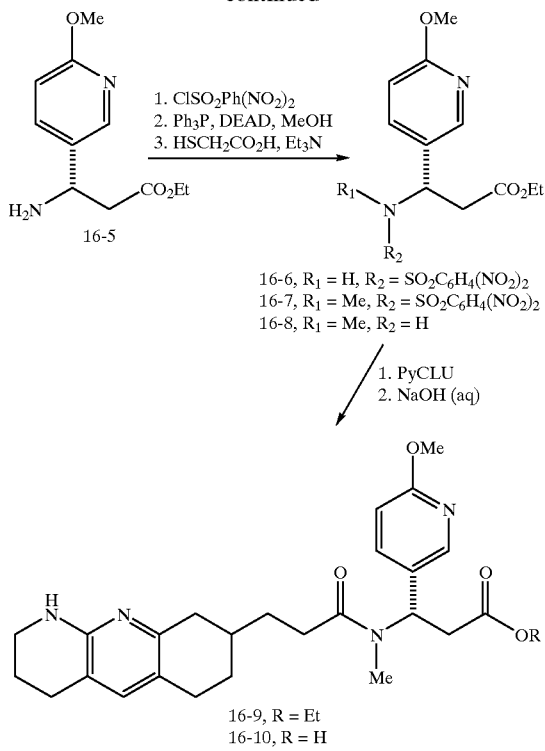

5-Bromo-2-methoxypyridine (16-2)

To a solution of KOH (4.2 g, 0.075 mol) in water (750 mL) was added 2-methoxypyridine 16-1 (16.4 g, 0.15 mol) followed by a dropwise addition of bromine (24 g, 0.15 mol) in 1N aqueous KBr (750 mL) and the resulting solution was stirred at room temperature for 5 hr. Solid NaHCO$_3$ was added until basic and the solution was extracted with CHCl$_3$ (3×500 mL). The organic layer was washed with 10% NaHSO$_3$, then brine, dried over Na$_2$SO$_4$, filtered, and the solvent removed in vacuo. The resulting dark brown oil was predominantly the desired compound 16-2 and was used as such in the next step.

$^1$H NMR (300 MHz, CDCl$_3$) δ 3.91 (3H, s), 6.66 (1H, d), 7.62 (1H, dd), 8.20 (1H, d).

Ethyl 3-(6-methoxypyridin-3-yl)acrylate (16-3)

A solution of the 5-bromo-2-methoxypyridine 16-2 (74.3 g, 0.4 mol), ethyl acrylate (150 mL, 1.4 mol), triethylamine (150 mL, 1.08 mol), palladium acetate (10 g, 0.045 mol) and tri-o-tolylphosphine (20 g, 0.066 mol) in 100 mL acetonitrile was degassed with argon for 10 minutes. The mixture was heated at 90° C. for 12 hr, then the volatiles were removed in vacuo. Toluene (300 mL) was added and the mixture concentrated again. Diethyl ether (300 mL) was added and the mixture filtered through a pad of silica gel eluting with 800 mL of diethyl ether. After removal of the diethyl ether, the residue was chromatographed on silica gel eluting with EtOAc/hexane, 1:19 then 1:14 then 1:9 to give 16-3 as a yellow solid.

1H NMR (300 MHz, CDCl3) δ 1.34 (3H, t), 3.97 (3H, s), 4.26 (2H, q), 6.34 (1H, d),6.76 (1H, d), 7.63 (1H, d), 7.77 (1H, dd),8.27 (1H, d).

N-Benzyl-(R)-α-methylbenzyl-3(S)-(6-methoxypyridin-3-yl)-β-alanine ethyl ester (16-4)

To a solution of N-benzyl-(R)-α-methylbenzylamine (97.5 g, 462 mmol) in THF (750 mL) at 0° C. was added n-butyllithium (2.5M in hexanes; 178.5 mL, 446 mmol). The dark violet solution was stirred at 0° C. for 20 minutes, cooled to −78° C., and the ester 16-3 (63.7 g, 308 mmol) in THF (250 mL) was added over 60 minutes. The resulting solution was stirred at −78° C. for 1 hr, then cannulated into saturated NH$_4$Cl and extracted with EtOAc, washed with water then brine, dried and concentrated in vacuo to give an oil. Column chromatography (silica gel; hexane/EtOAc 9:1 then 4:1) gave 16-4 as an oil contaminated with N-benzyl-(R)-α-methylbenzylamine. This oil was taken up in 5% AcOH in water and extracted with diethyl ether (4×). The organic layers were dried over MgSO$_4$ and the solvent removed to give the title compound 16-4.

$^1$H NMR (300 MHz, CDCl$_3$) δ 1.08 (3H, t), 1.27 (3H, d), 2.52 (1H, dd), 2.62 (1H, dd), 3.66 (1H, d), 3.70 (1H, d), 3.93 (3H, s), 3.95 (2H, m), 4.41 (1H, dd), 6.74 (1H, d), 7.15-7.45 (10H, m), 7.64 (1H, dd), 8.15 (1H, d).

3(S)-(6-methoxypyridin-3-yl)-β-alanine ethyl ester (16-5)

To a degassed (argon) solution of the ester 16-4 (70 g) in EtOH (250 mL), HOAc (25 mL) and water (2 mL) was added 20% Pd(OH)$_2$ on carbon. The mixture was placed under hydrogen gas using a balloon and the resulting mixture was stirred for 24 hr. After filtration through celite (washing with EtOAc), the solvent was removed in vacuo to afford a waxy solid. This was dissolved in 200 mL water and extracted with diethyl ether (2×200 mL). The aqueous layer was then treated with solid K$_2$CO$_3$ until fully saturated and extracted with EtOAc (4×200 mL). After drying over MgSO$_4$, the solvent was removed in vacuo to give the title compound 16-5 as an oil which solidified in the freezer.

$^1$H NMR (300 MHz, CDCl$_3$) δ 1.23 (3H, t), 2.61 (1H, dd), 2.68 (1H, dd), 3.92 (3H, s), 4.15 (2H, q), 4.41 (1H, dd), 6.93 (1H, d), 7.62 (1H, dd), 8.13 (1H, d).

3(S)-(6-Methoxy-pyridin-3-yl)-3-(4-nitro-benzenesulfonylamino)-propionic acid ethyl ester (16-6)

A solution of aminoester 16-5 (3.0 g, 13.0 mmol) in CH$_2$Cl$_2$ (20 mL) was treated with aq NaHCO$_3$ (4.4 g in 20 mL H$_2$O). 2,4-Dinitrobenzenesulfonyl chloride (4.3 g, 16 mmol) was added and the reaction mixture stirred for 12 h. The solution was extracted with CH$_2$Cl$_2$ (3×40 mL) and the combined organic solutions washed with satd aq NaHCO$_3$ (40 mL) and brine (40 mL). The solution was dried over MgSO$_4$, filtered, and concentrated. The residue was purified by flash chromatography (97:3 CH$_2$Cl$_2$/MeOH) to give the desired product 16-6.

TLC Rf=0.45 (5% methanol/dichloromethane).

3(S)-(6-Methoxy-pyridin-3-yl)-3-[methyl-(4-nitro-benzenesulfonyl)-amino]-propionicacid ethyl ester (16-7)

Triphenylphosphine (3.9 g, 15 mmol) was added to a solution of sulfonamide 16-6 (4.5 g, 10 mmol) in THF (30 mL). To this solution was added a solution of diethyl azodicarboxylate (2.4 mL, 15 mmol) in THF/MeOH (10 mL/2.02 mL). A vigorous exotherm occurred and the reaction was stirred overnight at room temperature. The dark mixture was concentrated. The dark oily residue was purified by flash chromatography (40% EtOAc/hexanes) to give the desired product 16-7.

TLC Rf=0.37 (40% ethyl acetate/hexanes).

3(S)-(6-Methoxy-pyridin-3-yl)-3-methylamino-propionic acid ethyl ester (16-8)

A solution of sulfonamide 16-7 (4.7 gm, 10 mmol) in CH$_2$Cl$_2$ (50 mL) was treated with triethylamine (2.8 mL, 20 mmol) and mercaptoacetic acid (1.04 mL, 15 mmol). The reaction was stirred for 90 min at room temperature. The green solution was diluted with EtOAc (500 mL) and washed with satd aq NaHCO$_3$ (150 mL), water (3×100 mL), and brine (3×100 mL). The solution was dried over Na$_2$SO$_4$, filtered and concentrated to a black oil. The residue was purified by flash chromatography (5% MeOH/CH$_2$Cl$_2$) to give the desired product 16-8.

$^1$HNMR (300 MHz, CDCl$_3$) δ 8.07 (d, J=2.4 Hz, 1H), 7.57 (m, 1H), 6.73 (m, 1H), 4.11 (q, J=7.3 Hz, 2H), 3.93 (s, 3H), 2.72 (m, 2H), 1.21 (t, J=7.3 Hz, 3H) ppm 3(S)-(6-Methoxy-pyridin-3-yl)-3-[N-methyl-3-(1,2, 3,4,6,7,8,9-octahydrobenzo[b][1,8]naphthyridin-8-yl-propionyl)-amino]-propionic acid ethyl ester (16-9)

Racemic tricyclic ester 14-3 was resolved by chiral HPLC (Chiracel OD column; 25×2 mm eluting with 95:5 hexanes/isopropanol/0.1% diethylamine at a flow rate of 8 ml/min: R$_T$=6.48 and 7.21 min.) The more polar enantiomer was hydrolyzed to give carboxylate 14-4a. A solution of 14-4a (0.175 gm, 0.62 mmol) in DMF/1N HCl (10 mL/0.62 mL) was treated with disopropylethylamine (0.540, 3.10 mmol), aminoester 16-8 (0.162 gm, 0.68 mmol) in DMF (2 mL), and PyCLU (0.224 gm, 0.62 mmol). After stirring for 12 h at room temperature, the solution was concentrated and the residue partitioned between EtOAc (20 mL) and satd aq NaHCO$_3$ (20 mL). The organic solution was washed with brine (10 mL), dried over sodium sulfate, filtered and concentrated. The residue was purified by flash chromatography (5% MeOH/CH$_2$Cl$_2$) to give the desired amide 16-9. TLC Rf=0.28 (5% methanol/dichloromethane).

3(S)-(6-Methoxy-pyridin-3-yl)-3-[N-methyl-3-(1,2, 3,4,6,7,8,9-octahydrobenzo[b][1,8]naphthyridin-8-yl-propionyl)-amino]propionic acid (16-10)

A solution of ester 16-9 (0.133 gm, 0.28 mmol) in MeOH/THF/H$_2$O (1 mL/1 mL/1 mL) was treated with 1N aq NaOH (0.56 mL, 0.56 mmol). After stirring for 12 h at room temperature, the mixture was concentrated and the resulting aqueous residue neutralized with 1N aq HCl (0.56 mL). The residue was purified by flash chromatography (15% EtOH/15% EtOAc/1% aq NH$_4$OH/1% H$_2$O) to give the desired acid 16-10.

$^1$HNMR (300 MHz, CDCl$_3$) mixture of rotamers: δ 8.07 (m, 1H), 7.62 (m, 1H), 7.35 (m, 1H), 6.80 (m, 1H), 6.38 (m, 1H), 4.90 (s, 3H), 3.45 (m, 1H), 3.78 (m, 13H), 1.93 (m, 7H), 1.42 (m, 1H) ppm.

SCHEME 17

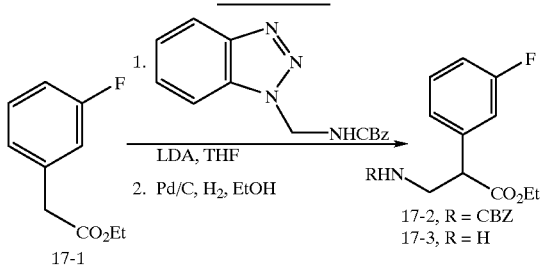

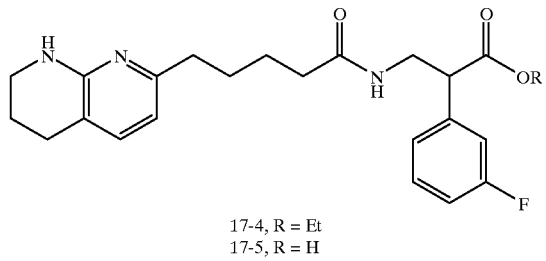

17-4, R = Et
17-5, R = H

3-Benzyloxycarbonylamino-2-(3-fluoro-phenyl)-propionic acid ethyl ester (17-2)

To a stirred solution of LDA (9.43 mL of a 2.0 M solution in THF, 18.86 mmol) in THF (80 mL) at −78° C. was added a solution of 3-fluorophenylacetic acid ethyl ester 17-1 (3.12 g, 17.15 mmol) in THF (5 mL). After 10 min, a solution of the aminomethylbenzotriazole (4.8 gm, 17.15 mmol) in THF (5 mL) was added and the solution was slowly warmed to room temperature over 5 h. The reaction was quenched with satd aq NH$_4$Cl, extracted with EtOAc (3×40 mL) and the combined organic solutions washed with brine (50 mL). The organic solution was dried over MgSO$_4$, filtered, and concentrated. The residue was purified by flash chromatography (20% ethyl acetate/hexanes) to give the desired product 17-2.

TLC Rf=0.19 (20% ethyl acetate/hexanes).

2-(3-Fluorophenyl)-3-(5-(5,6,7,8-tetrahydro-[1,8] naphthyridin-2-yl)-pentanoylamino)-propionic acid (17-5)

A solution of ester 17-2 (0.47 gm, 1.36 mmol) in EtOH (15 mL) was purged with argon and treated with Pd/C (0.047 gm). The heterogeneous mixture was placed under 1 atm of H$_2$ for 12 h. The mixture was filtered through Celite and concentrated to give amine 17-3 (0.30 g, 100%) as a pale yellow oil. A stirred solution of acid 1-6 (0.09 g, 0.33 mmol), amine 17-3 (0.071, 0.33 mmol), and N-methylmorpholine (0.11 mL, 0.99 mmol) in CH$_3$CN (5 mL) was treated with BOP-reagent (0.15 g, 0.33 mmol). After stirring for 12 h at room temperature, the mixture was concentrated and the residue redissolved in CH$_2$Cl$_2$ (30 mL). The organic solution was washed with satd aq NaHCO$_3$ (10 mL) and brine (10 mL). The solution was dried over Na$_2$SO$_4$, filtered and concentrated to give 0.140 gm of the crude adduct 17-4. Ester 17-4 (0.140 gm, 0.33 mmol) was dissolved in MeOH/THF (2 mL/5 mL) and treated with aq 1N LiOH (1.0 mL). The solution was stirred for 12 h at room temperature. The desired product was purified by preparative HPLC (95:5 to 5:95 H$_2$O/MeCN gradient) to give the acid 17-5.

$^1$H NMR (300 MHz, CD$_3$OD) δ 7.58 (d, J=7.6 Hz, 1H), 7.33 (m, 1H), 7.13 (m, 3H), 6.59 (d, J=7.6 Hz, 1H), 3.89 (t, J=7.3 Hz, 1H), 3.64 (m, 2H), 3.56 (m, 2H), 2.80 (t, J=6.1 Hz, 2H), 2.65 (m, 2H), 2.19 (m, 2H), 1.96 (m, 2H), 1.58 (m, 4H) ppm.

SCHEME 18

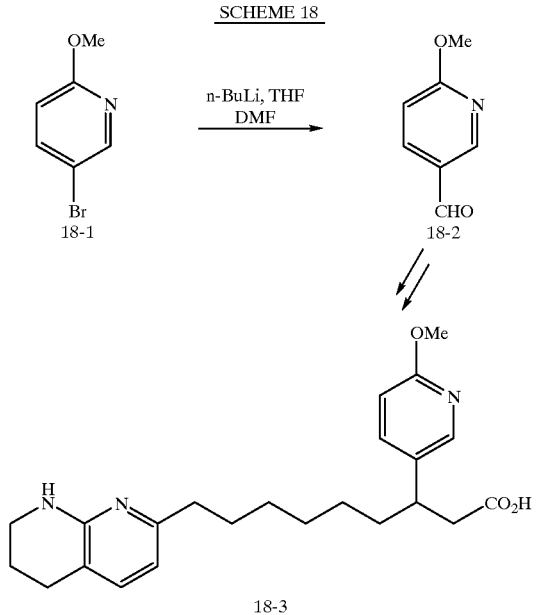

6-Methoxy-pyridine-3-carboxaldehyde (18-2)

A solution of n-butyllithium (3.46 mL of a 1.6 M solution in hexanes) in THF (18 mL) was cooled to −78° C. and treated with a solution of 5-bromo-2-methoxypyridine (Johnson, C. R.; Sirisoma, N. S. *Tetrahedron Lett.* 1998, 39, 2059) 18-1 (1.04 g, 5.53 mmol) in THF (2 mL). The heterogeneous mixture was stirred for 40 min and neat DMF (1.5 mL) was added. The solution was stirred for 90 min at −78° C. and quenched with satd aq $NH_4Cl$ solution (2 mL). The cold bath was removed and the mixture warmed to room temperature. The mixture was extracted with EtOAc (2×30 mL) and the combined organic solutions washed with brine, dried over $MgSO_4$, filtered, and concentrated to the desired aldehyde 18-2.

TLC Rf=0.45 (10% ethyl acetate/hexanes).

3-(6-Methoxy-pyridin-3-yl)-9-(5,6,7,8-tetrahydro-[1,8]naphthyridin-2-yl)-nonanoic acid (18-3)

The 6-methoxypyridine carboxaldehyde 18-2 was transformed to acid 18-3 as per Scheme 15.

$^1$H NMR (300 MHz, $CD_3OD$) δ 8.31 (m, 1H), 8.19 (s, 1H), 7.59 (m, 1H), 7.45 (m, 1H), 6.60 (m, 1H), 4.16 (s, 3H), 3.51 (m, 2H), 3.20 (m, 1H), 2.79 (m, 6H), 1.95 (m, 2H), 1.71 (m, 4H), 1.37 (m, 3H) ppm.

SCHEME 19

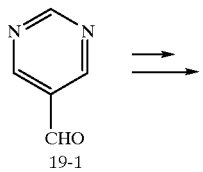

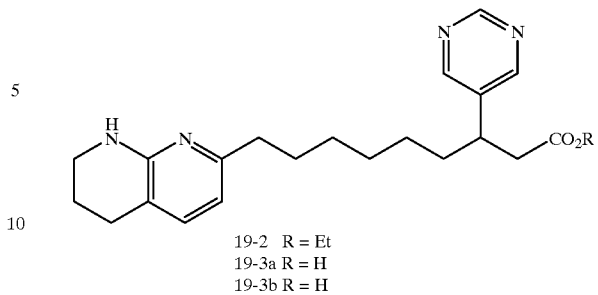

3(R or S)-(Pyrimidin-5-yl)-9-(5,6,7,8-tetrahydro-[1,8]naphthyridin-2-yl)-nonanoic acid and 3(S or R)-(pyrimidin-5-yl)-9-(5,6,7,8-tetrahydro-[1,8]naphthyridin-2-yl)-nonanoic acid (19-3a and 19-3b)

The 5-pyrimidine carboxaldehyde 19-1 (Rho, T.; Abuh, Y. F., *Synthetic Comm.* 1994, 24, 253) was converted into to acid 19-2 as per Scheme 15. Separation of the enantiomers of racemic ethyl ester 19-2 was accomplished by HPLC (Chiralcel OD; 25×2 mm column; 90/10 to 40/60 hexanes/isopropanol/0.1% diethylamine over 60 minutes at a flow rate of 7.0 mL/min) to give the two enantiomers ($R_f$=7.79 min and 8.72 min). Hydrolysis of the resulting optically active esters as per Scheme 15 provided acids 19-3a and 19-3b.

$^1$H NMR (300 MHz, $CD_3OD$) δ 9.01 (s, 1H), 8.71 (S, 2H), 7.57 (d, J=7.4 Hz, 1H), 6.59 (d, J=7.4 Hz, 1H), 3.49 (m, 2H), 3.12 (m, 1H), 2.72 (m, 6 H), 1.96 (m, 2H) 1.72 (m, 4H) 1.30 (m, 6H) ppm.

SCHEME 20

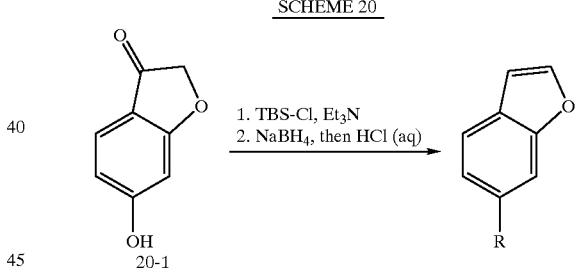

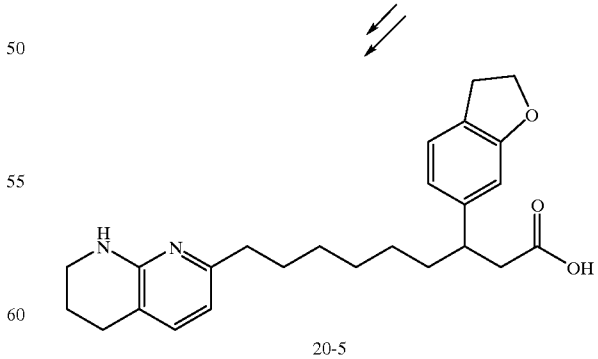

Benzofuran-6-ol (20-2)

To a solution of 6-hydroxy-[2H]-benzofuran-3-one 20-1 (7.84 g, 62.2 mmol) in DMF (100 mL) at room temperature was added triethylamine (8.17 g, 80.9 mmol) and tert-butyldimethylsilyl chloride (10.32 g, 68.4 mmol). After stirring for 2 h, the solution was diluted with Et₂O (300 mL) and washed with satd aq NH₄Cl (150 mL) and brine (100 mL). The solution was dried over MgSO₄, filtered and concentrated to give the benzofuranone as a yellow oil which solidifed upon standing and was not further purified. A solution of this ketone (44.2 g, 167 mmol) in 400 mL MeOH was treated with NaBH₄ (9.5 g, 251 mmol, 1.5 equiv) in four equivalent portions at room temperature until complete by TLC (~1 h). The reaction mixture was quenched by the addition of acetone (10 mL). This mixture was then treated with 3 N aq HCl (200 mL) at room temperature until complete by TLC (~24 h). The resulting solution was concentrated in vacuo to 150 mL and was extracted with EtOAc (2×250 mL). The combined organic extracts were dried (Na₂SO₄), filtered and concentrated in vacuo. The residue was purified by flash chromatography (30% EtOAc/hexanes) affording phenol 20-2 (99%).

TLC Rf=0.35 (30% ethyl acetate/hexanes).

¹H NMR (300 MHz, CDCl₃) δ 7.53 (d, J=1.5 Hz, 1H); 7.41 (d, J=6.3 Hz, 1H); 7.1 (br s, 1H), 6.81-6.78 (dd, J=1.5, 6.3 Hz, 1H), 6.69 (d, J=1.5 Hz, 1H) ppm.

Trifluoromethanesulfonic acid benzofuran-6-yl ester (20-3)

A solution of benzofuran-6-ol 20-2 (4.00 g, 29.85 mmol) and N-phenyltriflimide (10.66 g, 29.85 mmol) in CH₂Cl₂ (150 mL) cooled to 0° C. was treated with triethylamine (5.37 mL, 3.92 g, 38.81 mmol). The reaction was warmed to room temperature over 90 min and diluted with Et₂O (200 mL). The organic solution was washed with satd aq NH₄Cl (100 mL) and brine (100 mL). The solution was dried over MgSO₄, filtered and concentrated. The residue was purified by flash chromatography (5% EtOAc/hexanes) to give the triflate 20-3 as a colorless oil which solidified upon standing.

TLC Rf=0.39 (10% ethyl acetate/hexanes).

¹H NMR (300 MHz, CDCl₃) δ 7.72 (d, J=1.0 Hz, 1H), 7.63 (d, J=8.4 Hz, 1H), 7.48 (br s, 1H), 7.20 (dd, J=8.4, 1.0 Hz, 1H), 6.82 (br s, 1H) ppm Benzofuran-6-carbaldehyde (20-4)

A solution of triflate 20-3 (0.798 g, 3.0 mmol), Pd(OAc)₂ (13.5 mg, 0.060 mmol), and diphenylphosphinopropane (24 mg, 0.060 mmol) in DMF (15 mL) was heated to 70° C. with a gentle flow of CO (g) passing through it. Triethylamine (1.66 mL, 12 mmol) was added followed by trioctylsilane (2.70 mL, 6.0 mmol). The solution was maintained at 70° C. for 2 h, and cooled to room temperature. The solution was diluted with water (10 mL). The mixture was extracted with Et₂O (2×30 mL). The combined organic extracts were washed with brine (10 mL), dried over MgSO₄, filtered and concentrated. The residue was purified by flash chromatography (5% acetone/hexanes) to give the desired aldehyde 20-4.

TLC Rf=0.39 (10% ethyl acetate/hexanes).

3-(2,3-Dihydro-benzofuran-6-yl)-9-(5,6,7,8-tetrahydro-[1,8]naphthyridin-2-yl)-nonanoic acid (20-5)

The aldehyde 20-4 was converted into acid 20-5 as per Scheme 15.

¹H NMR (300 MHz, CDCl₃) δ 7.3 (m, 1H); 7.11 (m, 1H); 6.8 (m, 1H), 6.62 (s, 1H), 6.35 (m, 1H), 4.5 (m, 2H), 3.51 (m, 2H), 3.15 (m, 3H), 2.61 (m, 5H), 1.91 (m, 3H), 1,72 (m, 4H), 1.4 (m, 6H) ppm.

SCHEME 21

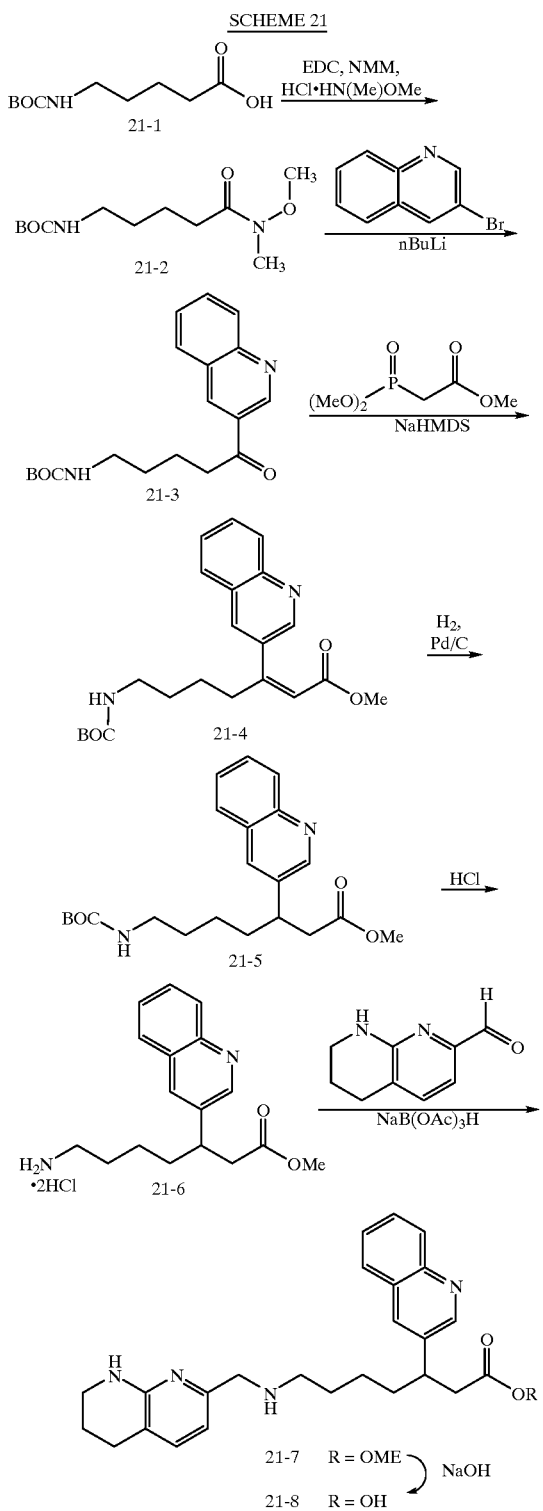

[4-(Methoxy-methyl-carbamoyl)-butyl]-carbamic acid tert-butyl ester (21-2)

N-Boc-aminovaleric acid 21-1 (92 mmol) was dissolved in CH₃CN (300ml) and then treated with HCl.HN(Me)OMe (10.8 g, 110 mmol), EDC (17.6 g, 92 mmol), HOBT (12.4 g, 92 mmol) and NMM (61 mL, 552 mmol). The mixture was stirred for 18 hours and then concentrated. The residue was dissolved in ethyl acetate, washed with H₂O, 10% KHSO₄, sat. NaHCO₃, brine, dried (MgSO₄), and concentrated to give amide 21-2 as a brown oil.

TLC R$_f$=0.67 (silica, ethyl acetate)

¹H MMR (300 MHz, CDCl₃) δ 4.66 (s, 1H), 3.68 (s, 3H), 3.18 (s, 3H), 3.13 (t, 2H, 6 Hz), 2.45 (m, 2H), 1.65 (m, 2H), 1.53 (m, 2H), 1.44 (s, 9H).

(5-Oxo-5-quinolin-3-yl-pentyl)-carbamic acid tert-butyl ester (21-3)

To a stirred solution of 3-bromoquinoline (25 g, 120 mmol) in diethyl ether −78° C. was added nBuLi (2.5M THF, 48 ml, 120 mmol) dropwise over 30 minutes. After 30 minutes, 21-2 (3.9 g, 15 mmol), dissolved in 50 ml ether was added dropwise over 10 minutes. After 30 minutes, the cooling bath was removed. After 1.0 hour, the reaction was quenched with sat. NH₄Cl. The organic portion was separated, washed with brine, dried (MgSO₄) and concentrated. The residue was chromatographed (silica gel, 20–50% ethyl acetate/hexanes) to give 21-3 as a yellow solid.

TLC R$_f$=0.33 (silica, 50% ethyl acetate/hexanes)

7-tert-butoxycarbonylamino-3-quinolin-3-yl-heptanoic acid methyl ester (21-5)

To a stirred solution of trimethylphosphonoacetate (6.7 g, 36.5 mmol) and THF at 0° C. was added NaHMDS (1.0M THF, 37 ml, 37 mmol) dropwise over 30 minutes. After 30 minutes, 21-3 (3.0 g, 9.13 mmol), dissolved in 100 ml THF, was added. The reaction was heated to reflux. After 1.0 hour, the reaction was diluted with diethyl ether and then washed with sat. NaHCO₃, brine, dried (MgSO₄) and concentrated. The residue was chromatographed (silica gel, 50%ethyl acetate/hexanes) to give 21-4 as a yellow oil. A mixture of 21-4 (3.5 g, 9.13 mmol) and 10% Pd/carbon (1.0 g) in CH₃OH (50 mL) was stirred under a balloon of hydrogen for 6 hours. Following filtration and evaporative removal of the solvent, the residue was chromatographed (silica gel, 30–50% ethyl acetate/hexanes) to give 21-5 as a yellow oil.

TLC R$_f$=0.43 (silica, 50% ethyl acetate/hexanes)

¹H NMR (300 MHz, CDCl₃) δ 8.79 (d, 1H, J=2 Hz), 8.08 (d, 1H, J=9 Hz), 7.93 (s, 1H), 7.79 (d,1H, J=8 Hz), 7.68 (m,1H), 7.54 (m, 1H), 4.47 (s,1H), 3.57 (s, 3H), 3.30 (m, 1H), 3.04 (m,2H), 2.73 (m, 2H), 1.78 (m,2H), 1.45 (m, 2H),1.39 (s, 9H), 1.26 (m, 2H).

7-[(5,6,7,8-Tetrahydro-[1,8]naphthyridin-2-ylmethyl)-amino]-3-(quinolin-3-yl)-heptanoic acid methyl ester (21-7)

Ester 21-5 (9.1 mmol) was dissolved in 4M HCl/dioxane (10 ml), stirred for 30 minutes and then concentrated to give the amine 21-6 as a yellow oil. A mixture of 21-6 (900 mg, 2.5 mmol), 3-formyl-5,6,7,8-tetrahydro-[1,8]naphthyridine (405 mg, 2.5 mmol), powdered molecular sieves (2 g), DIPEA (0.35 ml, 2.5 mmol) and DCE (100 mL) was stirred for 30 minutes. The mixture was cooled to 0° C. and then Na(OAc)₃BH (730 mg, 3.5 mmol) was added. After 1 hour, the reaction was diluted with EtOAc and then washed with sat NaHCO₃, brine, and dried over MgSO₄. Following evaporative removal of the solvent, the residue was chromatographed (silica gel, 10% [10:10:1 EtOH/NH₄OH/H₂O]/70:20:10 chloroform/ethyl acetate/MeOH] to give 21-7 as a yellow oil.

¹H NMR (300 MHz, CDCl₃) δ 8.79 (d, 1H, J=2 Hz), 8.08 (d, 1H, J=9 Hz), 7.93 (d, 1H, J=2 Hz), 7.78 (d, 1H, J=8 Hz), 7.67 (m, 1H), 7.54 (m, 1H), 7.05 (d, 1H, J=7 Hz), 6.39 (d, 1H, J=7 Hz), 4.83 (s, 1H), 3.58 (s, 2H), 3.57 (s, 3H), 3.34 (m, 3H), 2.73 (m, 4H), 2.53 (t, 2H, J=7 Hz), 1.89 (m, 2H),1.78 (m, 2H), 1.52 (m, 2H), 1.24 (m, 2H).

7-[(5,6,7,8-Tetrahydro-[1,8]naphthyridin-2-ylmethyl)-amino]-3-(quinolin-3-yl)-heptanoic acid (21-8)

To a solution of 21-7 (0.8255 mmol) in EtOH (5 mL) was added 1N NaOH (1.0 ml, 1.0 mmol). After stirring for 1 hour, the solvents were evaporated and the residue was chromatographed (silica gel, 20:10:1:1 followed by 15:10:1:1 ethyl acetate/EtOH/water NH₄OH) to give 21-8 as a white solid.

TLC Rf=0.10 (10:10:1:1 ethyl acetate/EtOH/water/NH₄OH).

¹H NMR (300 MHz, CD₃OD) δ 8.78 (d, 1H, J=2 Hz), 8.20 (d, 1H, J=2 Hz), 7.97 (d, 1H, J=9 Hz), 7.89 (d, 1H, J=8 Hz), 7.71 (m, 1H), 7.58 (m, 1H), 7.16 (d, 1H, J=7 Hz), 6.43 (d, 1H, J=7 Hz), 3.96 (s, 2H), 3.36 (m, 2H), 2.94 (m, 2H), 2.65 (m, 2H), 1.83 (m, 5H),1.69 (t, 2H, J=8 Hz), 1.30 (m, 2H).

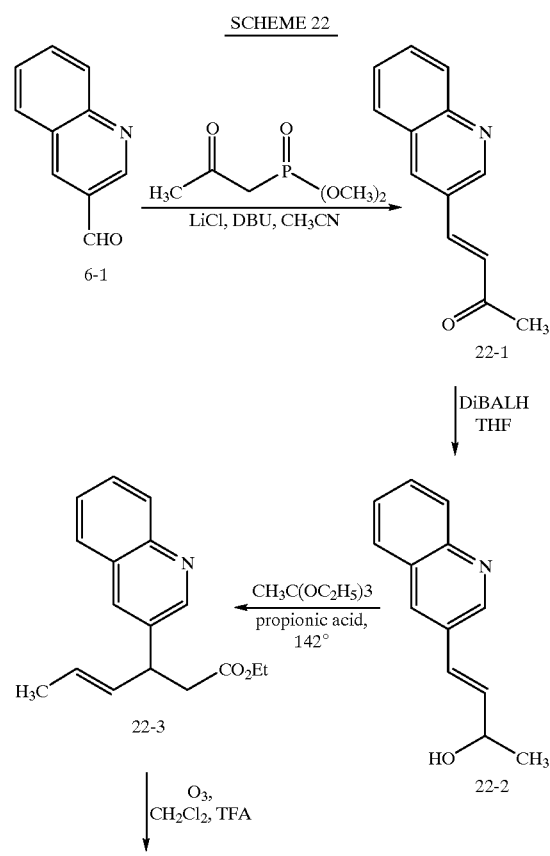

SCHEME 22

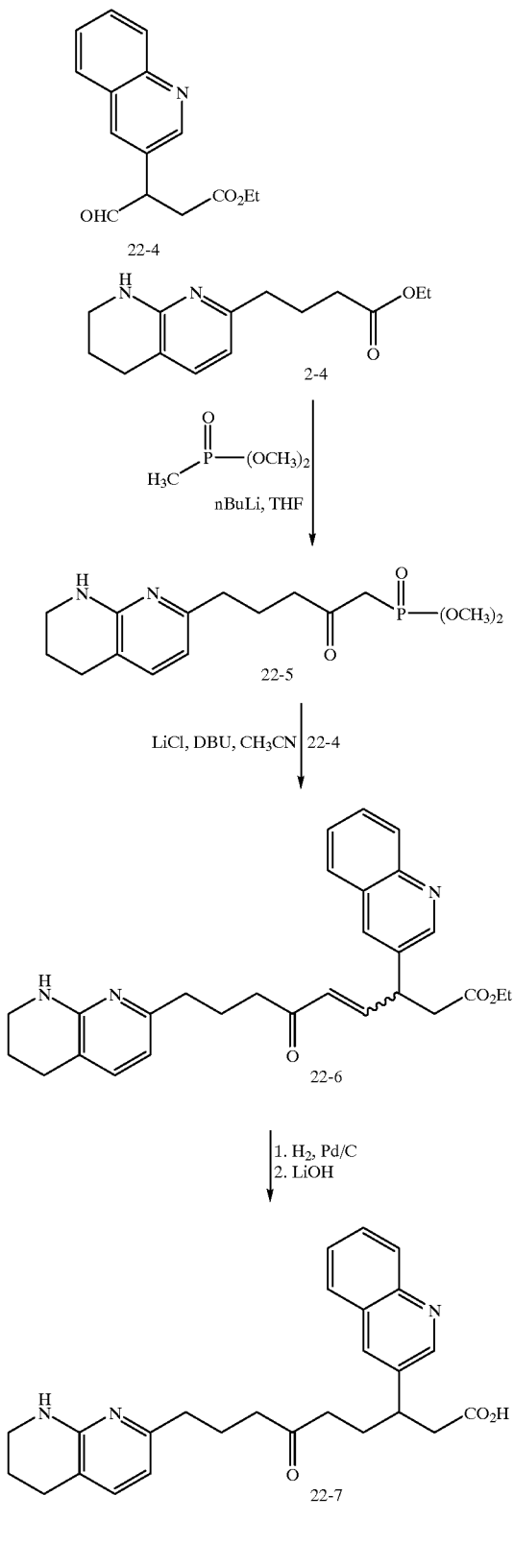

4-(Quinolin-3-yl)-but-3-en-2-one (22-1)

Dimethyl (2-oxopropyl)phosphonate (3.1 g,19.1 mmol), anhydrous LiCl (972 mg, 23 mmol), and 3-quinoline carboxaldehyde 6-1 (3.0 g,19.1 mmol) in anhydrous acetonitrile (70 mL), was treated with DBU (2.9 mL, 19.1 mmol) and the resulting suspension stirred at room temperature for 1 h. The solvent was removed at reduced pressure and the resulting residue partitioned between brine and methylene chloride. The organic layer was removed, dried, and concentrated to afford a yellow solid which was recrystallized from ethyl acetate/hexanes to afford 22-1 as an off-white solid.

$^1$H NMR (300 MHz, CDCl$_3$) δ 9.05 (d, J=1.8 Hz, 1H), 8.35 (d, J=1.8 Hz, 1H), 8.09 (d, J=8.5 Hz, 1H), 7.86 (d, J=7.5 Hz, 1H), 7.75 (t, J=7.5 Hz, 1H), 7.65 (d, J=16 Hz, 1H), 7.55 (t, J=7.5 Hz, 1H), 6.53 (d, J=16 Hz, 1H), 1.44 (s, 3H). $^1$H NMR (300 MHz, CDCl$_3$) d 9.05 (d, J=1.8 Hz, 1H), 8.13 (d, J=8.5 Hz, 1H), 8.09 (d, J=1.8 Hz, 1H), 7.81 (d, J=7.5 Hz, 1H), 7.73 (t, J=7.5 Hz, 1H), 7.55 (t, J=7.5 Hz, 1H), 6.75 (d, J=16 Hz, 1H), 6.53 (dd, J=16, 5.8 Hz, 1H),4.56 (m, 1H), 1.44 (d, J=4.6 Hz, 3H).

4-(Quinolin-3-yl)-but-3-en-2-ol (22-2)

A solution of 22-1 (1.2 g, 6.1 mmol) in anhydrous THF (50 mL) was cooled to −78°, then treated dropwise with i-Bu$_2$AlH (12.75 mL, 12.2 mmol). The resulting solution was stirred at −78° for 20 min, then quenched with ethyl acetate (20 mL), warmed to room temperature, treated with 1 M potassium sodium tartrate (25 mL) and stirred for 4 h. The mixture was extracted with ethyl acetate (2×150 mL) dried, filtered and evaporated to afford 22-2 as a yellow oil.

R$_f$ (silica, EtOAc)=0.30.

$^1$H NMR (300 MHz, CDCl$_3$) δ 9.05 (d, J=1.8 Hz, 1H), 8.13 (d, J=8.5 Hz, 1H), 8.09 (d, J=1.8 Hz, 1H), 7.81 (d, J=7.5 Hz, 1H), 7.73 (t, J=7.5 Hz, 1H), 7.55 (t, J=7.5 Hz, 1H), 6.75 (d, J=16 Hz, 1H), 6.53 (dd, J=16, 5.8 Hz, 1H),4.56 (m, 1H), 1.44 (d, J=4.6 Hz, 3H).

3-(Quinolin-3-yl)-hex-4-enoic acid ethyl ester (22-3)

A solution of the allylic alcohol 22-2 (1.2 g, 6.1 mmol) in triethyl orthoacetate (50 mL) was treated with propionic acid (0.022 mL, 0.31 mmol) and refluxed for 2 h. The cooled mixture was treated with a solution of 1:1 sat. brine/1N HCl (150 mL), then extracted with CH$_2$Cl$_2$ (3×125 mL). The pooled organic extracts were washed with sat. NaHCO$_3$, dried, filtered and evaporated. Chromatography on silica gel (EtOAc) afforded 22-3 as a yellow glass.

R$_f$ (silica,EtOAc)=0.65.

$^1$H NMR (300 MHz , CDCl$_3$) δ 8.92 (d, J=1.8 Hz, 1H), 8.15 (d, J=8.5 Hz, 1H), 7.96 (d, J=1.8 Hz, 1H), 7.82 (d, J=7.5 Hz, 1H), 7.71 (t, J=7.5 Hz, 1H), 7.54 (t, J=7.5 Hz, 1H), 5.6 (m, 2H), 4.21 (m, 1H), 4.05 (t, J=7.4 Hz, 2H), 2.79 (m, 2H),1.91 (d, J=6 Hz, 2H), 1.08 (t, J=7.4 Hz, 3H).

4-Oxo-3-(quinolin-3-yl)-butyric acid ethyl ester (22-4)

A solution of 22-3 (1.0 g, 3.7 mmol), TFA (0.06 mL, 3.9 mmol), and sudan red (0.5 mg) in anhydrous CH$_2$Cl$_2$ (50 mL) was cooled to −78° and treated with O$_3$ until the sudan red color disappeared (5 min). Solid Ph$_3$P (1.4 g, 5.6 mmol) was added and the solution warmed to room temperature. After 30 min., the solution was washed with sat. NaHCO$_3$, dried, filtered, and evaporated. Chromatography on silica gel (10% acetone/EtOAc) afforded 22-4 as colorless glass.

R$_f$ (silica,EtOAc)=0.25.

$^1$H NMR (300 MHz, CDCl$_3$) δ 9.88(s, 1H), 8.82 (d, J=1.8 Hz, 1H), 8.13 (d, J=8.5 Hz, 1H), 7.96 (d, J=1.8 Hz, 1H), 7.82 (d, J=7.5 Hz, 1H), 7.76 (t, J=7.5 Hz, 1H), 7.58 (t, J=7.5 Hz,

1H), 4.4 (m, 1H), 4.05 (t, J=7.4 Hz, 1H), 4.13 (m, 2H), 3.30 (dd, J=7.6, 16 Hz, 1H), 2.87 (dd, J=7.2, 16 Hz, 1H), 1.20 (m, 3H).

2-Oxo-5-(5,6,7,8-tetrahydro-[1,8]-naphthyridin-2-yl)-pentyl-phosphonic acid dimethyl ester (22-5)

A solution of dimethyl methylphosphonate (10.0 g, 80.5 mmol) in anhydrous THF (125 mL) was cooled to −78° and treated dropwise with 2.5 M n-BuLi (32.2 mL). After stirring at −78° for 45 min, a solution of ester 22-4 (6.6 g, 26.6 mmol) in THF (35 mL) was added dropwise and the resulting solution stirred for 30 min at −78°, quenched with sat. NH$_4$Cl (100 mL), then extracted with ethyl acetate (3×150 mL). The combined organic extracts were dried (MgSO$_4$), filtered, and concentrated to afford a yellow oil. Chromatography on silica gel (5% MeOH/CH$_2$Cl$_2$) afforded 22-5 as a yellow oil.

R$_f$ (silica, 5% MeOH/CH$_2$Cl$_2$)=0.20.

$^1$H NMR (300 MHz, CDCl$_3$) δ 7.05 (d, J=7.3 Hz, 1H), 6.34 (d, J=7.32 Hz, 1H), 4.80 (br, s, 1H), 3.81 (s, 3H), 3.75 (s, 3H), 3.4 (m, 2H), 3.08 (d, J=22.7 Hz), 2.72 (m, 6 H), 2.56 (t, 2 H), 1.91 (m, 2H).

6-Oxo-(3-quinolin-3-yl)-9-(5,6,7,8-tetrahydro-[1,8] naphthyridin-2-yl)-nonanoic acid (22-7)

Ketophosphonate 22-5 (1.0 g, 3.1 mmol), anhydrous LiCl (170 mg, 4.0 mmol), and 22-4 (0.797 g, 3.1 mmol) in anhydrous acetonitrile (60 mL), was treated with DBU (0.52 mL, 3.3 mmol) and the resulting suspension stirred at room temperature for 1 h. The solvent was removed at reduced pressure and the resulting residue partitioned between brine and methylene chloride. The organic layer was removed, dried, and concentrated to afford 22-6 as mixture of E and Z olefins. The crude mixture was dissolved in EtOH (50 mL), treated with 10% Pd/C (200 mg) and stirred under a hydrogen filled balloon for 4 h, then filtered. The filtrate was treated with LiOH (2.0 eq) and water (20 mL) and stirred at room temperature for 12 h, then neutralized with 1N HCl and evaporated Chromatography on silica gel (10% MeOH/ methylene chloride) afforded 22-7 as a white solid.

R$_f$ (silica,10% MeOH/CH$_2$Cl$_2$)=0.20.

$^1$H NMR (300 MHz, CDCl$_3$) δ 10.9 (br,s, 1H), 8.92 (d, J=1.8 Hz, 1H), 8.21(d, J=7.5 Hz, 1H), 8.05 (d, J=1.8 Hz, 1H), 7.87 (d, J=7.5 Hz, 1H), 7.81 (t, J=7.5 Hz, 1H), 7.58 (t, J=7.5 Hz, 1H), 7.25 (d, J=7.3 Hz, 1H), 6.34 (d, J=7.3 Hz, 1H), 3.81 (m, 1H), 3.44 (m, 2H), 3.0-2.2 (m, 12 H), 1.92 (m, 2H), 1.68 (m, 1H) 1.42 (m, 1H).

SCHEME 23

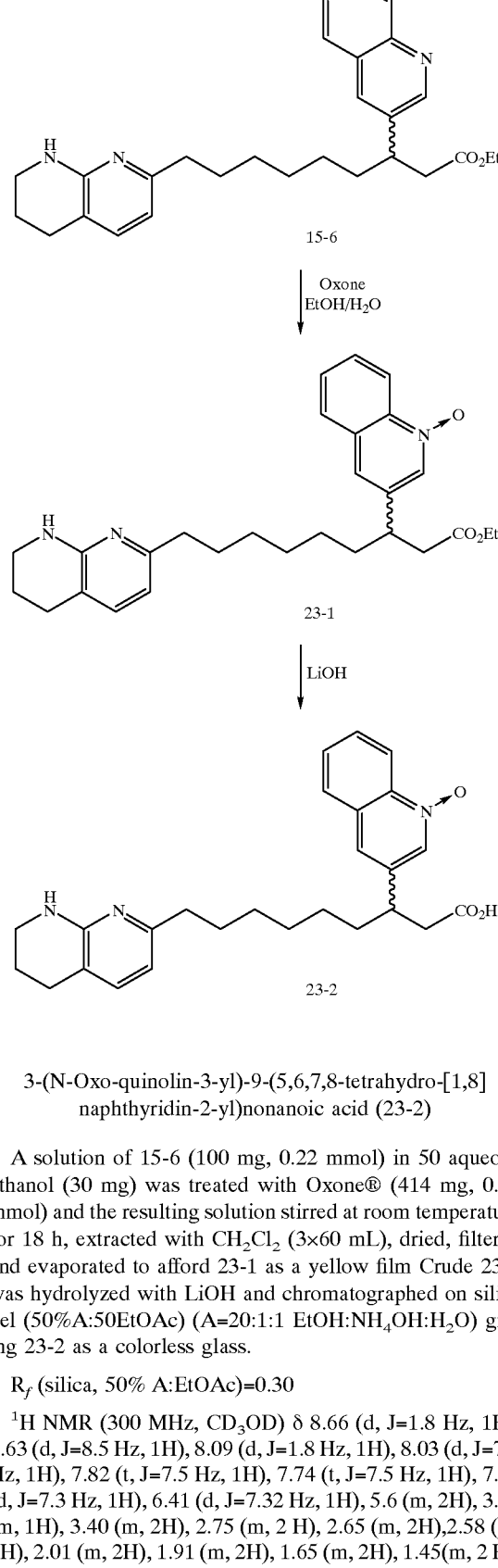

3-(N-Oxo-quinolin-3-yl)-9-(5,6,7,8-tetrahydro-[1,8] naphthyridin-2-yl)nonanoic acid (23-2)

A solution of 15-6 (100 mg, 0.22 mmol) in 50 aqueous ethanol (30 mg) was treated with Oxone® (414 mg, 0.66 mmol) and the resulting solution stirred at room temperature for 18 h, extracted with CH$_2$Cl$_2$ (3×60 mL), dried, filtered and evaporated to afford 23-1 as a yellow film Crude 23-1 was hydrolyzed with LiOH and chromatographed on silica gel (50%A:50EtOAc) (A=20:1:1 EtOH:NH$_4$OH:H$_2$O) giving 23-2 as a colorless glass.

R$_f$ (silica, 50% A:EtOAc)=0.30

$^1$H NMR (300 MHz, CD$_3$OD) δ 8.66 (d, J=1.8 Hz, 1H), 8.63 (d, J=8.5 Hz, 1H), 8.09 (d, J=1.8 Hz, 1H), 8.03 (d, J=7.5 Hz, 1H), 7.82 (t, J=7.5 Hz, 1H), 7.74 (t, J=7.5 Hz, 1H), 7.30 (d, J=7.3 Hz, 1H), 6.41 (d, J=7.32 Hz, 1H), 5.6 (m, 2H), 3.56 (m, 1H), 3.40 (m, 2H), 2.75 (m, 2 H), 2.65 (m, 2H),2.58 (m, 2H), 2.01 (m, 2H), 1.91 (m, 2H), 1.65 (m, 2H), 1.45(m, 2 H).

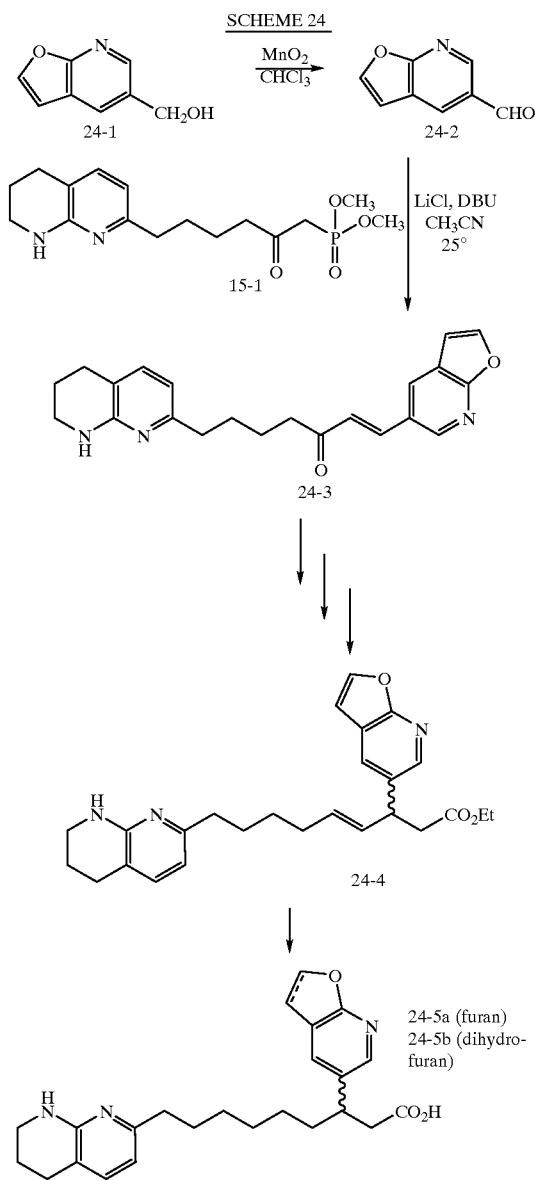

Furo-[2,3-b]pyridine-5-carboxaldehyde (24-2)

A solution of alcohol 24-1 (Bhupathy, M.; et al. J. Heterocycl. Chem. (1995), 32, 1283–1287) was treated with excess $MnO_2$ (10 eq) and the mixture stirred at room temperature for 16 h, then filtered through Celite and evaporated to afford 24-2 as a white solid.

TLC Rf=0.40 (25% EtOAc/Hexane)

$^1$H NMR (300 MHz, $CDCl_3$) δ 10.22 (s, 1H), 9.05 (d, J=1.8 Hz, 1H), 8.27 (d, J=1.7 Hz, 1H) 8.08 (d, J=1.8 Hz, 1H), 7.10 (d, J=1.7 Hz, 1H).

3-Furo-[2,3-b]pyridin-5-yl-7-(5,6,7,8-tetrahydro-[1,8]-naphthyridin-2-yl)-(E)-hept-1-en-3-one (24-3)

Ketophosphonate 15-1 (0.69 g, 2.0 mmol), anhydrous LiCl (86 mg, 2.0 mmol), and 24-2 (0.25 g, 1.7 mmol) in anhydrous acetonitrile (25 mL), was treated with DBU (0.25 mL, 1.8 mmol) and the resulting suspension stirred at room temperature for 1 h. The solvent was removed at reduced pressure and the resulting residue partitioned between brine and methylene chloride. The organic layer was removed, dried, and concentrated to afford a yellow solid which was chromatographed on silica (5% isopropanol/chloroform) to give 24-3 as an off-white solid.

$R_f$ (silica, 5% isopropanol/$CH_2Cl_2$)=0.45.

$^1$H NMR (300 MHz, $CDCl_3$) δ 8.50 (d, J=2.1 Hz, 1H), 8.13 (d, J=2.1 Hz, 1H), 7.75(d, J=2.4 Hz, 1H),7.60 (d, J=16 Hz, 1H), 7.06 (d, J=7.3 Hz, 1H), 6.83 (d, J=2.4 Hz, 1H), 6.77 (d, J=16 Hz, 1H), 6.36 (d, J=7.3 Hz, 1H), 4.85 (br, s, 1H), 3.4 (m, 2H), 2.7-2.5 (m, 6 H), 1.91 (m, 2H), 1.68 (m, 4H).

3-(Furo[2,3-b]pyridin-5-yl)-9-(5,6,7,8-tetrahydro-[1,8]naphthyridin-2-yl)-(E)-non-4-enoic acid ethyl ester (24-4)

24-3 was converted to 24-4 via the methods taught in the conversion of 15-4 to 15-5.

$R_f$ (silica, 5% isopropanol/$CH_2Cl_2$)=0.40.

$^1$H NMR (300 MHz, $CDCl_3$) δ 8.18 (d, J=2.1 Hz, 1H), 7.91 (d, J=2.1 Hz, 1H), 7.72 (d, J=2.4 Hz, 1H), 7.05 (d, J=7.3 Hz, 1H), 6.53 (d, J=2.4 Hz, 1H), 6.36 (d, J=7.3 Hz, 1H), 5.6 (m, 2H), 4.85 (br, s, 1H), 4.05 (q, J=7.5 Hz, 2H), 4.05 (m, 1H), 3.40 (m, 2H), 2.75 (m, 2 H), 2.65 (m, 2H),2.58 (m, 2H), 2.01 (m, 2H), 1.91 (m, 2H), 1.65 (m, 2H), 1.45(m, 2 H), 1.08 (t, J=7.5 Hz, 3H).

3-(Furo[2,3b]-pyridin-5-yl)-9-(5,6,7,8-tetrahydro-[1,8]naphthyridin-2-yl)-nonanoic acid (24-5a)

A solution of 24-4 (108 mg, 0.25 mmol) in ethanol was treated with 10% Pd/C (30 mg) and stirred under a $H_2$ filled balloon for 6 h, then filtered through Celite and evaporated. Hydrolysis of the crude product with LiOH and chromatography on silica ((50%A:50EtOAc)(A= 20:1:1EtOH:$NH_4OH$:$H_2O$) afforded 24-5a and 24-5b as white solids.

$R_f$ (silica, 50% A:EtOAc)=0.45

$^1$H NMR (300 MHz, $CDCl_3$) δ 10.7 (br, s, 1H), 8.25 (d, J=1.8 Hz, 1H), 7.81 (d, J=1.8 Hz, 1H),7.68 (d, J=1.8 Hz, 1H), 7.21 (d, J=7.3 Hz, 1H), 6.75 (d, J=1.7 Hz, 1H), 6.25 (d, J=7.3 Hz, 1H), 3.56 (m, 1H), 3.40 (m, 2H), 2.75 (m, 2 H), 2.65 (m, 2H),2.58 (m, 2H), 2.01 (m, 2H), 1.91 (m, 2H), 1.65 (m, 2H), 1.45(m, 2 H).

3-(2,3-Dihydro-furo[2,3-b]-pyridin-5-yl)-9-(5,6,7,8-tetrahydro-[1,8]naphthyridin-2-yl)-nonanoic acid (24-5b)

$R_f$ (silica, 50% A:EtOAc)=0.45

$^1$H NMR (300 MHz, $CDCl_3$) δ 10.8 (br, s, 1H), 7.85 (d, J=1.8 Hz, 1H),7.40 (d, J=1.8 Hz, 1H), 7.21 (d, J=7.3 Hz, 1H), 6.25 (d, J=7.3 Hz, 1H), 4.60 (t, J=7.4 Hz, 2 H), 3.7 (m, 1H), 3.40 (m, 2H),3.20 (t, J=7,4 Hz, 2H), 2.75 (m, 2 H), 2.65 (m, 2H),2.58 (m, 2H), 2.01 (m, 2H), 1.91 (m, 2H), 1.65 (m, 2H), 1.45(m, 2 H).

SCHEME 25

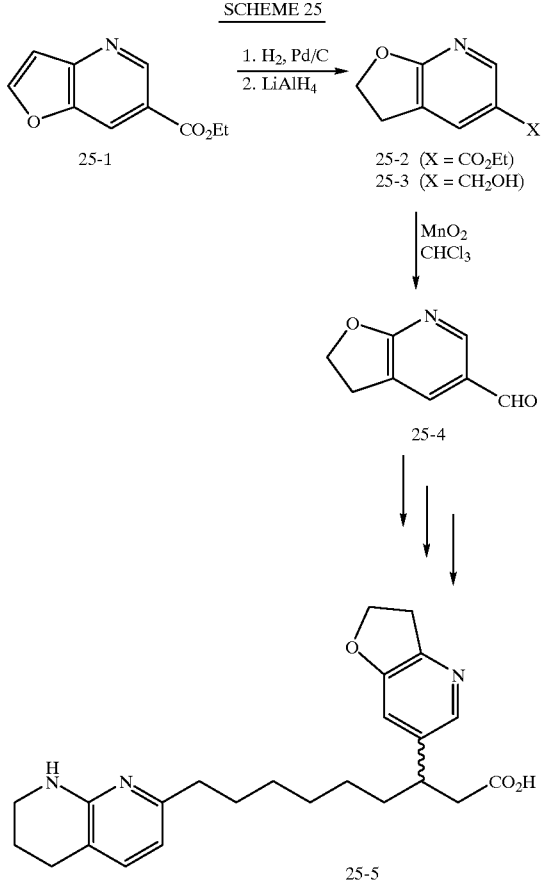

2,3-Dihydro-furo[3,2-b]pyridine-5-ethylcarboxylate (25-2)

A solution of ester 25-1 (Hoffman, Jacob M., Jr. U.S. Pat. No. 4,808,595) in ethanol was treated with 10% Pd/C (30 wt %) and stirred under a hydrogen atmosphere for 22 h, then filtered and evaporated to afford 25-2 as a tan solid.

TLC Rf=0.40 (25% EtOAc/Hexane).

¹H NMR (300 MHz, CDCl₃) δ 8.45 (d, J=1.8 Hz, 1H), 7.23 (d, J=1.8 Hz, 1H). 4.72 (t, J=7.5 HZ, 2H), 4.01 (q, J=7.4 Hz, 2H), 3.42 (t, J=7.5 Hz, 2H), 1.02 (t, J=7.4 Hz,3H).

2,3-Dihydro-furo[3,2b]pyridine-5-methanol (25-3)

A solution of ester 25-2 (1.93 g, 10 mmol) in anhydrous THF (150 mL) was cooled to −78°, then treated dropwise with LAH (10.75 mL, 10.75 mmol). The resulting solution was stirred at −78° for 20 min, then warmed to 25° and stirred for 4 h, then quenched with ethyl acetate (20 mL), treated with 1 M potassium sodium tartrate (25 mL) and stirred for 4 h. The mixture was extracted with ethyl acetate (2×150 mL), dried, filtered, and evaporated to afford 25-3 as a white solid which was carried on without further purification.

TLC Rf=0.6 (EtOAc).

¹H NMR (300 MHz, CDCl₃) δ 8.10 (d, J=1.8 Hz, 1H), 7.13 (d, J=1.8 Hz, 1H). 5,10 (s, 2H), 4.65 (t, J=7.5 HZ, 2H), 3.36 (t, J=7.5 Hz, 2H).

2,3-Dihydro-furo[3.2b]pyridine-5-carboxaldehyde (25-4)

A solution of alcohol 25-3 was treated with excess MnO₂ (10 eq) and the mixture stirred at room temperature for 16 h and then filtered through Celite and evaporated to afford 25-4 as a white solid.

TLC Rf=0.35 (25% EtOAc/Hexane)

¹H NMR (300 MHz, CDCl₃) δ 10.08 (s, 1H),8.43 (d, J=1.8 Hz, 1H), 7.45 (d, J=1.8 Hz, 1H). 4.72 (t, J=7.5 Hz, 2H), 3.42 (t, J=7.5 Hz, 2H).

3-(2,3-Dihydro-furo[3,2-b]pyridin-5-yl)-9-(5,6,7,8-tetrahydro-[1,8]naphthyridin-2-yl)-nonanoic acid (25-5)

Prepared from aldehyde 25-4 using the method described for the preparation of 15-7.

¹H NMR (300 MHz, CD₃OD) δ 7.80 (d, J=1.5 Hz, 1H), 7.41 (d, J=7.3 Hz, 1H), 7.02 (d, J=1.5 Hz, 1H), 6.45 (d, J=7.3 Hz, 1H), 4.72 (t, J=7.5 Hz, 2H), 3.56 (m, 1H), 3.46 (m, 2H), 3.42 (t, J=7.5 Hz, 2H), 2.75 (m, 2H), 2.62 (m, 2H), 2.50 (m, 2H), 1.95 (m, 2H), 1.91 (m, 2H), 1.65 (m, 2H), 1.45 (m, 2 H).

SCHEME 26

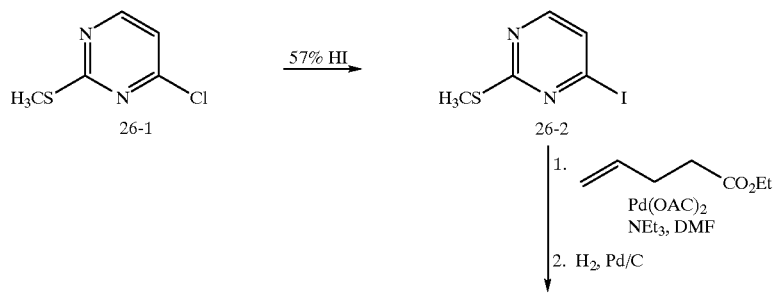

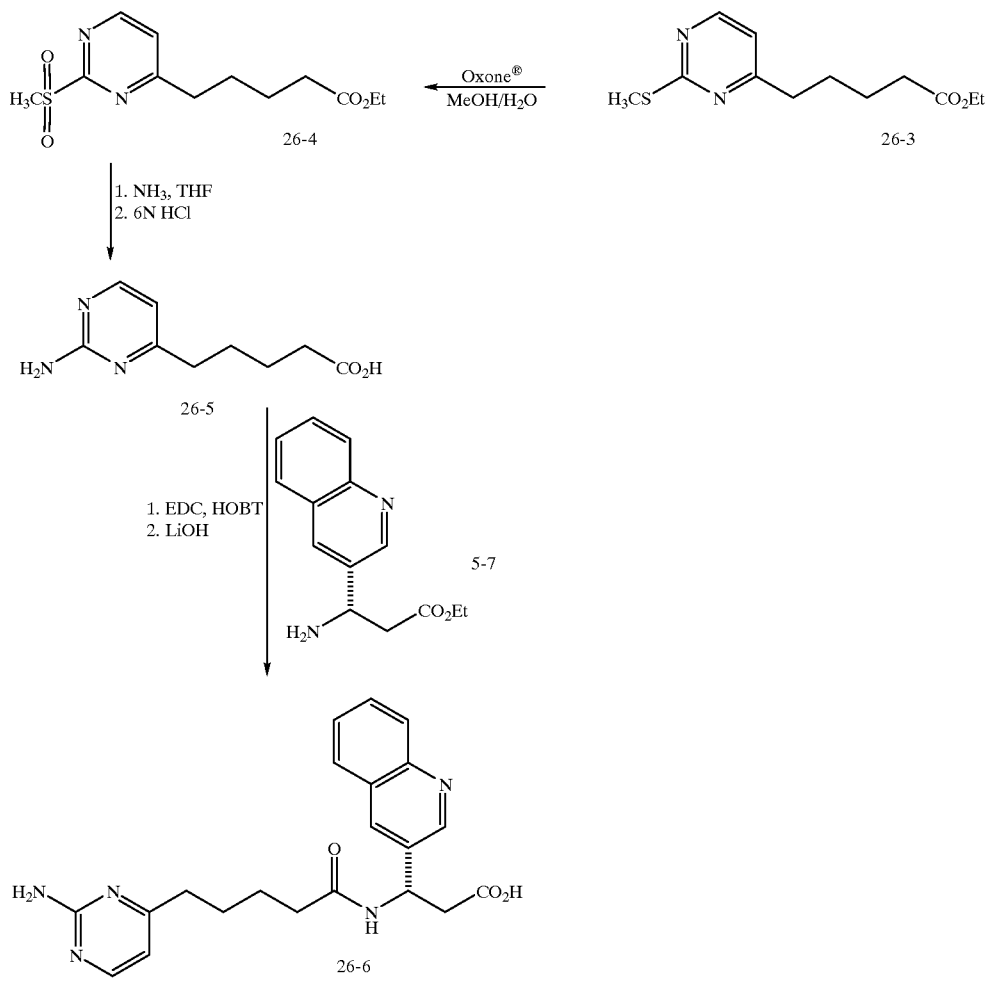

4-Iodo-2-methylthiopyrimidine (26-2)

Chloride 26-1 (10 g, 62,3 mmol) was added dropwise to a 0° solution of 57% HI (50 mL) after 30 min the ice bath was removed, and the resulting orange suspension stirred at ambient temperature for 16 h. The solution was carefully quenched with sat. sodium bicarbonate (400 mL) and the solution adjusted to pH=9 with solid sodium carbonate, and extracted with EtOAc (2×200 mL). The combined organic extracts were dried and evaporated to afford a colorless oil which was dissolved in boiling hexane, then chilled to give 26-2 as colorless needles.

TLC Rf=0.4 (20%EtOAc/Hexane).

$^1$H NMR (300 MHz, CDCl$_3$) δ 8.01 (d, J=5.1 Hz, 1H), 7.41 (d, J=5.1 Hz, 1H). 2.54 (s, 3H).

5-(2-methylthio-pyrimidin-4-yl)-pentanoic acid ethyl ester (26-3)

A solution of 26-2 (9.5 g, 38 mmol) in DMF (150 mL) was treated with Pd(OAc)$_2$ (0.43 g, 1.9 mmol) and Et$_3$N (8.0 g, 80 mmol), purged with argon, and the mixture heated to 50° for 16 h. The solvent was removed at reduced pressure and the brown residue partitioned between ethyl acetate and sat. sodium bicarbonate. The organic layer was dried, filtered, and evaporated and the residue purified by chromatography on silica (20%EtOAc/Hexane) to afford 26-3 as an oil.

TLC Rf=0.3 (20%EtOAc/Hexane).

$^1$H NMR (300 MHz, CDCl$_3$) δ 8.41 (d, J=5.1 Hz, 1H), 7.0 (m, 1H), 6.80 (d, J=5.1 Hz, 1H). 6.38 (d, J=15.8 Hz, 1H), 4.18 (q, J=7.3 Hz, 2H), 2.7-2.5 (4H), 2.57 (s, 3H), 1.25 (t, J=7.3 Hz, 3H).

This material (5.6 g, 22 mmol) was reduced at 1 atm. H$_2$ using 10%Pd/C (1.2 g, 20 wt. %) in ethanol to afford 26-3 as colorless oil.

TLC Rf=0.3 (20%EtOAc/Hexane).

$^1$H NMR (300 MHz, CDCl$_3$) δ 8.41 (d, J=5.1 Hz, 1H), 6.80 (d, J=5.1 Hz, 1H). 4.18 (q, J=7.3 Hz, 2H), 2.65 (t, J=7.4 Hz, 2H), 2.57 (s, 3H), 2.35 (t, J=7.4 Hz, 2H),1.7 (4H), 1.25 (t, J=7.3 Hz, 3H).

5-(2-methanesulfonyl-pyrimidin-4-yl)-pentanoic acid ethyl ester (26-4)

To a solution of 26-3 (2.0 g, 8.0 mmol) in MeOH (100 mL) was added a solution of Oxone® (14.5 g, 24 mmol) in H$_2$O (100 mL). The resulting solution was stirred at ambient temperature for 20 h, then the MeOH was removed at reduced pressure and the aqueous phase diluted with sat. NaHCO$_3$ (100 mL) and extracted with EtOAc (2×100 mL). The organic layers were dried, filtered and concentrated to afford 26-4 as a colorless oil.

TLC Rf=0.3 (20%EtOAc/Hexane).

¹H NMR (300 MHz, CDCl₃) δ 8.75 (d, J=5.1 Hz, 1H), 7.43 (d, J=5.1 Hz, 1H). 4.18 (q, J=7.3 Hz, 2H), 3.37 (s, 3H), 2.92 (t, J=7.4 Hz, 2H), 2.37 (t, J=7.4 Hz, 2H), 1.87 (m, 2H), 1.72 (m, 2H), 1.25 (t, J=7.3 Hz, 3H).

5-(2-amino-pyrimidin-4-yl)-pentanoic acid (26-5)

A solution of 26-4 (0.19 g, 0.67 mmol) in THF (5 mL) was cooled to 0° and saturated with NH₃ gas. The mixture was stirred at 0° for 4 h, then evaporated and the residue partitioned between EtOAc and sat. NaHCO₃. The organic layer was dried filtered and concentrated to give the amino ester 26-5.

TLC Rf=0.3 (EtOAc).

¹H NMR (300 MHz, CD₃OD) δ 8.16 (d, J=5.1 Hz, 1H), 6.75 (d, J=5.1 Hz, 1H). 4.18 (q, J=7.3 Hz, 2H), 2.58 (t, J=7.4 Hz, 2H), 2.35 (t, J=7.4 Hz, 2H),1.7 (4H), 1.25 (t, J=7.3 Hz, 3H).

The ester obtained above was dissolved in 6N HCl and stirred at ambient temperature for 16 h then concentrated to afford 26-5 as its HCl salt.

¹H NMR (300 MHz, CD₃OD) δ 8.53 (d, J=5.1 Hz, 1H), 6.85 (d, J=5.1 Hz, 1H). 2.58 (t, J=7.4 Hz, 2H), 2.35 (t, J=7.4 Hz, 2H),1.7 (4H).

3-[5-(2-Amino-pyrimidin-4-yl)-pentanoylamino]-3 (S)-(quinolin-3-yl)-propionic acid (26-6)

26-6 was obtained following the coupling of 26-5 and 5-7 and subsequent saponification as described for 1-6 and 1-7 to furnish 1-9.

¹H NMR (300 MHz, CD₃OD) δ 8.53 (s, 1H), 20 (s, 1H), 7.7 (d, J=7 Hz, 1H), 7.7-7.4(4H), 6.11 (d, J=5 Hz, 1H), 5.3 (m,1H), 3,5 (m, 3H), 2.5 (m, 2H), 2.10 (m, 4H0), 1.51 (m, 2 H), 1.3 (m, 2H).

3-(4-Aminbutyrylamino)-3-(S)-(3-fluorophenyl)-propionic acid ethyl ester hydrochloride (27-2)

A mixture of 27-1 (245 mg, 1.2 mmol), 9-1 (300 mg, 1.21 mmol), EDC (300 mg, 1.57 mmol), NMM (490 mg, 4.84 mmol), and HOBT (213 mg,157 mmol) in DMF (7 mL) was stirred under argon for 16 h, then diluted with EtOAc (50 mL ) and washed successively with sat. NaHCO₃, H₂O, 10% KHSO₄, and brine (20 mL), dried and concentrated to give the Boc-protected amino ester as an oil.

TLC Rf=0.7 (90%EtOAc/Hexane).

¹H NMR (300 MHz, CDCl₃) δ 7.3 (t, J=7.8 Hz, 1H),7.1 (d, J=7.8 Hz, 1H). 7.07 (d, J=7.8 Hz, 1H). 6.92 (t, J=7.8 Hz, 1H), 5.40 (m, 1H), 4.80 (br, t, 1H), 4.18 (q, J=7.3 Hz, 2H), 3.20 (m, 2H), 2.82 (t, J=7.4 Hz, 2H), 2.35 (t, J=7.4 Hz, 2H),1.7 (4H), 1.25 (t, J=7.3 Hz, 3H).

The Boc protected amino ester obtained above (440 mg, 1.1 mmol) was dissolved in 2.3N ethanolic HCl (10 mL) and stirred at ambient temperature for 3 h then concentrated to afford 27-2 as its HCl salt.

¹H NMR (300 MHz, CD₃OD) δ 7.3 (t, J=7.8 Hz, 1H),7.1 (d, J=7.8 Hz, 1H). 7.07 (d, J=7.8 Hz, 1H). 6.92 (t, J=7.8 Hz, 1H), 5.40 (m, 1H), 4.18 (q, J=7.3 Hz, 2H), 3.20 (m, 2H), 2.82 (t, J=7.4 Hz, 2H), 2.35 (t, J=7.4 Hz, 2H),1.7 (4H), 1.25 (t, J=7.3 Hz, 3H).

3(S)-(3-Fluorophenyl)-3-[4-([1,8]naphthyridin-2-ylamino)butyrylamino]propionic acid ethyl ester (27-4)

A mixture of amine hydrochloride 27-2 (350 mg, 1.1 mmol), bromide 27-3 (230 mg, 1.1 mmol) (for preparation see: Roszkiewicz, W.; Wozniak, M.; Synthesis 1976, 691–2), and DIPEA (355 mg, 2.75 mmol) in acetonitrile (5.5 mL) was heated at reflux for 20 h. The solution was concentrated and the brown residue partitioned between EtOAc and sat. NaHCO₃. The organic layer was washed

SCHEME 27

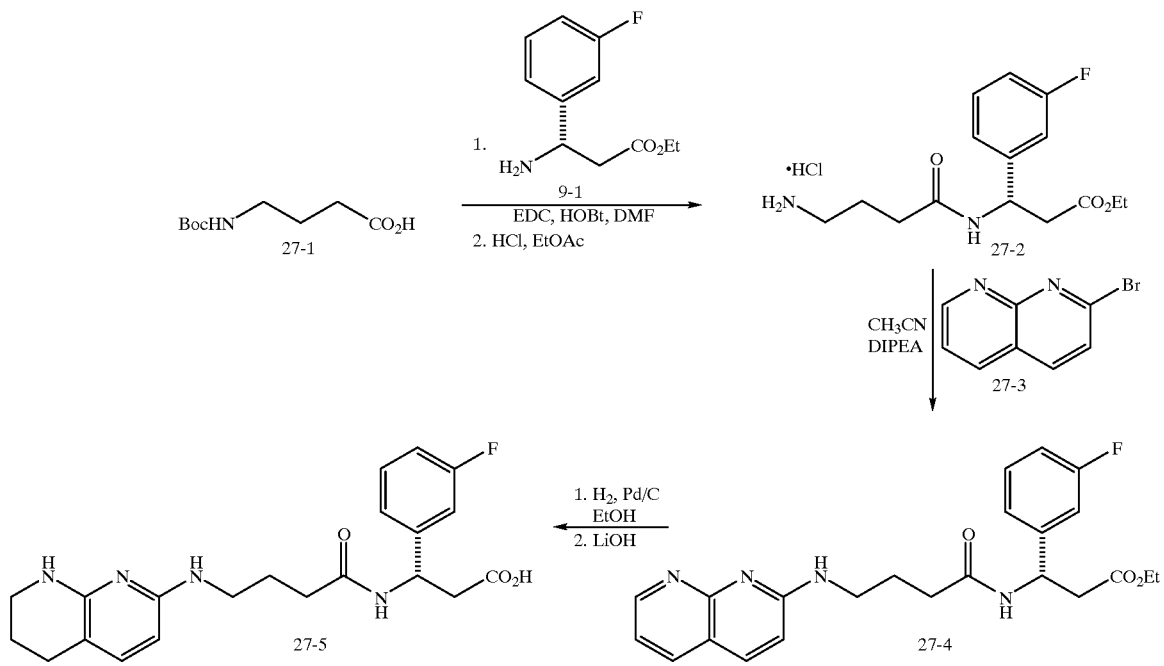

with brine, dried, filtered, concentrated and the oil chromatographed on silica (5% EtOH/EtOAc) to afford 27-4 as a colorless glass.

TLC Rf 0.45 (5% EtOH/EtOAc).

$^1$H NMR (300 MHz, CDCl$_3$) δ 8.80 (d, J=1.8 HZ, 1H), 8.50 (br,d, J-7 Hz, 1H), 7.85 (d,d, J=1.8, 7.0 Hz, 1H), 7.75 (d, J=7.5 Hz, 1H). 7.2-6.8 (5H), 6.62 (d, J=7.5 Hz, 1H), 5.61 (m, 1H), 5.31 (br, t, 1H), 4.18 (q, J=7.3 Hz, 2H), 3.60 (m, 2H), 3.2 (dd, J=6.0, 10.5 Hz, 1H) 3.02 (dd, J=5.6,10.5 Hz, 1H) 2.22 (t, J=7.4 Hz, 2H),1.92 (m, 2H), 1.25 (t, J=7.3 Hz, 3H).

3(S)-(3-Fluorophenyl)-3-[4-(5,6,7,8-tetrahydro-[1,8] naphthyridin-2-ylamino)-butyrylamino]-propionic acid bis trifluoroacetate (27-5)

A solution of 27-4 (90 mg, 0.21 mmol) in EtOH (3 ml) was treated with 10% Pd/C (60 mg) and the mixture stirred under a H$_2$ filled balloon for 24 h. The catalyst was removed by filtration and the filtrate concentrated to afford crude reduced ester. This material was hydrolyzed with LiOH, neutralized with 1N HCl, concentrated and the residue purified by reverse phase chromatography to afford 27-5 as its bis-TFA salt.

High resolution Ms Calc'd.=401.1977, Observed=401.1983.

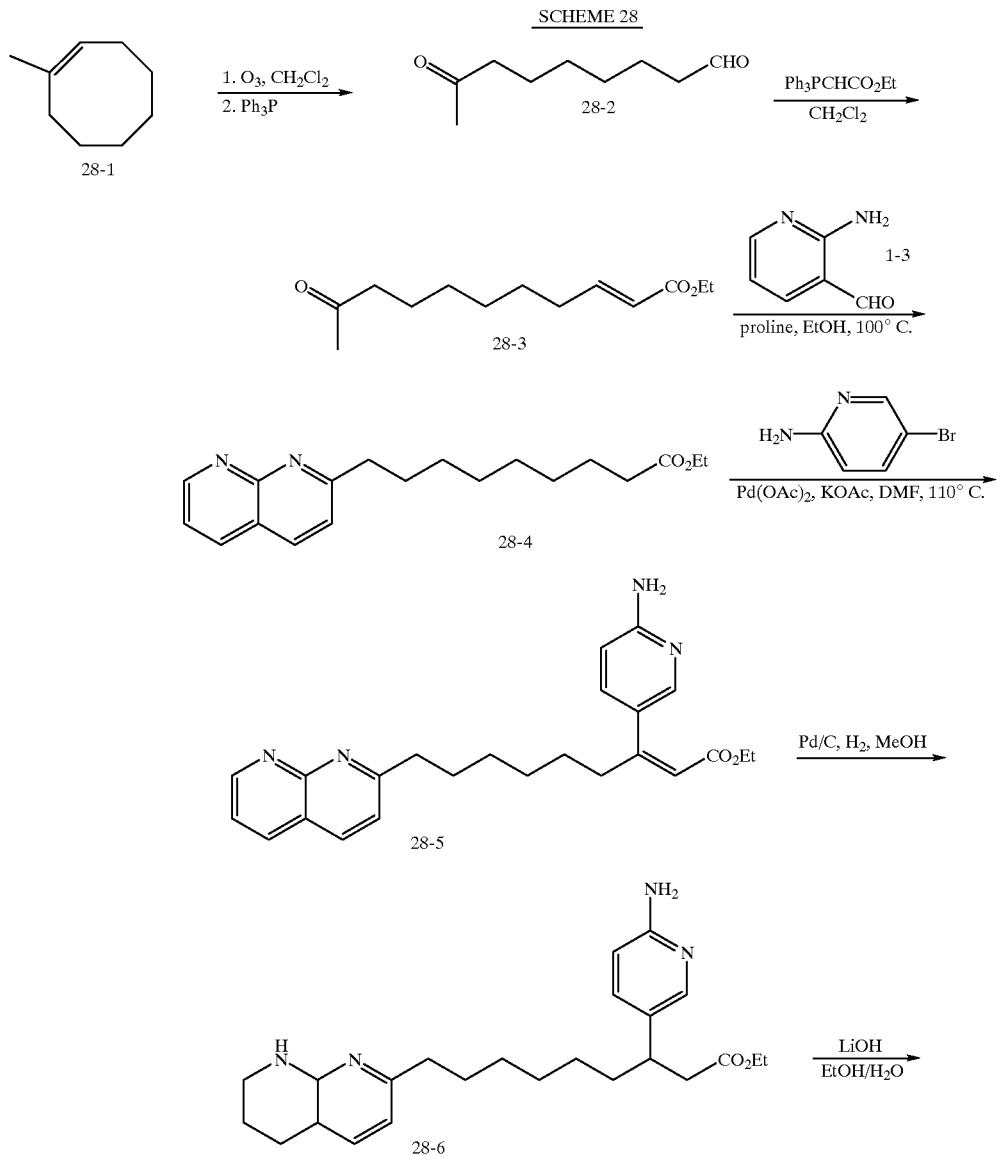

SCHEME 28

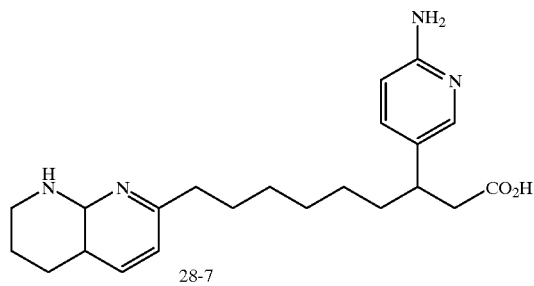

8-Oxo-nonanal (28-2)

To a cooled (−78° C.) solution of 1-methyl-cyclooctene 28-1 (5.2 g, 41.9 mmol) in 200 mL $CH_2Cl_2$ was introduced ozone for 30 min. The mixture was stirred for 1 hr and purged with argon. It was then treated with $Ph_3P$. The reaction mixture was concentrated and purified by silica gel flash chromatography (EtOAc/hexanxes 1:10) to afford the desired product 28-2 as an oil.

$^1$H NMR (400 MHz, $CDCl_3$) δ 9.72 (t, J=2.0 Hz, 1H), 2.38 (m, 4H), 2.09 (s, 3H), 1.61-1.52 (m, 4H), 1.28 (m, 4H).

10-Oxo-undec-2-enoic acid ethyl ester (28-3)

To a cooled (−40° C.) solution of 28-2 (10.8 g, 69.2 mmol) in 150 mL $CH_2Cl_2$ was added (carbethoxymethylene)triphenylphosphorane (24.1 g, 69.2 mmol) in 100 mL $CH_2Cl_2$ gradually over 15 min. The reaction mixture was stirred for 12 hr while it was warmed up to room temperature. After solvent removal, the residue was purified using silica gel flash chromatography (EtOAc/hexanes: 1:8 to 1:6) to afford the desired product 28-3 as an oil.

$^1$H NMR (400 MHz, $CDCl_3$) δ 6.95 (m, 1H), 5.80 (d, J=15.6 Hz, 1H), 4.18 (d, J=7.2 Hz, 2H), 2.42 (t, J=7.2 Hz, 2H), 2.20 (m, 2H), 2.13 (s, 3H), 1.57 (m, 2H), 1.46 (m, 2H), 1.29 (m, 7H).

9-[1,8]Naphthyridin-2-yl-non-2-enoic acid ethyl ester (28-4)

A mixture of 28-3 (4.1 g, 18.3 mmol), proline (2.7 g, 23.8 mmol), and 1-3 (2.9 g, 23.8 mmol ) in 50 mL EtOH was heated at 110° C. for 24 hr. The reaction mixture was concentrated and purified by silica gel chromatography (EtOAc, 100%) to afford the desired product 28-4 as a solid.

$^1$H NMR (400 MHz, $CDCl_3$) δ 9.08 (dd, J=4.4, 2.0 Hz, 1H), 8.15 (dd, J=8.0, 2.0 Hz, 1H), 8.09 (d, J=8.4 Hz, 1 H), 7.44 (dd, J=8.0, 4.4, 1H), 7.38 (d, J=8.4 Hz, 1H), 6.95 (dt, J=15.6, 7.2 Hz, 1H), 5.80 (dt, J=15.6, 1.6 Hz, 1H), 4.15 (q, J=7.2 Hz, 2H), 3.05 (t, J=7.6 Hz, 2H), 2.18 (m, 2H), 1.90 (m, 2H), 1.43 (m, 6H), 1.28 (t, J=7.2 Hz, 3H).

3-(6-Amino-pyridin-3-yl)-9-[1,8]naphthyridin-2-yl-non-2-enoic acid ethyl ester (28-5)

A mixture of 28-4 (0.3 g, 1.0 mmol), 2-amino-5-bromopyridine (0.3 g, 1.9 mmol), KOAc (0.3 g, 2.4 mmol) and $Pd(OAc)_2$ (0.02 g, 0.1 mmol) in 6 mL DMF was purged with argon for 5 min and then heated at 90° C. for 7 hr and 115° C. for 48 hr. It was cooled, treated with 50 mL water and extracted with EtOAc (×3). The combined organic layers were washed with brine and dried over $Na_2SO_4$. After solvent removal, the residue was purified using silica gel flash chromatography (100% EtOAc to EtOAc/MeOH 10:1) to afford the desired product 28-5 as an oil.

$^1$H NMR (400 MHz, $CDCl_3$) δ 9.07 (dd, J=4.4, 2.0 Hz, 1H), 8.18 (d, J=2.0 Hz, 1H), 8.14 (dd, J=8.0, 2.0 Hz, 1H), 8.07 (d, J=8.4 Hz, 1 H), 7.53 (dd, J=8.8, 2.0 Hz, 1H), 7.44 (dd, J=8.0, 4.4, 1H), 7.38 (d, J=8.4 Hz, 1H), 6.50 (d, J=8.8 Hz, 1H), 5.96 (s, 1H), 4.83 (bs, 2H), 4.18 (q, J=7.2 Hz, 2H), 3.02 (m, 4H), 1.85 (m, 2H), 1.43 (m, 6H), 1.29 (t, J=7.2 Hz, 3H).

3-(6-Amino-pyridin-3-yl)-9-(5,6,7,8-tetrahydro-[1,8]naphthyridin-2-yl)-nonanoic acid ethyl ester (28-6)

A mixture of 28-5 (0.1 g, 0.3 mmol) and 10% Pd/C (0.1 g) in 10 mL methanol was purged with argon under vacuum and then treated under balloon hydrogenation conditions for 40 hr. It was filtered through a pad of celite. The solution was concentrated. The residue was purified by silica gel chromatography (100% $CHCl_3$ to $CHCl_3$/MeOH 5:1) to afford the desired product 28-6 as an oil.

$^1$H NMR (400 MHz, $CDCl_3$) δ 7.88 (d, J=2.0 Hz, 1H), 7.25 (dd, J=8.4, 2.0 Hz, 1H), 7.05 (d, J=7.6 Hz, 1H), 6.45 (d, J=8.4 Hz, 1 H), 6.31 (d, J=7.6 Hz, 1H), 4.98 (bs, 1H), 4.34 (bs, 2H), 4.04 (q, J=7.2 Hz, 2H), 3.39 (m, 2H), 2.95 (m, 1H), 2.68 (m, 2H), 2.60-2.43 (m, 4H), 1.89 (m, 2H), 1.64-1.44 (m, 4H), 1.27 (m, 6H), 1.29 (t, J=7.2 Hz, 3H).

3-(6-Amino-pyridin-3-yl)-9-(5,6,7,8-tetrahydro-[1,8]naphthyridin-2-yl)-nonanoic acid (28-7)

A mixture of 28-6 (0.04 g, 0.1 mmol) and LiOH (1M, 0.3 mL, 0.3 mmol) in 1 mL EtOH and 0.5 mL $H_2O$ was stirred for 12 hr at room temperature. It was concentrated and diluted with 1N HCl (2 mL). The mixture was purified by reverse phase HPLC (C18 column; gradient: $H_2O/CH_3CN$/TFA from 95:5:0.1 to 5:95:0.1 over 45 min) to give pure 28-7 as the TFA salt.

$^1$H NMR (400 MHz, $CD_3OD$) δ 7.90 (dd, J=9.2, 2.0 Hz, 1H), 7.67 (d, J=2.0 Hz, 1H), 7.54 (d, J=7.6 Hz, 1H), 6.99 (d, J=9.2 Hz, 1 H), 6.55 (d, J=7.6 Hz, 1H), 3.48 (m, 2H), 3.00 (m, 1H), 2.80 (m, 2H), 2.66 (m, 5H), 2.53 (m, 1H), 1.94 (m, 2H), 1.64 (m, 4H), 1.27 (m, 4H).

SCHEME 29
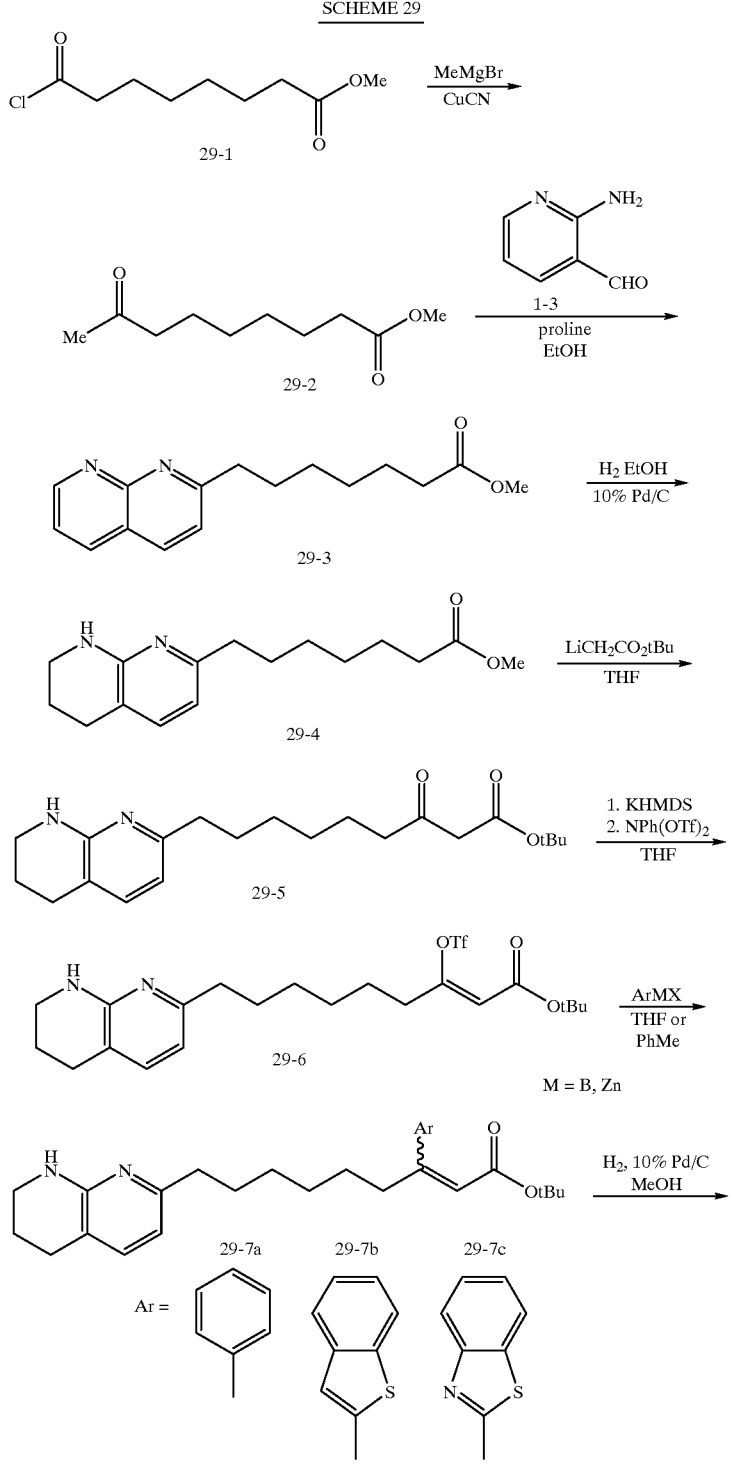

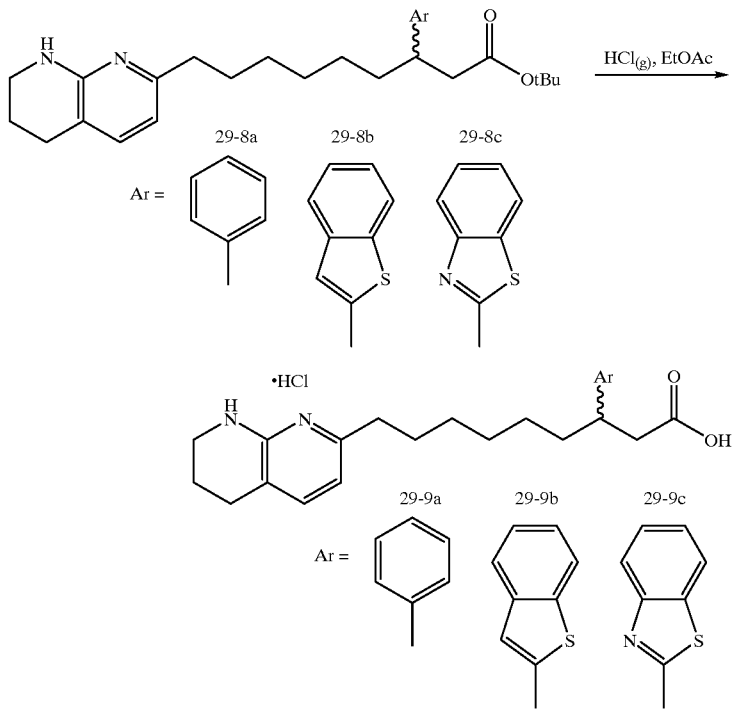

Methyl 8-oxo-nonanoate (29-2)

To a stirred suspension of cuprous cyanide (2.87 g, 32.0 mmol) in tetrahydrofuran (100 mL) at −78° C. was added a solution of methylmagnesium bromide (9.9 mL of a 3.0 M solution in tetrahydrofuran). The reaction mixture was allowed to warm to −15° C. for 5 minutes and then cooled to −78° C. To this was added a solution of methyl 7-(chloroformyl)-heptanoate 29-1 (4.9 g, 23.7 mmol) in tetrahydrofuran (20 mL) and the reaction mixture was allowed to warm to −10° C. for 1.5 hours. To the mixture was added a 9:1 solution of saturated aqueous ammonium chloride and concentrated aqueous ammonium hydroxide (200 mL) and the resulting mixture was extracted with ethyl acetate (2×200 mL). The organic extracts were washed successively with saturated aqueous ammonium chloride, saturated aqueous sodium hydrogen carbonate, and saturated aqueous sodium chloride. The organic extracts were then dried with anhydrous magnesium sulfate, filtered, and concentrated at reduced pressure to give 29-1 as an oil which was used in the next step without further purification.

7-[1,8]Naphthyridin-2-yl-heptanoic acid methyl ester (29-3)

To a stirred solution of methyl 8-oxo-nonanoate 29-2 (3.8 g, 20.4 mmol) in absolute ethanol (100 mL) was added 2-aminopyridine-3-carboxaldehyde (2.49 g, 20.4 mmol) and L-proline (1.17 g, 10.2 mmol) and the mixture was heated to 95° C. for 18 hours, after which the mixture was cooled to ambient temperature and then concentrated at reduced pressure. The resulting solid was purified by flash column chromatography over silica gel with 95:5 ethyl acetate/methanol to give 29-3 as a white solid.

$^1$H NMR (300 MHz, CDCl$_3$) δ 9.11 (dd, J=2.0, 4.2 Hz, 1 H), 8.17 (dd, J=1.9, 8.1 Hz, 1 H), 8.14 (d, J=8.4 Hz, 1H), 7.44 (dd, J=4.4, 8.1 Hz, 1H), 7.39 (d, J=8.3 Hz, 1H), 3.65 (s, 3H), 3.03 (app t, J=6.2 Hz, 2H), 2.32 (app t, J=7.7 Hz, 2H), 1.98-1.84 (m, 2H), 1.70-1.57 (m, 2H), 1.50-1.33 (m, 4H).

7-(5,6,7,8-Tetrahydro-[1,8]naphthyridin-2-yl)-heptanoic acid methyl ester (29-4)

To a stirred suspension of 10% palladium on carbon (600 mg) in ethanol (25 mL) was added a solution of 7-[1,8] naphthyridin-2-yl-heptanoic acid methyl ester 29-3 (3.6 g) in ethanol (75 mL) and the mixture was subjected to an atmosphere of hydrogen for 18 hours. The reaction mixture was filtered through Celite and concentrated at reduced pressure to give 29-4 as an oil.

$^1$H NMR (300 MHz, CDCl$_3$) δ 7.06 (d, J=7.3 Hz, 1H), 6.33 (d, J=7.3 Hz, 1H), 5.01 (br s, 1H), 3.66 (s, 3H), 3.42-3.37 (m, 2H), 2.69 (app t, J=6.3 Hz, 2H), 2.53 (app t, J=7.6 Hz, 2H), ), 2.29 (app t, J=7.5 Hz, 2H), 1.94-1.86 (m, 2H), 1.67-1.59 (m, 2H), 1.37-1.33 (m, 4H).

3-Oxo-9-(5,6,7,8-tetrahydro-[1,8]naphthyridin-2-yl)-nonanoic acid tert-butyl ester (29-5)

To a stirred solution of diisopropylamine (5.17 mL, 36.9 mmol) in anhydrous tetrahydrofuran (100 mL) at −78° C. was added a solution of n-butyllithium in hexanes (16.2 mL of a 2.5 M solution). After 5 minutes, t-butyl acetate (4.97 mL, 36.9 mmol) was added. After an additional 5 minutes, 7-(5,6,7,8-tetrahydro-[1,8]naphthyridin-2-yl)-heptanoic acid methyl ester 29-4 (3.4 g, 12.3 mmol) in tetrahydrofuran (30 mL) was added and the solution was warmed to −40° C. for one hour. The reaction mixture was then poured into saturated aqueous sodium hydrogen carbonate, and extracted with ethyl acetate. The organic layer was washed with saturated aqueous sodium chloride, dried with anhydrous magnesium sulfate, filtered, and concentrated at reduced pressure. The resulting oil was purified by flash column chromatography over silica gel with ethyl acetate to give 29-5 as a yellowish oil.

$^1$H NMR (300 MHz, CDCl$_3$) δ 7.04 (d, J=7.3 Hz, 1H), 6.33 (d, J=7.3 Hz, 1H), 4.84 (br s, 1H), 3.42-3.37 (m, 2H), 3.33 (s, 2H), 2.69 (app t, J=6.4 Hz, 2H), 2.58-2.44 (m, 2H), 1.94-1.86 (m, 2H), 1.72-1.52 (m, 4H), 1.47 (s, 9H), 1.39-1.28 (m, 4H).

9-(5,6,7,8-Tetrahydro-[1,8]naphthyridin-2-yl)-3-(trifluoromethanesulfonyloxy)-non-2-enoic acid tert-butyl ester (29-6)

To a stirred solution of 3-oxo-9-(5,6,7,8-tetrahydro-[1,8]naphthyridin-2-yl)-nonanoic acid tert-butyl ester 2-95 (1.0 g, 2.77 mmol) in anhydrous tetrahydrofuran (25 mL) at 0° C. was added a solution of potassium bis(trimethylsilyl)amide in toluene (7.2 mL of a 0.5 M solution). After 5 minutes, N-phenyltrifluoromethanesulfonimide (1.49 g, 4.17 mmol) was added in one portion and the resulting solution was allowed to warm to ambient temperature for 2 hours. The reaction mixture was then poured into saturated aqueous sodium hydrogen carbonate and extracted with ethyl acetate. The organic layer was washed with saturated aqueous sodium chloride, dried with anhydrous magnesium sulfate, filtered, and concentrated at reduced pressure. The resulting oil was purified by flash column chromatography over silica gel with 3:2 ethyl acetate/hexanes to give 29-6 as a yellowish semi-solid.

$^1$H NMR (300 MHz, CDCl$_3$) δ 7.08 (d, J=7.3 Hz, 1H), 6.34 (d, J=7.3 Hz, 1H), 5.66 (s, 1H), 5.09 (br s, 1H), 3.44-3.37 (m, 2H), 2.68 (app t, J=6.2 Hz, 2H), 2.56 (app t, J=7.7 Hz, 2H), ), 2.33 (app t, J=7.6 Hz, 2H), 1.94-1.83 (m, 2H), 1.70-1.48 (m, 4H), 1.49 (s, 9H), 1.37-1.29 (m, 4H).

3-Phenyl-9-(5,6,7,8-tetrahydro-[1,8]naphthyridin-2-yl)-non-2-enoic acid tert-butyl ester (29-7a)

To a stirred solution of 9-(5,6,7,8-Tetrahydro-[1,8]naphthyridin-2-yl)-3-(trifluoromethanesulfonyloxy)-non-2-enoic acid tert-butyl ester 29-6 (100 mg, 0.20 mmol) in toluene (2.5 mL) was added palladium(tetrakis)-triphenylphosphine (23 mg, 0.020 mmol), phenylboronic acid (50 mg, 0.41 mmol), and potassium carbonate (56 mg, 0.41 mmol). The resulting suspension was heated at 90–100° C. for 2 hours, and then was allowed to cool to ambient temperature. The reaction mixture was then poured into saturated aqueous sodium hydrogen carbonate and extracted with ethyl acetate. The organic layer was washed with saturated aqueous sodium chloride, dried with anhydrous magnesium sulfate, filtered, and concentrated at reduced pressure. The resulting oil was purified by flash column chromatography over silica gel with 4:1 ethyl acetate/hexanes to give 29-7a as a colorless oil.

$^1$H NMR (300 MHz, CDCl$_3$) δ 7.41-7.15 (m, 5H), 7.02 (d, J=7.3 Hz, 1H), 6.31 (d, J=7.2 Hz, 1H), 5.77 (br s, 1H), 4.77 (br s, 1H), 3.42-3.34 (m, 2H), 2.69 (app t, J=6.3 Hz, 2H), 2.50 (app t, J=7.6 Hz, 2H), 2.39 (app t, J=7.8 Hz, 2H), 1.95-1.84 (m, 2H), 1.66-1.54 (m, 4H), 1.42-1.26 (m, 8H), 1.21 (s, 9H).

3-Phenyl-9-(5,6,7,8-tetrahydro-[1,8]naphthyridin-2-yl)-nonanoic acid tert-butyl ester (29-8a)

To a stirred suspension of 10% palladium on carbon (15 mg) in ethanol (2 mL) was added a solution of 3-phenyl-9-(5,6,7,8-tetrahydro-[1,8]naphthyridin-2-yl)-non-2-enoic acid tert-butyl ester 29-7a (62 mg) in ethanol (3 mL) and the mixture was subjected to an atmosphere of hydrogen for 6 hours. The reaction mixture was filtered through Celite and concentrated at reduced pressure to give 29-8a as an oil.

$^1$H NMR (300 MHz, CDCl$_3$) d 7.31-7.13 (m, 5H), 7.04 (d, J=7.3 Hz, 1H), 6.31 (d, J=7.2 Hz, 1H), 4.92 (br s, 1H), 3.42-3.35 (m, 2H), 3.06-2.94 (m, 1H), 2.69 (app t, J=6.2 Hz, 2H), 2.58-2.40 (m, 4H), 1.94-1.85 (m, 2H), 1.66-1.48 (m, 4H), 1.36-1.18 (m, 17H).

3-Phenyl-9-(5,6,7,8-tetrahydro-[1,8]naphthyridin-2-yl)-nonanoic acid hydrochloride (29-9a)

Hydrogen chloride gas was bubbled into a stirred solution of 3-phenyl-9-(5,6,7,8-tetrahydro-[1,8]naphthyridin-2-yl)-nonanoic acid tert-butyl ester 29-8a (60 mg) in ethyl acetate at 0° C. for one hour. The reaction mixture was allowed to warm to ambient temperature and then concentrated at reduced pressure. The resulting solid 29-9a was dried in vacuo overnight.

$^1$H NMR (300 MHz, CD$_3$OD) δ 7.78 (d, J=7.1 Hz, 1H), 7.33-7.11 (m, 5H), 6.58 (d, J=7.2 Hz, 1H), 3.52-3.42 (m, 2H), 3.10-2.96 (m, 1H), 2.82 (app t, J=7.0 Hz, 2H), 2.68-2.43 (m, 4H), 1.98-1.89 (m, 2H), 1.76-1.50 (m, 4H), 1.40-1.05 (m, 8H).

3-(benzo[b]thiophen-2-yl)-9-(5,6,7,8-tetrahydro-[1,8]naphthyridin-2-yl)-non-2-enoic acid tert-butyl ester (29-7b)

To a stirred solution of 9-(5,6,7,8-tetrahydro-[1,8]naphthyridin-2-yl)-3-(trifluoromethanesulfonyloxy)-non-2-enoic acid tert-butyl ester 29-6 (100 mg, 0.20 mmol) in toluene (2.5 mL) was added palladium(tetrakis)-triphenylphosphine (23 mg, 0.020 mmol), benzo[b]thiophene-2-boronic acid (50 mg, 0.41 mmol) and potassium carbonate (56 mg, 0.41 mmol). The resulting suspension was heated at 90–100° C. for 2 hours, and then was allowed to cool to ambient temperature. The reaction mixture was then poured into saturated aqueous sodium hydrogen carbonate and extracted with ethyl acetate. The organic layer was washed with saturated aqueous sodium chloride, dried with anhydrous magnesium sulfate, filtered, and concentrated at reduced pressure. The resulting oil was purified by flash column chromatography over silica gel with 4:1 ethyl acetate/hexanes to give 29-7b as a colorless oil.

$^1$H NMR (300 MHz, CDCl$_3$) δ 7.82-7.70 (m, 2H), 7.53 (s, 1H), 7.39-7.22 (m, 2H), 7.02 (d, J=7.3 Hz, 1H), 6.33 (d, J=7.3 Hz, 1H), 5.89 (br s, 1H), 4.78 (br s, 1H), 3.42-3.36 (m, 2H), 2.74 (app t, J=6.2 Hz, 2H), 2.58-2.42 (m, 2H), 1.95-1.77 (m, 4H), 1.70-1.10 (m, 17H).

3-(Benzo[b]thiophen-2-yl)-9-(5,6,7,8-tetrahydro-[1,8]naphthyridin-2-yl)-nonanoic acid tert-butyl ester (29-8b)

To a stirred suspension of 10% palladium on carbon (45 mg) in methanol (5 mL) was added a solution of 3-(benzo[b]thiophen-2-yl)-9-(5,6,7,8-tetrahydro-[1,8]naphthyridin-2-yl)-non-2-enoic acid tert-butyl ester 29-7b (220 mg) in ethanol (5 mL) and the mixture was subjected to an atmosphere of hydrogen for 48 hours. The reaction mixture was filtered through Celite and concentrated at reduced pressure. The resulting oil was purified by flash column chromatography over silica gel with 9:1 ethyl acetate/methanol to give 29-8b as a colorless oil.

$^1$H NMR (300 MHz, CDCl$_3$) δ 7.89-7.64 (m, 4H),7.03 (s, 1H), 7.02 (d, J=7.3 Hz, 1H), 6.29 (d, J=7.3 Hz, 1H), 4.85 (br s, 1H), 3.44-3.34 (m, 3H), 2.72-2.44 (m, 6H), 1.94-1.84 (m, 2H), 1.72-1.52 (m, 4H), 1.34 (s, 9H), 1.33-1.22 (m, 8H).

3-(Benzo[b]thiophen-2-yl)-9-(5,6,7,8-tetrahydro-[1,8]naphthyridin-2-yl)-nonanoic acid (29-9b)

Hydrogen chloride gas was bubbled into a stirred solution of 3-(benzo[b]thiophen-2-yl)-9-(5,6,7,8-tetrahydro-[1,8]naphthyridin-2-yl)-nonanoic acid tert-butyl ester 29-8b (85 mg) in ethyl acetate at 0° C. for one hour. The reaction mixture was allowed to warm to ambient temperature and then concentrated at reduced pressure. The resulting solid was neutralized with concentrated ammonium hydroxide, then the resulting free base was purified by flash column chromatography over silica gel with 25:3:2 chloroform/ethyl acetate/methanol to give 29-9b as a colorless oil.

$^1$H NMR (300 MHz, CD$_3$OD) d 7.77-7.62 (m, 2H), 7.38 (d, J=7.3 Hz, 1H), 7.30-7.18 (m, 2H), 7.09 (s, 1H), 6.45 (d, J=7.2 Hz, 1H),3.60-3.51 (m, 1H), 3.41 (app t, J=6.4 Hz, 2H),2.78-2.52 (m, 6H), 1.94-1.56 (m, 8H), 1.44-1.28 (m, 8H).

3-(Benzothiazol-2-yl)-9-(5,6,7,8-tetrahydro-[1,8]naphthyridin-2-yl)-non-2-enoic acidtert-butyl ester (29-7c)

To a stirred solution of benzthiazole (165 mg, 1.22 mmol) in anhydrous tetrahydrofuran (5 mL) at −78° C. was added a solution of n-butyllithium in hexanes (0.52 mL of a 2.5 M solution). After 5 minutes, a solution of zinc chloride in tetrahydrofuran (2.6 mL of a 0.50 M solution) was added and the reaction mixture was allowed to warm to ambient temperature. To the resulting solution was added 9-(5,6,7,8-tetrahydro-[1,8]naphthyridin-2-yl)-3-(trifluoromethanesulfonyloxy)-non-2-enoic acid tert-butyl ester 29-6 (400 mg, 0.81 mmol) and palladium(tetrakis)-triphenylphosphine (94 mg, 0.081 mmol) and the mixture was stirred at ambient temperature for 1 hour. The reaction mixture was then poured into saturated aqueous sodium hydrogen carbonate and extracted with ethyl acetate. The organic layer was washed with saturated aqueous sodium chloride, dried with anhydrous magnesium sulfate, filtered, and concentrated at reduced pressure. The resulting oil was purified by flash column chromatography over silica gel with 4:1 ethyl acetate/hexanes to give 29-7c as a colorless oil.

$^1$H NMR (300 MHz, CDCl$_3$): δ 8.10-7.85 (m, 2H), 7.50-7.35 (m, 2H), 7.02 (d, J=7.2 Hz, 1H), 6.35 (d, J=7.2 Hz, 1H), 6.05 (br s, 1H), 5.55 (br s, 1H), 3.45-3.36 (m, 2H), 2.74-2.65 (m, 2H), 2.62-2.42 (m, 2H), 2.28 (app t, J=7.2 Hz, 2H), 1.95-1.82 (m, 2H), 1.70-1.15 (m, 17H).

3-(Benzothiazol-2-yl)-9-(5,6,7,8-tetrahydro-[1,8]naphthyridin-2-yl)-nonanoic acid tert-butyl ester (29-8c)

To a stirred suspension of 10% palladium on carbon (50 mg) in methanol (5 mL) was added a solution of 3-(benzothiazol-2-yl)-9-(5,6,7,8-tetrahydro-[1,8]naphthyridin-2-yl)-non-2-enoic acidtert-butyl ester 29-7c (190 mg) in ethanol (5 mL) and the mixture was subjected to an atmosphere of hydrogen for 48 hours. The reaction mixture was filtered through Celite and concentrated at reduced pressure. The resulting oil was purified by flash column chromatography over silica gel with 4:1 hexanes/acetone to give 29-8c as a colorless oil.

$^1$H NMR (300 MHz, CDCl$_3$) δ 7.99-7.81 (m, 2H), 7.48-7.31 (m, 2H), 7.04 (d, J=7.3 Hz, 1H), 6.30 (d, J=7.2 Hz, 1H), 4.95 (br s, 1H), 3.66-3.56 (m, 1H), 3.38 (app t, J=6.3 Hz, 2H), 2.90-2.63 (m, 6H), 2.48 (app t, J=7.6 Hz, 2H), 1.94-1.74 (m, 4H), 1.64-1.52 (m, 2H), 1.36 (s, 9H), 1.34-1.22 (m, 8H).

3-(Benzothiazol-2-yl)-9-(5,6,7,8-tetrahydro-[1,8]naphthyridin-2yl)-nonanoic acid hydrochloride (29-9c)

Hydrogen chloride gas was bubbled into a stirred solution of 3-(benzothiazol-2-yl)-9-(5,6,7,8-tetrahydro-[1,8] naphthyridin-2-yl)-nonanoic acid tert-butyl ester 29-9b (80 mg) in ethyl acetate at 0° C. for one hour. The reaction mixture was allowed to warm to ambient temperature and then concentrated at reduced pressure. The resulting solid 29-9c was pumped in vacuo overnight.

$^1$H NMR (300 MHz, CD$_3$OD) δ 8.01-7.90 (m, 2H), 7.60-7.41 (m, 3H), 6.58 (d, J=7.3 Hz, 1H), 3.78-3.62 (m, 1H), 3.49 (app t, J=6.4 Hz, 2H), 2.98-2.59 (m, 6H), 1.97-1.82 (m, 4H), 1.70-1.56 (m, 2H), 1.44-1.28 (m, 6H).

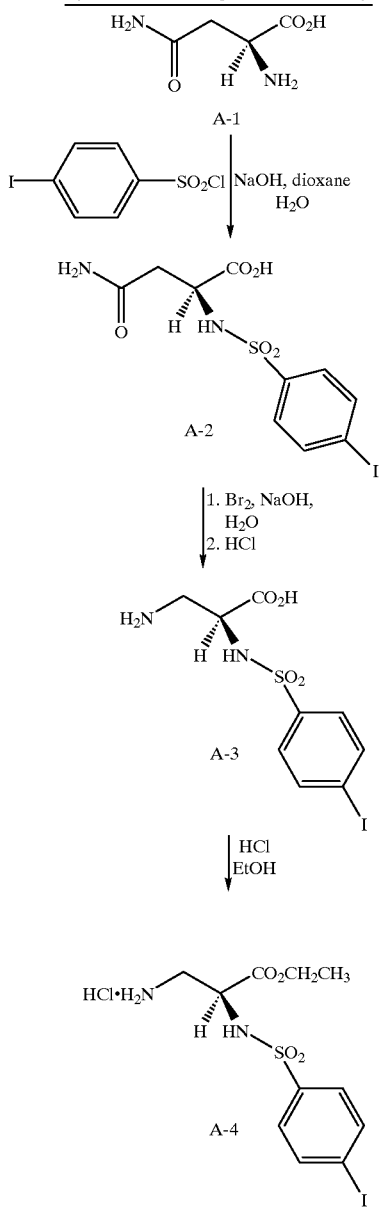

SCHEME A
Synthesis of Radioligand for SPA Assay

111

-continued

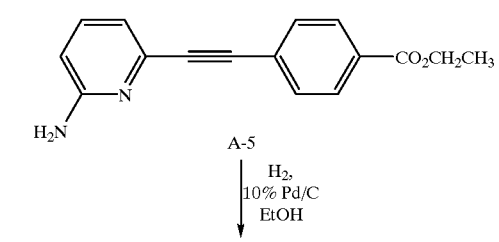

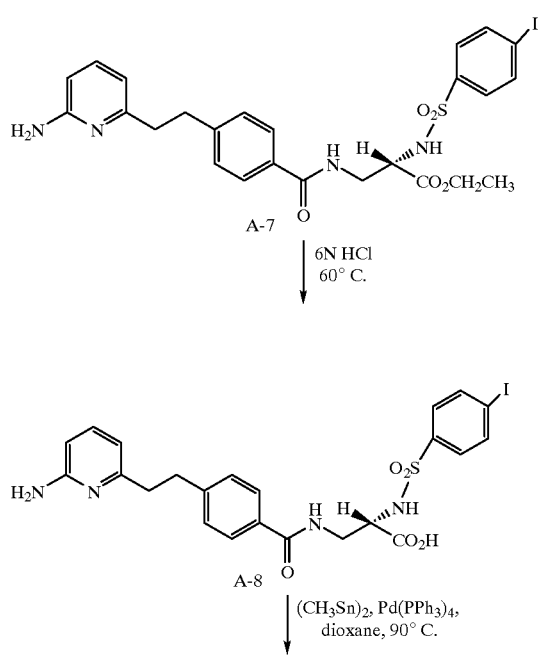

112

-continued

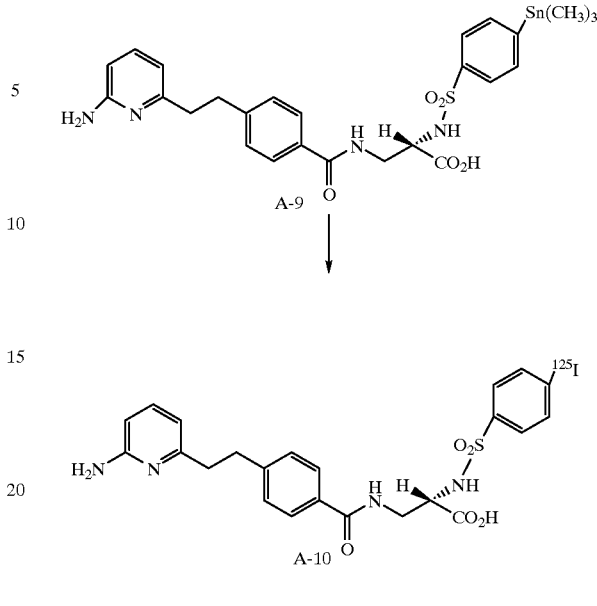

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and $H_2O$ (30 ml) at 0° C. was added pipsyl chloride (10.34 g, 34.2 mmol). After ~5 minutes, NaOH (1.49, 37.2 mmol) dissolved in 15 ml $H_2O$, was added followed by the removal of the cooling bath. After 2.0 h, the reaction mixture was concentrated. The residue was dissolved in $H_2O$ (300 ml) and then washed with EtOAc. The aqueous portion was cooled to 0° C. and then acidified with concentrated HCl. The solid was collected and then washed with $Et_2O$ to provide acid A-2 as a white solid.

$^1$H NMR (300 MHz, $D_2O$) δ 7.86 (d, 2H, J=8 Hz ), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and $H_2O$ (40 ml) at 0° C. was added $Br_2$ (1.30 ml 24.9 mmol) dropwise over a ten minute period. After ~5 minutes, acid A-2 (9.9 g, 24.9 mmol), NaOH (2.00 g, 49.8 mmol) and $H_2O$ (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, $D_2O$) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, CD$_3$OD) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm H$_2$. After 20 h, the reaction was filtered through a celite pad and then concentrated to provide ester A-5a as a brown oil.

TLC R$_f$=0.23 (silica, 40% EtOAc/hexanes)

$^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, CD$_3$OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[$^2$-($^2$-Aminopyridin-6-yl)ethyl]benzoyl-2(S)-(4-iodophenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. NaHCO$_3$, brine, dried (MgSO$_4$) and concentrated. Flash chromatography (silica, EtOAc then 5% isopropanol/EtOAc) provided amide A-7 as a white solid.

TLC R$_f$=0.4 (silica, 10% isopropanol/EtOAc)

$^1$H NMR (300 MHz, CD$_3$OD) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/NH$_4$OH/H$_2$O) provided acid A-8 as a white solid.

TLC R$_f$=0.45 (silica, 20:20:1:1 EtOAc/EtOH/NH$_4$OH/H$_2$O)

$^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl]benzoyl-2(S)-(4-trimethylstannylphenylsulfonylamino-β-alanine (A-9)

A solution of iodide A-8 (70 mg, 0.1178 mmol), [(CH$_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak C$_{18}$ 15 μM 100 A°, 40×100 mm; 95:5 then 5:95 H$_2$O/CH$_3$CN) to provide the trifluoroacetate salt. The salt was suspended in H$_2$O (10 ml), treated with NH$_4$OH (5 drops) and then lyophilized to provide amide A-9 as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95-7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodophenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

The following additional but non-limiting examples were prepared using the procedures described above and are accompanied by their mass spectral characterization data:

| Compound No. | Compound Name | MS* |
|---|---|---|
| (1) | 3(R)-(Quinolin-3-yl)-3-(5-(5,6,7,8-tetrahydro-[1,8]naphthyridin-2-yl)-pentanoylamino)-propionic acid; | 433 |

-continued

| Compound No. | Compound Name | MS* |
|---|---|---|

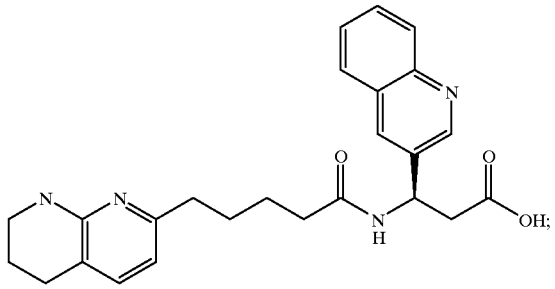

| (2) | 3-(Quinolin-3-yl)-3-(7-(5,6,7,8-tetrahydro-[1,8]naphthyridin-2-yl)-heptanoylamino)-propionic acid bis(trifluoroacetate); | 461 |

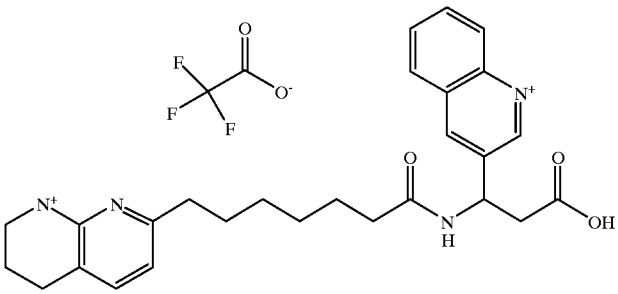

| (3) | 3-(Quinolin-3-yl)-3-(6-(5,6,7,8-tetrahydro-[1,8]naphthyridin-2-yl)-hexanoylamino)-propionic acid; | 447 |

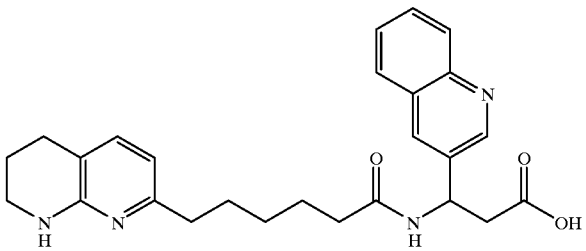

| (4) | 3(S)-(5-(5,6,7,8-tetrahydro-[1,8]naphthyridin-2-yl)-pentanoylamino)-pent-4-enoic acid; | 332 |

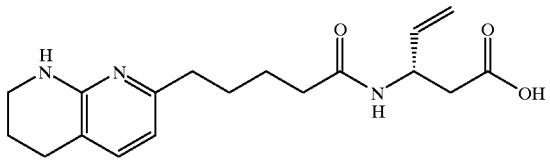

| (5) | 2-(3-Fluorophenyl)-3-(5-(5,6,7,8-tetrahydro-[1,8]naphthyridin-2-yl)-pentanoylamino)-propionic acid trifluoroacetate salt; | 400 |

-continued

| Compound No. | Compound Name | MS* |
|---|---|---|
| | 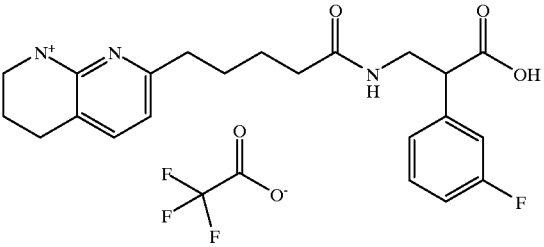 | |
| (6) | 3(S)-(2,3-Dihydro-benzofuran-6-yl)-3-[3-(5,6,7,8-tetrahydro-[1,8]-naphthyridin-2-ylmethylsulfanyl)propionylamino]-propionic acid bis(trifluoroacetate); | 442 |
| | 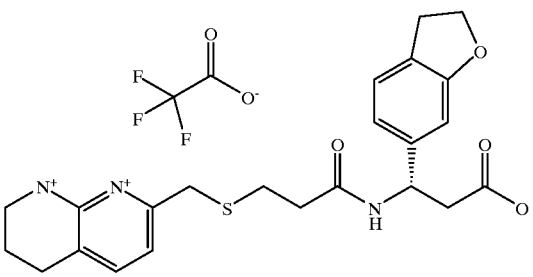 | |
| (7) | 2(S)-(Benzenesulfonylamino)-10-(5,6,7,8-tetrahydro-[1,8]naphthyridin-2-yl)-decanoic acid; | 460 |
| | 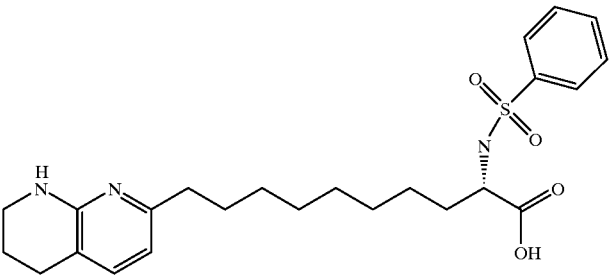 | |
| (8) | 2(S)-(Benzenesulfonylamino)-8-(5,6,7,8-tetrahydro-[1,8]naphthyridin-2-yl)-octanoic acid; | 432 |
| | 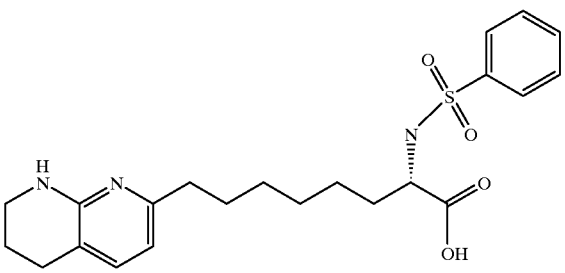 | |
| (9) | 2(S)-(Cyclohexylmethanesulfonylamino)-9-(5,6,7,8-tetrahydro-[1,8]naphthyridin-2-yl)-nonanoic acid hydrochloride; | 466 |

| Compound No. | Compound Name | MS* |
|---|---|---|
| | 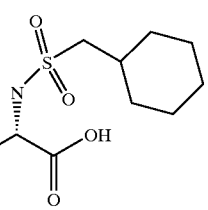 | |
| (10) | 2(S)-(7,7-Dimethyl-2-oxo-bicyclo[2.2.1]hept-1(S)-ylmethanesulfonylamino)-9-(5,6,7,8-tetrahydro-[1,8]naphthyridin-2-yl)-nonanoic acid hydrochloride; | 520 |
| | 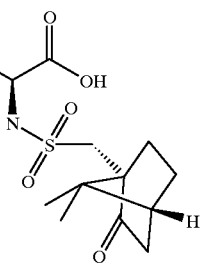 | |
| (11) | 2(S)-(Phenylmethanesulfonylamino)-9-(5,6,7,8-tetrahydro-[1,8]naphthyridin-2-yl)-nonanoic acid; | 460 |
| | 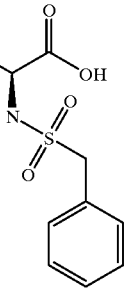 | |
| (12) | 2(S)-(Cyclohexanesulfonylamino)-9-(5,6,7,8-tetrahydro-[1,8]naphthyridin-2-yl)-nonanoic acid hydrochloride; | 452 |
| | 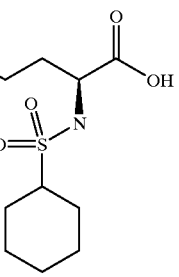 | |
| (13) | 2(S)-(3-Benzylureido)-9-(5,6,7,8-tetrahydro-[1,8]naphthyridin-2-yl)-nonanoic acid; | 439 |
| | 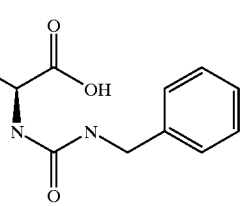 | |

-continued

| Compound No. | Compound Name | MS* |
|---|---|---|
| (14) | 2(S)-(Benzyloxycarbonylamino)-9-(5,6,7,8-tetrahydro-[1,8]naphthyridin-2-yl)-nonanoic acid; | 440 |

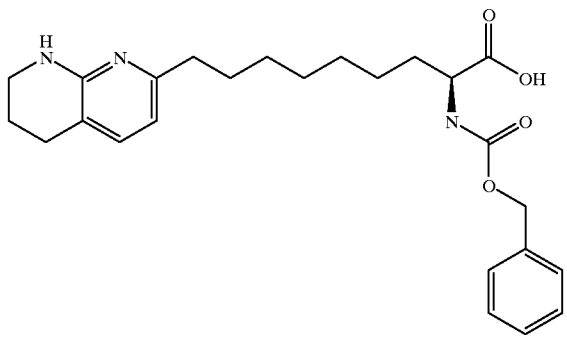

| | | |
|---|---|---|
| (15) | 2(S)-(Phenylacetylamino)-9-(5,6,7,8-tetrahydro-[1,8]naphthyridin-2-yl)-nonanoic acid; | 424 |

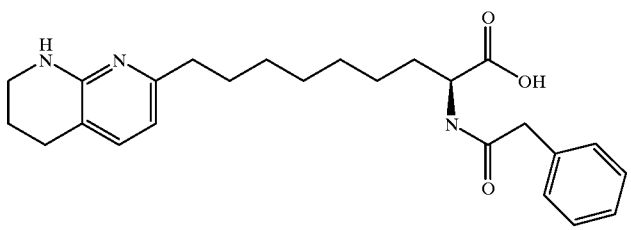

| | | |
|---|---|---|
| (16) | 2(S)-(Acetylamino)-9-(5,6,7,8-tetrahydro-[1,8]naphthyridin-2-yl)-nonanoic acid; | 348 |

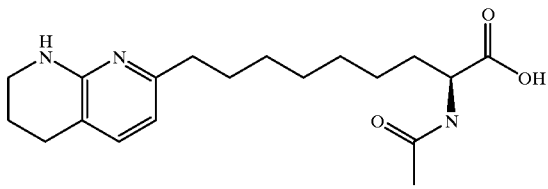

| | | |
|---|---|---|
| (17) | 2(S)-(Benzoylamino)-9-(5,6,7,8-tetrahydro-[1,8]naphthyridin-2-yl)-nonanoic acid; | 410 |

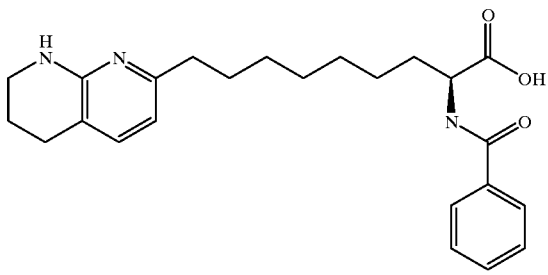

| | | |
|---|---|---|
| (18) | 3-(Quinolin-3-yl)-7-[acetyl-(5,6,7,8-tetrahydro-[1,8]-naphthyridin-2-ylmethyl)amino]-heptanoic acid; | 461 |

-continued
| Compound No. | Compound Name | MS* |
|---|---|---|
| | 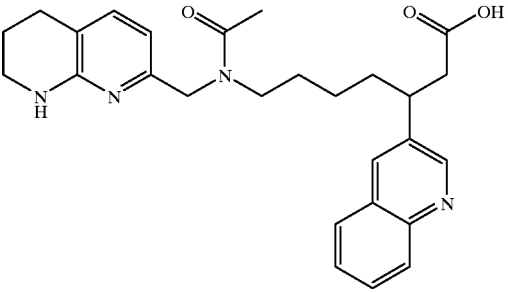 | |
| (19) | 3-(Quinolin-3-yl)-7-[methanesulfonyl-(5,6,7,8-tetrahydro-[1,8]-naphthyridin-2-ylmethyl)amino]-heptanoic acid; | 497 |
| | 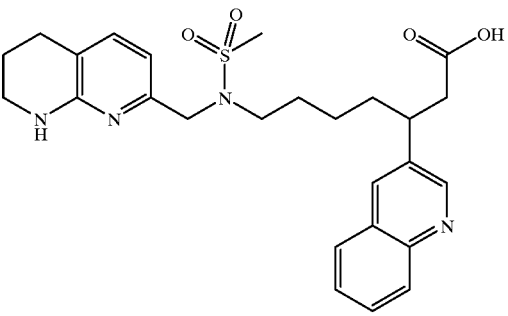 | |
| (20) | 3-(6-Oxo-1,6-dihydro-pyridin-3-yl)-9-(5,6,7,8-tetrahydro-[1,8]-naphthyridin-2-yl)-nonanoic acid bis-(trifluoroacetate); | 384 |
| | 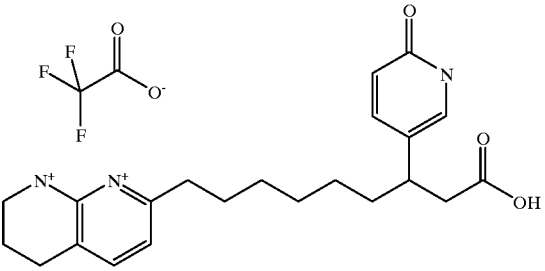 | |
| (21) | 3-(Quinolin-3-yl)-7-(1,2,3,4,6,7,8,9-octahydro-benzo[b][1,8]-naphthyridin-8-yl)-heptanoic acid bis(hydrochloride); | 444 |
| | 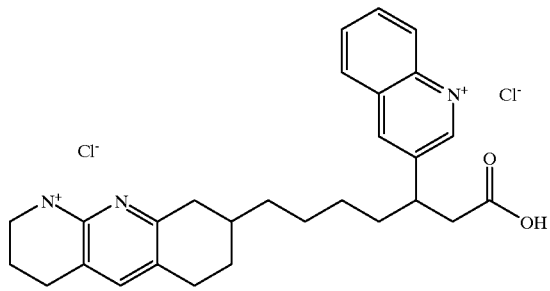 | |
| (22) | 3-(Pyridin-3-yl)-9-(5,6,7,8-tetrahydro-[1,8]-naphthyridin-2-yl)-nonanoic acid; | 368 |

-continued

| Compound No. | Compound Name | MS* |
|---|---|---|
| (23) | 3-(2,3-Dihydro-benzofuran-6-yl)-9-(5,6,7,8-tetrahydro-[1,8]-naphthyridin-2-yl)-non-4-enoic acid trifluoroacetate; | 407 |
| (24) | 2-(Benzenesulfonylamino)-9-(5,6,7,8-tetrahydro-[1,8]-naphthyridin-2-yl)-non-4-enoic acid bis(trifluoroacetate); | 444 |

*m/e, M⁺ or (M + 1)⁺

Compounds I–XXX whose structures are shown below can also be prepared as described above and depicted in Schemes 1–29 using synthetic methodologies or variations thereon which are known and understood by those skilled in the art of synthetic organic chemistry:

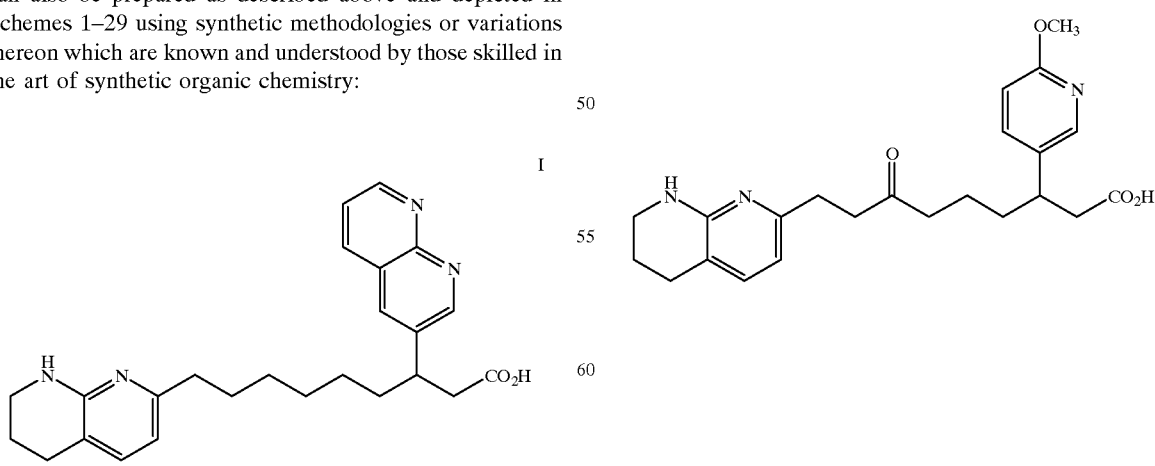

III
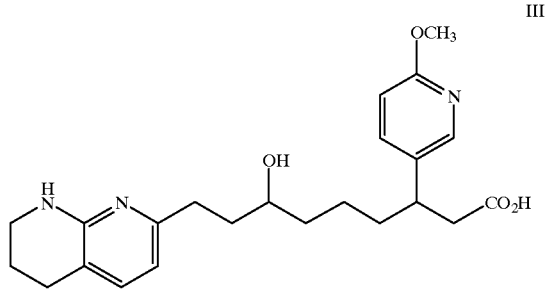
IV
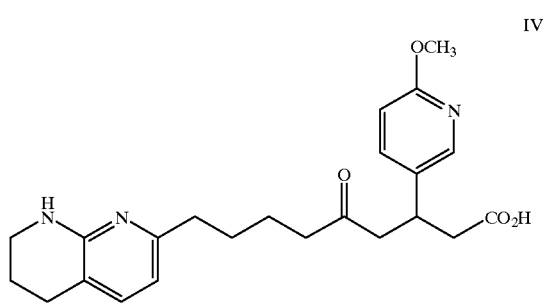
V
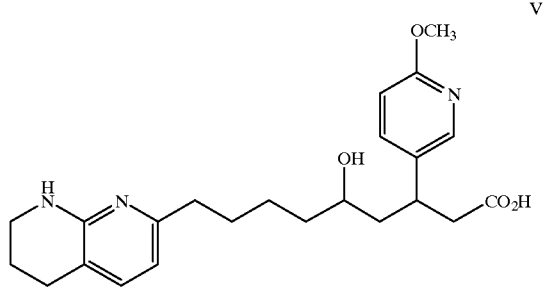
VI
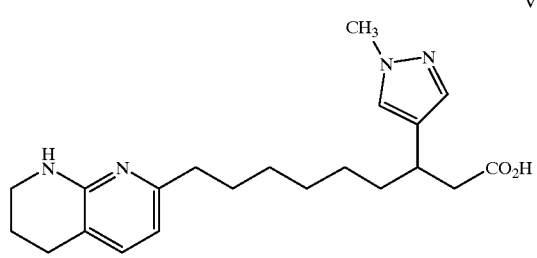
VII
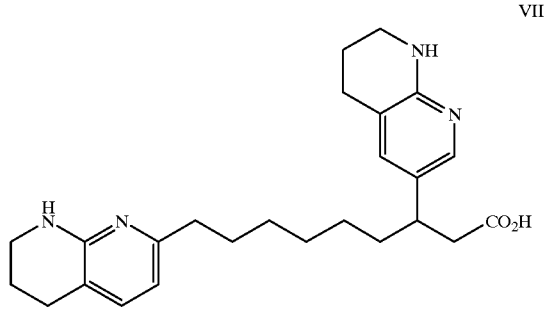
VIII
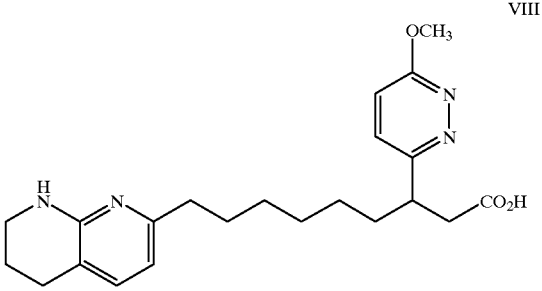
IX
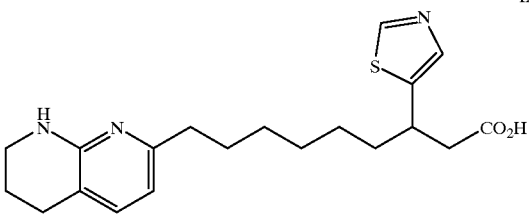
X
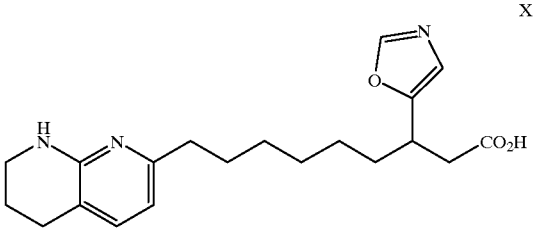
XI
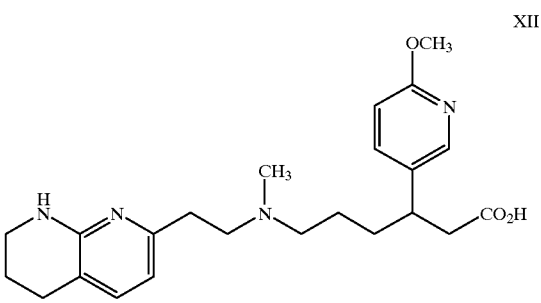
XII
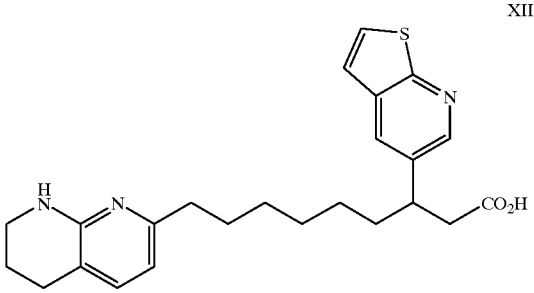
XIII XIV 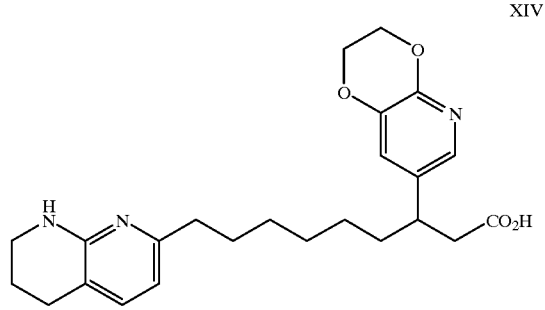
XV 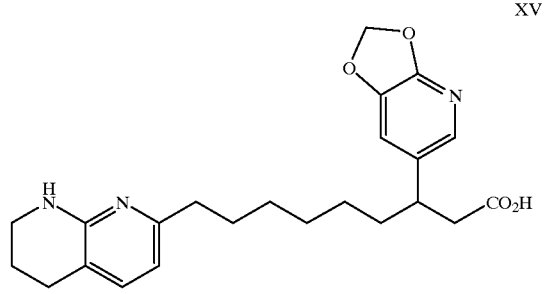
XVI 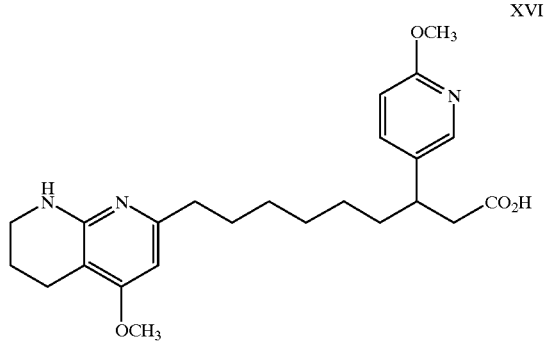
XVII 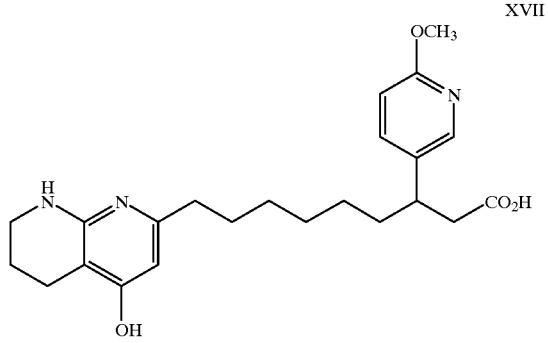
XVIII 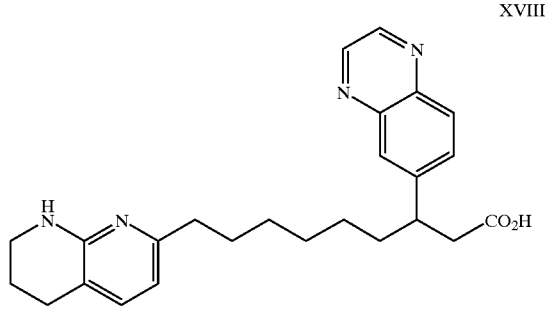
XIX 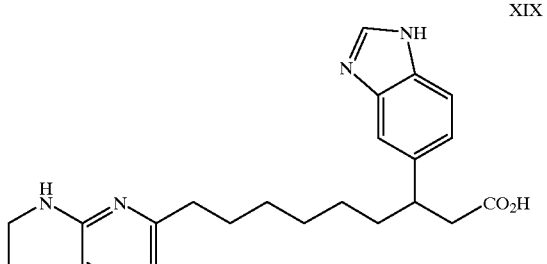
XX 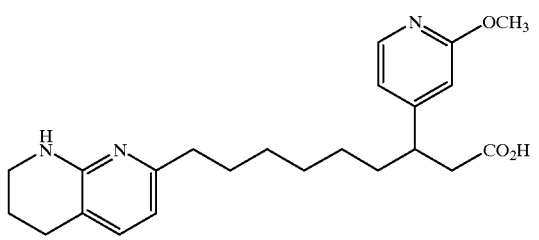
XXI 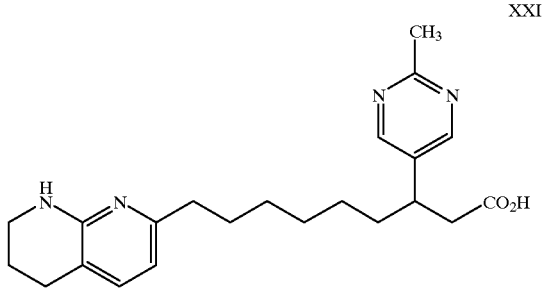
XII 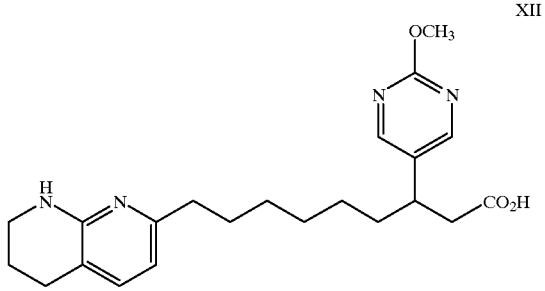
XXIII 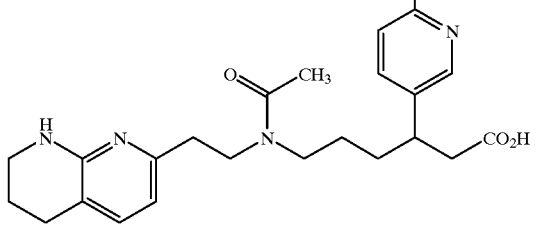

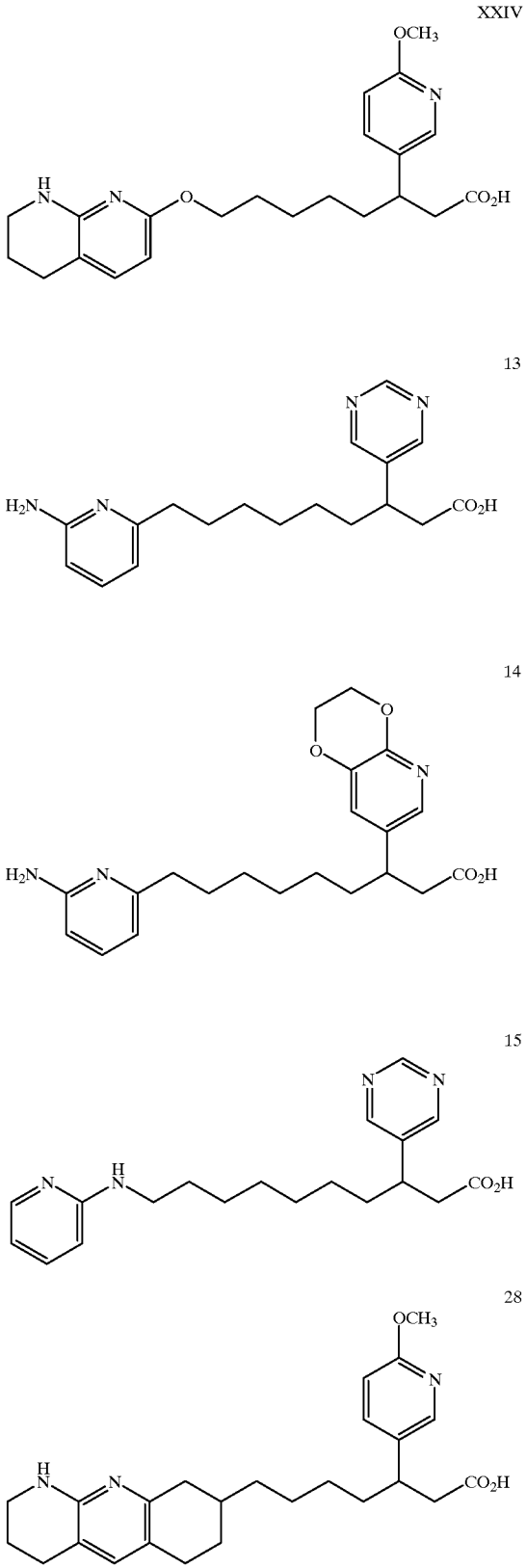

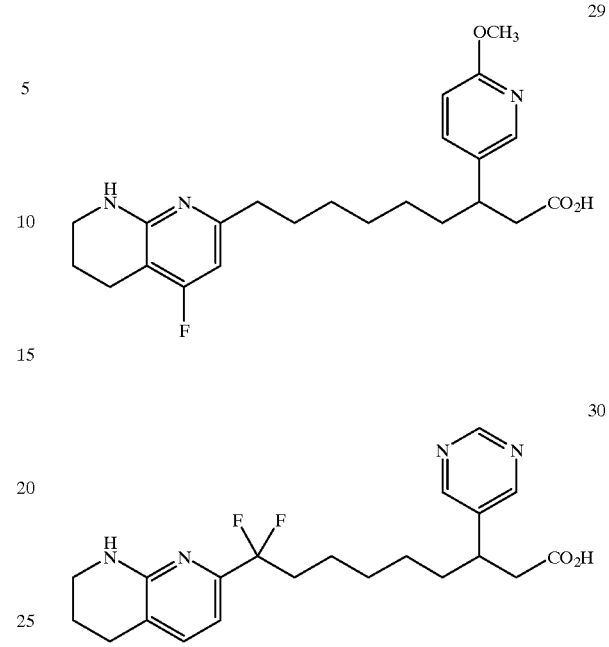

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure $\alpha v \beta 3$ and $\alpha v \beta 5$ binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2 \times 10^7$ cells/ml). A cell suspension consisting of $5 \times 10^6$/ml in αMEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 in ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8:S378 (1993), describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 μl TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 μl).
3. $^{125}$I-echistatin (25 μl/50,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% polyethyleneimine for 10 mins) were then washed with the wash buffer (50 mM Tris HCl, 1 mM $CaCl_2/MgCl_2$, pH 7.2). The filter was then counted in a gamma counter.

SPA ASSAY

Materials:
1. Wheat germ agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer

PROCEDURE

1. Pretreatment of SPA beads:

500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture

In each assay tube, 2.5 μl (40 mg/ml) of pretreated beads were suspended in 97.5 μl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:
(i) Receptor/beads mixture (75 μl)
(ii) 25 μl of each of the following: compound to be tested, binding buffer for total binding or A-8 for non-specific binding (final concentration 1 μM)
(iii) A-10 in binding buffer (25 μl, final concentration 40 pM)
(iv) Binding buffer (125 μl)

(v) Each plate was sealed with plate sealer from PACK-ARD and incubated overnight with rocking at 4° C.
4. Plates were counted using PACKARD TOPCOUNT
5. % inhibition was calculated as follows:

A=total counts
B=nonspecific counts
C=sample counts
% inhibition=[{(A−B)−(C−B)}/(A−B)]/(A−B)×100

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 μL was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h., the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

αvβ5 ATTACHMENT ASSAY

Duong et al., *J. Bone Miner. Res.*, 11:S290 (1996), describes a system for expressing the human αvβ5 integrin receptor.

Materials:
1. Media and solutions used in this assay are purchased from BRL/Gibco, except BSA and the chemicals are from Sigma.
2. Attachment medium: HBSS with 1 mg/ml heat-inactivated fatty acid free BSA and 2 mM $CaCl_2$.
3. Glucosaminidase substrate solution: 3.75 mM p-nitrophenyl N-acetyl-beta-D-glucosaminide, 0.1 M sodium citrate, 0.25% Triton, pH 5.0.
4. Glycine-EDTA developing solution: 50 mM glycine, 5 mM EDTA, pH 10.5.

Methods:
1. Plates (96 well, Nunc Maxi Sorp) were coated overnight at 4° C. with human vitronectin (3 μg/ml) in 50 mM carbonate buffer (pH 9/0.6), using 100 μl/well. Plates were then washed 2× with DPBS and blocked with 2% BSA in DPBS for 2 h at room temperature. After additional washes (2×) with DPBS, plates were used for cell attachment assay.
2. 293 (αvβ5) cells were grown in αMEM media in presence of 10% fetal calf serum to 90% confluence. Cells were then lifted from dishes with 1× Trypsin/EDTA and washed 3× with serum free αMEM. Cells were resuspended in attachment medium ($3 \times 10^5$ cells/ml).
3. Test compounds were prepared as a series of dilutions at 2× concentrations and added as 50 μl/well. Cell suspension was then added as 50 ml/well. Plates were incubated at 37° C. with 55 $CO_2$ for 1 hour to allow attachment.
4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.
5. The next day, the reaction was developed by addition of 185 μl/well of glycine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

EXAMPLE OF A PHARMACEUTICAL FORMULATION

As a specific embodiment of an oral composition, 100 mg of any of the compounds of the present invention are formulated with sufficient finely divided lactose to provide a total amount of 580 to 590 mg to fill a size O hard gel capsule.

Representative compounds of the present invention were tested and found to bind to human αvβ3 integrin. These compounds were generally found to have $IC_{50}$ values less than about 100 nM in the SPA assay.

Representative compounds of the present invention were tested and generally found to inhibit ≧50% the attachment of αvβ5 expressing cells to plates coated with vitronectin at concentrations of about 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

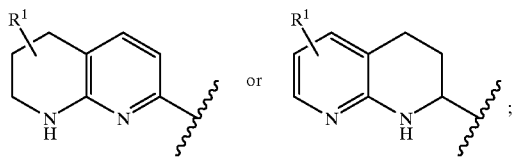

wherein X is selected from the group consisting of

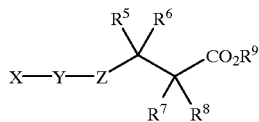

Y is selected from the group consisting of
—(CH$_2$)$_m$—,
—(CH$_2$)$_m$—O—(CH$_2$)$_n$—,
—(CH$_2$)$_m$—NR$^4$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH$_2$)$_m$—O—(CH$_2$)$_n$—O—(CH$_2$)$_p$—,
—(CH$_2$)$_m$—O—(CH$_2$)$_n$—NR$^4$—(CH$_2$)$_p$—,
—(CH$_2$)$_m$—NR$^4$—(CH$_2$)$_n$—NR$^4$—(CH$_2$)$_p$—,
—(CH$_2$)$_m$—O—(CH$_2$)$_n$—S—(CH$_2$)$_p$—,
—(CH$_2$)$_m$—S—(CH$_2$)$_n$—S—(CH$_2$)$_p$—,
—(CH$_2$)$_m$—NR$^4$—(CH$_2$)$_n$—S—(CH$_2$)$_p$—,
—(CH$_2$)$_m$—NR$^4$—(CH$_2$)$_n$—O—(CH$_2$)$_p$—,
—(CH$_2$)$_m$—S—(CH$_2$)$_n$—O—(CH$_2$)$_p$—, and
—(CH$_2$)$_m$—S—(CH$_2$)$_n$—NR$^4$—(CH$_2$)$_p$—,
wherein any methylene (CH$_2$) carbon atom in Y, other than in R$^4$, can be substituted by one or two R$^3$ substituents, with the proviso that when Y is —(CH$_2$)$_m$—NR$^4$—(CH$_2$)$_n$— and n=1, then the R$^3$ substituent on the methylene carbon in —(CH$_2$)$_m$— adjacent to the nitrogen cannot be oxo;

Z is selected from the group consisting of

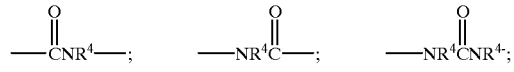

—CH$_2$CH$_2$—, and —CH=CH—, wherein either carbon atom can be substituted by one or two R$^3$ substituents;

R$^1$ and R$^2$ are each independently selected from the group consisting of
hydrogen, halogen, C$_{1-10}$ alkyl, C$_{3-8}$ cycloalkyl, C$_{3-8}$ cycloheteroalkyl, C$_{3-8}$ cycloalkyl C$_{1-6}$ alkyl, C$_{3-8}$ cycloheteroalkyl C$_{1-6}$ alkyl, aryl, aryl C$_{1-8}$ alkyl, amino, amino C$_{1-8}$ alkyl, C$_{1-3}$ acylamino, C$_{1-3}$ acylamino C$_{1-8}$ alkyl, (C$_{1-6}$ alkyl)$_p$amino, (C$_{1-6}$ alkyl)$_p$amino C$_{1-8}$ alkyl, C$_{1-4}$ alkoxy, C$_{1-4}$ alkoxy C$_{1-6}$ alkyl, hydroxycarbonyl, hydroxycarbonyl C$_{1-6}$ alkyl, C$_{1-3}$ alkoxycarbonyl, C$_{1-3}$ alkoxycarbonyl C$_{1-6}$ alkyl, hydroxycarbonyl-C$_{1-6}$ alkyloxy, hydroxy, hydroxy C$_{1-6}$ alkyl, C$_{1-6}$ alkyloxy-C$_{1-6}$ alkyl, nitro, cyano, trifluoromethyl, trifluoromethoxy, trifluoroethoxy, C$_{1-8}$ alkyl-S(O)$_p$, (C$_{1-8}$ alkyl)$_p$aminocarbonyl, C$_{1-8}$ alkyloxycarbonylamino, (C$_{1-8}$ alkyl)$_p$aminocarbonyloxy, (aryl C$_{1-8}$ alkyl)$_p$amino, (aryl)$_p$amino, aryl C$_{1-8}$ alkylsulfonylamino, and C$_{1-8}$ alkylsulfonylamino;

or two R$^1$ substituents, when on the same carbon atom, are taken together with the carbon atom to which they are attached to form a carbonyl group;

each R$^3$ is independently selected from the group consisting of
hydrogen,
aryl,
C$_{1-10}$ alkyl,
aryl-(CH$_2$)$_r$—O—(CH$_2$)$_s$—,
aryl-(CH$_2$)$_r$—S(O)$_p$—(CH$_2$)$_s$—,
aryl-(CH$_2$)$_r$—C(O)—(CH$_2$)$_s$—,
aryl-(CH$_2$)$_r$—C(O)—N(R$^4$)—(CH$_2$)$_s$—,
aryl-(CH$_2$)$_r$—N(R$^4$)—C(O)—(CH$_2$)$_s$—,
aryl-(CH$_2$)$_r$—N(R$^4$)—(CH$_2$)$_s$—,
halogen,
hydroxyl,
oxo,
trifluoromethyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
HC≡C—(CH$_2$)$_t$—,
C$_{1-6}$ alkyl-C≡C—(CH$_2$)$_t$—,
C$_{3-7}$ cycloalkyl-C≡C—(CH$_2$)$_t$—,
aryl-C≡C—(CH$_2$)$_t$—,
C$_{1-6}$ alkylaryl-C≡C—(CH$_2$)$_t$—,
CH$_2$=CH—(CH$_2$)$_t$—,
C$_{1-6}$ alkyl-CH=CH—(CH$_2$)$_t$—,
C$_{3-7}$ cycloalkyl-CH=CH—(CH$_2$)$_t$—,
aryl-CH=CH—(CH$_2$)$_t$—,
C$_{1-6}$ alkylaryl-CH=CH—(CH$_2$)$_t$—,
C$_{1-6}$ alkyl-SO$_2$—(CH$_2$)$_t$—,
C$_{1-6}$ alkylaryl-SO$_2$—(CH$_2$)$_t$—,
C$_{1-6}$ alkoxy,
aryl C$_{1-6}$ alkoxy,
aryl C$_{1-6}$ alkyl,
(C$_{1-6}$ alkyl)$_p$amino C$_{1-6}$ alkyl,
(aryl)$_p$amino, (aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;
or two R$^3$ substituents, when on the same carbon atom are taken together with the carbon atom to which they are attached to form a carbonyl group or a cyclopropyl group, wherein any of the alkyl groups of R$^3$ are either unsubstituted or substituted with one to three R$^1$ substituents, and provided that each R$^3$ is selected such that in the resultant compound the carbon atom or atoms to which R$^3$ is attached is itself attached to no more than one heteroatom;
each R$^4$ is independently selected from the group consisting of
hydrogen,
aryl,
aminocarbonyl,
C$_{3-8}$ cycloalkyl,
amino C$_{1-6}$ alkyl,
(aryl)$_p$aminocarbonyl,
(aryl C$_{1-5}$ alkyl)$_p$aminocarbonyl,
hydroxycarbonyl C$_{1-6}$ alkyl,
C$_{1-8}$ alkyl,
aryl C$_{1-6}$ alkyl,
(C$_{1-6}$ alkyl)$_p$amino C$_{2-6}$ alkyl,
(aryl C$_{1-6}$ alkyl)$_p$amino C$_{2-6}$ alkyl,
C$_{1-8}$ alkylsulfonyl,
C$_{1-8}$ alkoxycarbonyl,
aryloxycarbonyl,
aryl C$_{1-8}$ alkoxycarbonyl,
C$_{1-8}$ alkylcarbonyl,
arylcarbonyl,
aryl C$_{1-6}$ alkylcarbonyl,
(C$_{1-8}$ alkyl)$_p$aminocarbonyl,
aminosulfonyl,
C$_{1-8}$ alkylaminosulfonyl,
(aryl)$_p$aminosulfonyl,
(aryl C$_{1-8}$ alkyl)$_p$aminosulfonyl,
arylsulfonyl,
arylC1-6 alkylsulfonyl,
C$_{1-6}$ alkylthiocarbonyl,
arylthiocarbonyl, and
aryl C$_{1-6}$ alkylthiocarbonyl,
wherein any of the alkyl groups of R$^4$ are either unsubstituted or substituted with one to three R$^1$ substituents;
R$^5$ and R$^6$ are each independently selected from the group consisting of
hydrogen,
C$_{1-10}$ alkyl,
aryl,
aryl-(CH$_2$)$_r$—O—(CH$_2$)$_s$—,
aryl-(CH$_2$)$_r$—S(O)$_p$—(CH$_2$)$_s$—,
aryl-(CH$_2$)$_r$—C(O)—(CH$_2$)$_s$—,
aryl-(CH$_2$)$_r$—C(O)—N(R$^4$)—(CH$_2$)$_s$—,
aryl-(CH$_2$)$_r$—N(R$^4$)—C(O)—(CH$_2$)$_s$—,
aryl-(CH$_2$)$_r$—N(R$^4$)—(CH$_2$)$_s$—,
halogen,
hydroxyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino, amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC\equiv C-(CH_2)_t-$,
$C_{1-6}$ alkyl-$C\equiv C-(CH_2)_t-$,
$C_{3-7}$ cycloalkyl-$C\equiv C-(CH_2)_t-$,
aryl-$C\equiv C-(CH_2)_t-$,
$C_{1-6}$ alkylaryl-$C\equiv C-(CH_2)_t-$,
$CH_2=CH-(CH_2)_t-$,
$C_{1-6}$ alkyl-$CH=CH-(CH_2)_t-$,
$C_{3-7}$ cycloalkyl-$CH=CH-(CH_2)_t-$,
aryl-$CH=CH-(CH_2)_t-$,
$C_{1-6}$ alkylaryl-$CH=CH-(CH_2)_t-$,
$C_{1-6}$ alkyl-$SO_2-(CH_2)_t-$,
$C_{1-6}$ alkylaryl-$SO_2-(CH_2)_t-$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
$(aryl)_p$amino,
$(aryl)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
$(aryl)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
$(aryl)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
$(aryl)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or $R^5$ and $R^6$ are taken together with the carbon atom to which they are attached to form a carbonyl group, wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen,
$C_{1-10}$ alkyl,
aryl,
aryl-$(CH_2)_r-O-(CH_2)_s-$,
aryl-$(CH_2)_r-S(O)_p-(CH_2)_s-$,
aryl-$(CH_2)_r-C(O)-(CH_2)_s-$,
aryl-$(CH_2)_r-C(O)-N(R^4)-(CH_2)_s-$,
aryl-$(CH_2)_r-N(R^4)-C(O)-(CH_2)_s-$,
aryl-$(CH_2)_r-N(R^4)-(CH_2)_s-$,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC\equiv C-(CH_2)_t-$,
$C_{1-6}$ alkyl-$C\equiv C-(CH_2)_t-$, $C_{3-7}$ cycloalkyl-C≡C—(CH$_2$)$_t$—,
aryl-C≡C—(CH$_2$)$_t$—,
$C_{1-6}$ alkylaryl-C≡C—(CH$_2$)$_t$—,
CH$_2$=CH—(CH$_2$)$_t$—,
$C_{1-6}$ alkyl-CH=CH—(CH$_2$)$_t$—,
$C_{3-7}$ cycloalkyl-CH=CH—(CH$_2$)$_t$—,
aryl-CH=CH—(CH$_2$)$_t$—,
$C_{1-6}$ alkylaryl-CH=CH—(CH$_2$)$_t$—,
$C_{1-6}$ alkyl-SO$_2$—(CH$_2$)$_t$—,
$C_{1-6}$ alkylaryl-SO$_2$—(CH$_2$)$_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$ amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl,
(aryl $C_{1-8}$ alkyl)$_p$aminocarbonyl $C_{1-6}$ alkyl, and
$C_{7-20}$ polycyclyl $C_{0-8}$ alkylsulfonylamino,
wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and $R^8$ are attached is itself attached to no more than one heteroatom;
$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
wherein
each m is independently an integer from 0 to 6;
each n is independently an integer from 0 to 6;
each p is independently an integer from 0 to 2;
each r is independently an integer from 1 to 3;
each s is independently an integer from 0 to 3; and
each t is independently an integer from 0 to 3;
and the pharmaceutically acceptable salts thereof.

2. The compound of claim 1 wherein X is and $R^1$ is as defined in claim 1 above.

3. The compound of claim 1 wherein Y is selected from the group consisting of
—(CH$_2$)$_m$—,
—(CH$_2$)$_m$—O—(CH$_2$)$_n$—,
—(CH$_2$)$_m$—NR$^4$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH$_2$)$_m$—O—(CH$_2$)$_n$—O—(CH$_2$)$_p$—,
—(CH$_2$)$_m$—O—(CH$_2$)$_n$—NR$^4$—(CH$_2$)$_p$—,
—(CH$_2$)$_m$—NR$^4$—(CH$_2$)$_n$—NR$^4$—(CH$_2$)$_p$—, and
—(CH$_2$)$_m$—NR$^4$—(CH$_2$)$_n$—O—(CH$_2$)$_p$—, wherein any methylene (CH$_2$) carbon atom in Y, other than in R$^4$, can be substituted by one or two R$^3$ substituents, with the proviso that when Y is —(CH$_2$)$_m$—NR$^4$—(CH$_2$)$_n$— and n=1, then the R$^3$ substituent on the methylene carbon in —(CH$_2$)$_m$— adjacent to the nitrogen cannot be oxo; and Z is selected from the group consisting of

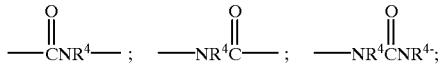

—CH$_2$CH$_2$—, and —CH=CH—, wherein either carbon atom can be substituted by one or two R$^3$ substituents.

4. The compound of claim 3 wherein Y is selected from the group consisting of

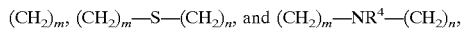

wherein any methylene (CH$_2$) carbon atom in Y, other than in R$^4$, can be substituted by one or two R$^3$ substituents, with the proviso that when Y is —(CH$_2$)$_m$—NR$^4$—(CH$_2$)$_n$— and n=1 then the R$^3$ substituent on the methylene carbon in —(CH$_2$)$_m$— adjacent to the nitrogen cannot be oxo; and Z is selected from the group consisting of

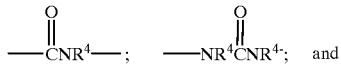

—CH$_2$CH$_2$—, wherein either carbon atom can be substituted by one or two R$^3$ substituents.

5. The compound of claim 4 wherein each R$^3$ is independently selected from the group consisting of
hydrogen,
fluoro,
trifluoromethyl,
aryl,
C$_{1-8}$ alkyl,
arylC$_{1-6}$ alkyl
hydroxyl,
oxo,
arylaminocarbonyl,
aryl C$_{1-5}$ alkylaminocarbonyl,
aminocarbonyl, and
aminocarbonyl C$_{1-6}$ alkyl;
and each R$^4$ is independently selected from the group consisting of
hydrogen,
aryl,
C$_{3-8}$ cycloalkyl,
C$_{1-8}$ alkyl,
C$_{1-8}$ alkylcarbonyl,
arylcarbonyl,
C$_{1-6}$ alkylsulfonyl,
arylsulfonyl,
arylC$_{1-6}$alkylsulfonyl,
arylC$_{1-6}$alkylcarbonyl,
C$_{1-8}$alkylaminocarbonyl,
arylC$_{1-5}$alkylaminocarbonyl,
arylC$_{1-8}$alkoxycarbonyl, and
C$_{1-8}$alkoxycarbonyl.

6. The compound of claim 5 wherein R$^6$, R$^7$, and R$^8$ are each hydrogen and R$^5$ is selected from the group consisting of
hydrogen,
aryl,
C$_{1-8}$ alkyl,
aryl-C≡C—(CH$_2$)$_t$—,
aryl C$_{1-6}$ alkyl,
CH$_2$=CH—(CH$_2$)$_t$—, and
HC≡C—(CH$_2$)$_t$—.

7. The compound of claim 6 wherein R$^9$ is selected from the group consisting of hydrogen, methyl, and ethyl.

8. The compound of claim 7 wherein R$^9$ is hydrogen.

9. The compound of claim 5 wherein R$^5$, R$^6$, and R$^8$ are each hydrogen and R$^7$ is selected from the group consisting of
hydrogen,
aryl,
C$_{1-8}$ alkylcarbonylamino,
C$_{1-8}$ alkylsulfonylamino,
arylcarbonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C1-6 alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
arylaminocarbonylamino,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl, and
C$_{7-20}$ polycyclyl C$_{0-8}$ alkylsulfonylamino.

10. The compound of claim 9 wherein $R^5$, $R^6$, and $R^8$ are each hydrogen and $R^7$ is selected from the group consisting of hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

11. The compound according to claim 10 wherein $R^9$ is selected from the group consisting of hydrogen, methyl, and ethyl.

12. The compound according to claim 11 wherein $R^9$ is hydrogen.

13. The compound of claim 5 selected from the group consisting of:

3-(5-(5,6,7,8-Tetrahydro[1,8]naphthyridin-2-yl)-pentanoylamino)-propionic acid;

3(S)-(Pyridin-3-yl)-3-(5-(5,6,7,8-tetrahydro[1,8]naphthyridin-2-yl)-pentanoylamino)-propionic acid;

3(S)-(5,6,7,8-Tetrahydroquinolin-3-yl)-3-(5-(5,6,7,8-tetrahydro[1,8]naphthyridin-2-yl)-pentanoylamino)-propionic acid (trifluoroacetate);

2(S)-Benzenesulfonylamino-3-(5-(5,6,7,8-tetrahydro-[1,8]naphthyridin-2-yl)-pentanoylamino)-propionic acid trifluoroacetate;

3(S)-(Quinolin-3-yl)-3-(5-(5,6,7,8-tetrahydro-[1,8]naphthyridin-2-yl)-pentanoylamino)-propionic acid;

3(R)-(Quinolin-3-yl)-3-(5-(5,6,7,8-tetrahydro-[1,8]naphthyridin-2-yl)-pentanoylamino)-propionic acid;

3-(Quinolin-3-yl)-3-(7-(5,6,7,8-tetrahydro-[1,8]naphthyridin-2-yl)-heptanoylamino)-propionic acid bis(trifluoroacetate);

3-(Quinolin-3-yl)-3-(6-(5,6,7,8-tetrahydro-[1,8]naphthyridin-2-yl)-hexanoylamino)-propionic acid;

3(S)-(3-Fluorophenyl)-3-(4-(5,6,7,8-tetrahydro-[1,8]naphthyridin-2-ylamino)-butyrylamino)-propionic acid bis(trifluoroacetate);

3(S)-(5-(5,6,7,8-Tetrahydro-[1,8]naphthyridin-2-yl)-pentanoylamino)-pent4-enoic acid;

3(S)-(3-Fluorophenyl)-3-(5-(5,6,7,8-tetrahydro-[1,8]naphthyridin-2-yl)-pentanoylamino)-propionic acid;

2-(3-Fluorophenyl)-3-(5-(5,6,7,8-tetrahydro-[1,8]naphthyridin-2-yl)-pentanoylamino)-propionic acid trifluoroacetate salt;

3(S)-(Benzo[1,3]dioxol-5-yl)-3-(5-(5,6,7,8-tetrahydro-[1,8]naphthyridin-2-yl)-pentanoylamino)-propionic acid;

3(S)-(2,3-Dihydro-benzofuran-6-yl)-3-(5-(5,6,7,8-tetrahydro-[1,8]naphthyridin-2-yl)-pentanoylamino)-propionic acid;

3(S)-(2-Oxo-2,3-dihydro-benzoxazol-6-yl)-3-(5-(5,6,7,8-tetrahydro-[1,8]naphthyridin-2-yl)-pentanoylamino)-propionic acid trifluoroacetate;

3(S)-(3-Fluorophenyl)-3-{3-[(5,6,7,8-tetrahydro-[1,8]naphthyridin-2-ylmethyl)-amino]-propionylamino}-propionic acid;

3(S)-(3-Fluorophenyl)-3-(2-{propyl-[2-(5,6,7,8-tetrahydro-[1,8]naphthyridin-2-yl)-ethyl]-amino}-acetylamino)-propionic acid trifluoroacetate;

3(S)-(3-Fluorophenyl)-3-(2-{phenethyl-[2-(5,6,7,8-tetrahydro-[1,8]naphthyridin-2-yl)-ethyl]-amino}-acetylamino)-propionic acid trifluoroacetate;

3(S)-(3-Fluorophenyl)-3-{3(S)-[(5,6,7,8-tetrahydro-[1,8]naphthyridin-2-ylmethyl)-amino]-pent-4-ynoylamino}-propionic acid;

3(S)-(3-Fluorophenyl)-3-{3(S)-(3-fluorophenyl)-3-[(5,6,7,8-tetrahydro-[1,8]naphthyridin-2-ylmethyl)-amino]-propionylamino}-propionic acid bis(trifluoroacetate);

3(S)-(3-Fluoro-4-phenyl-phenyl)-3-(5-(5,6,7,8-tetrahydro-[1,8]naphthyridin-2-yl)-pentanoylamino)-propionic acid trifluoroacetate;

2(S)-(2-Thienylsulfonylamino)-3-(5-(5,6,7,8-tetrahydro-[1,8]naphthyridin-2-yl)-pentanoylamino)-propionic acid trifluoroacetate;

3(S)-(3-Fluorophenyl)-3-{3-methyl-3-[(5,6,7,8-tetrahydro-[1,8]naphthyridin-2-ylmethyl)-amino]-propionylamino}-propionic acid;

3(S)-(3-Fluorophenyl)-3-{2-[2-(5,6,7,8-tetrahydro-[1,8]naphthyridin-2-yl)-ethylamino]-acetylamino}-propionic acid;

3(S)-(3-Fluorophenyl)-3-{[3-(5,6,7,8-tetrahydro-[1,8]naphthyridin-2-yl)-propyl]-ureido}-propionic acid;

2(S)-(Methanesulfonylamino)-3-(5-(5,6,7,8-tetrahydro-[1,8]naphthyridin-2-yl)-pentanoylamino)-propionic acid;

3(S)-(2,3-Dihydro-benzofuran-6-yl)-3-[3-(5,6,7,8-tetrahydro-[1,8-naphthyridin-2-ylmethylsulfanyl)propionylamino]-propionic acid bis(trifluoroacetate);

3-(Quinolin-3-yl)-7-[(5,6,7,8-tetrahydro-[1,8]-naphthyridin-2-ylmethyl)amino]-heptanoic acid;

3-(Quinolin-3-yl)-7-[acetyl-(5,6,7,8-tetrahydro-[1,8]-naphthyridin-2-ylmethyl)amino]-heptanoic acid;

3-(Quinolin-3-yl)-7-[methanesulfonyl-(5,6,7,8-tetrahydro-[1,8]-naphthyridin-2-ylmethyl)amino]-heptanoic acid;

9-(5,6,7,8-Tetrahydro-[1,8]-naphthyridin-2-yl)-nonanoic acid;

2-(Benzenesulfonylamino)-9-(5,6,7,8-tetrahydro-[1,8]-naphthyridin-2-yl)-non-4-enoic acid bis(trifluoroacetate);

2(S)-(Benzenesulfonylamino)-9-(5,6,7,8-tetrahydro-[1,8]naphthyridin-2-yl)-nonanoic acid;

2(R)-(Benzenesulfonylamino)-9-(5,6,7,8-tetrahydro-[1,8]naphthyridin-2-yl)-nonanoic acid;

2(S)-(Benzenesulfonylamino)-10-(5,6,7,8-tetrahydro-[1,8]naphthyridin-2-yl)-decanoic acid;

2(S)-(Benzenesulfonylamino)-8-(5,6,7,8-tetrahydro-[1,8]naphthyridin-2-yl)-octanoic acid;

2(S)-(Cyclohexylmethanesulfonylamino)-9-(5,6,7,8-tetrahydro-[1,8naphthyridin-2-yl)-nonanoic acid hydrochloride;

2(S)-(7,7-Dimethyl-2-oxo-bicyclo[2.2.1]hept-1(S)-ylmethanesulfonylamino)-9-(5,6,7,8-tetrahydro-[1,8]naphthyridin-2-yl)-nonanoic acid hydrochloride;

2(S)-(Phenylmethanesulfonylamino)-9-(5,6,7,8-tetrahydro-[1,8]naphthyridin-2-yl)-nonanoic acid;

2(S)-(Cyclohexanesulfonylamino)-9-(5,6,7,8-tetrahydro-[1,8]naphthyridin-2-yl)-nonanoic acid hydrochloride;

2(S)-(Butane-1-sulfonylamino)-9-(5,6,7,8-tetrahydro-[1,8]naphthyridin-2-yl)-nonanoic acid hydrochloride;

2(S)-(3-Benzylureido)-9-(5,6,7,8-tetrahydro-[1,8]naphthyridin-2-yl)-nonanoic acid;

2(S)-(Benzyloxycarbonylamino)-9-(5,6,7,8-tetrahydro-[1,8]naphthyridin-2-yl)-nonanoic acid;

2(S)-(Phenylacetylamino)-9-(5,6,7,8-tetrahydro-[1,8]naphthyridin-2-yl)-nonanoic acid;

2(S)-(Acetylamino)-9-(5,6,7,8-tetrahydro-[1,8]naphthyridin-2-yl)-nonanoic acid;

2(S)-(Benzoylamino)-9-(5,6,7,8-tetrahydro-[1,8]naphthyridin-2-yl)-nonanoic acid;

3-(Quinolin-3-yl)-9-(5,6,7,8-tetrahydro-[1,8]-naphthyridin-2-yl)-nonanoic acid;

3(S)-(Quinolin-3-yl)-9-(5,6,7,8-tetrahydro-[1,8]-naphthyridin-2-yl)-nonanoic acid;

3(R)-(Quinolin-3-yl)-9-(5,6,7,8-tetrahydro-[1,8]-naphthyridin-2-yl)-nonanoic acid;

6-Oxo-3-(quinolin-3-yl)-9-(5,6,7,8-tetrahydro-[1,8]-naphthyridin-2-yl)-nonanoic acid;

3-(N-Oxo-quinolin-3-yl)-9-(5,6,7,8-tetrahydro-[1,8]-naphthyridin-2-yl)-nonanoic acid;

3-(Phenyl)-9-(5,6,7,8-tetrahydro-[1,8]-naphthyridin-2-yl)-nonanoic acid;

3-(Benzo[b]thiophen-2-yl)-9-(5,6,7,8-tetrahydro-[1,8]-naphthyridin-2-yl)-nonanoic acid;

3(R)-(Benzo[b]thiophen-2-yl)-9-(5,6,7,8-tetrahydro-[1,8]-naphthyridin-2-yl)-nonanoic acid;

3(S)-(Benzo[b]thiophen-2-yl)-9-(5,6,7,8-tetrahydro-[1,8]-naphthyridin-2-yl)-nonanoic acid;

3-(Pyridin-3-yl)-9-(5,6,7,8-tetrahydro-[1,8]-naphthyridin-2-yl)-nonanoic acid;

3(R)-(Pyridin-3-yl)-9-(5,6,7,8-tetrahydro-[1,8]-naphthyridin-2-yl)-nonanoic acid;

3(S)-(Pyridin-3-yl)-9-(5,6,7,8-tetrahydro-[1,8]-naphthyridin-2-yl)-nonanoic acid;

3-(3-Fluorophenyl)-9-(5,6,7,8-tetrahydro-[1,8]-naphthyridin-2-yl)-nonanoic acid;

3(R)-(3-Fluorophenyl)-9-(5,6,7,8-tetrahydro-[1,8]-naphthyridin-2-yl)-nonanoic acid;

3(S)-(3-Fluorophenyl)-9-(5,6,7,8-tetrahydro-[1,8]-naphthyridin-2-yl)-nonanoic acid;

3-(2,3-Dihydro-benzofuran-6-yl)-9-(5,6,7,8-tetrahydro-[1,8]-naphthyridin-2-yl)-nonanoic acid;

3(S)-(2,3-Dihydro-benzofuran-6-yl)-9-(5,6,7,8-tetrahydro-[1,8]-naphthyridin-2-yl)-nonanoic acid;

3(R)-(2,3-Dihydro-benzofuran-6-yl)-9-(5,6,7,8-tetrahydro-[1,8]-naphthyridin-2-yl)-nonanoic acid;

3-(2,3-Dihydro-benzofuran-6-yl)-9-(5,6,7,8-tetrahydro-[1,8]-naphthyridin-2-yl)-non-4-enoic acid trifluoroacetate;

3-(2,3-Dihydro-furo[3,2-b]pyridin-5-yl)-9-(5,6,7,8-tetrahydro-[1,8]naphthyridin-2-yl)-nonanoic acid;

3(R)-(2,3-Dihydro-furo[3,2-b]pyridin-5-yl)-9-(5,6,7,8-tetrahydro-[1,8]naphthyridin-2-yl)-nonanoic acid;

3(S)-(2,3-Dihydro-furo[3,2-b]pyridin-5-yl)-9-(5,6,7,8-tetrahydro-[1,8]naphthyridin-2-yl)-nonanoic acid;

3-(Furo[2,3b]pyridin-5-yl)-9-(5,6,7,8-tetrahydro-[1,8]naphthyridin-2-yl)-nonanoic acid;

3(R)-(Furo[2,3b]pyridin-5-yl)-9-(5,6,7,8-tetrahydro-[1,8]naphthyridin-2-yl)-nonanoic acid;

3(S)-(Furo[2,3b]pyridin-5-yl)-9-(5,6,7,8-tetrahydro-[1,8]naphthyridin-2-yl)-nonanoic acid;

3-(2,3-Dihydro-furo[2,3-b]pyridin-5-yl)-9-(5,6,7,8-tetrahydro-[1,8]naphthyridin-2-yl)-nonanoic acid;

3(R)-(2,3-Dihydro-furo[2,3-b]pyridin-5-yl)-9-(5,6,7,8-tetrahydro-[1,8]naphthyridin-2-yl)-nonanoic acid;

3(S)-(2,3-Dihydro-furo[2,3-b]pyridin-5-yl)-9-(5,6,7,8-tetrahydro-[1,8]naphthyridin-2-yl)-nonanoic acid;

3-(6-Methoxy-pyridin-3-yl)-9-(5,6,7,8-tetrahydro-[1,8]-naphthyridin-2-yl)-nonanoic acid;

3(S)-(6-Methoxy-pyridin-3-yl)-9-(5,6,7,8-tetrahydro-[1,8]-naphthyridin-2-yl)-nonanoic acid;

3(R)-(6-Methoxy-pyridin-3-yl)-9-(5,6,7,8-tetrahydro-[1,8]-naphthyridin-2-yl)-nonanoic acid;

3-(Pyrimidin-5-yl)-9-(5,6,7,8-tetrahydro-[1,8]-naphthyridin-2-yl)-nonanoic acid;

3(R)-(Pyrimidin-5-yl)-9-(5,6,7,8-tetrahydro-[1,8]-naphthyridin-2-yl)-nonanoic acid;

3(S)-(Pyrimidin-5-yl)-9-(5,6,7,8-tetrahydro-[1,8]-naphthyridin-2-yl)-nonanoic acid;

3-(6-Amino-pyridin-3-yl)-9-(5,6,7,8-tetrahydro-[1,8]-naphthyridin-2-yl)-nonanoic acid;

3(R)-(6-Amino-pyridin-3-yl)-9-(5,6,7,8-tetrahydro-[1,8]-naphthyridin-2-yl)-nonanoic acid;

3(S)-(6-Amino-pyridin-3-yl)-9-(5,6,7,8-tetrahydro-[1,8]-naphthyridin-2-yl)-nonanoic acid;

3-(Benzo[b]thiazol-2-yl)-9-(5,6,7,8-tetrahydro-[1,8]-naphthyridin-2-yl)-nonanoic acid hydrochloride;

3(R)-(Benzo[b]thiazol-2-yl)-9-(5,6,7,8-tetrahydro-[1,8]-naphthyridin-2-yl)-nonanoic acid hydrochloride;

3(S)-(Benzo[b]thiazol-2-yl)-9-(5,6,7,8-tetrahydro-[1,8]-naphthyridin-2-yl)-nonanoic acid hydrochloride;

3-(6-Oxo-1,6-dihydro-pyridin-3-yl)-9-(5,6,7,8-tetrahydro-[1,8]-naphthyridin-2-yl)-nonanoic acid bis-(trifluoroacetate);

3-(6-Methoxy-pyridin-3-yl)-5-oxo-9-(5,6,7,8-tetrahydro-[1,8]-naphthyridin-2-yl)-nonanoic acid;

3(R)-(6-Methoxy-pyridin-3-yl)-5-oxo-9-(5,6,7,8-tetrahydro-[1,8]-naphthyridin-2-yl)-nonanoic acid;

3(S)-(6-Methoxy-pyridin-3-yl)-5-oxo-9-(5,6,7,8-tetrahydro-[1,8]-naphthyridin-2-yl)-nonanoic acid;

3-(2-Methyl-pyrimidin-5-yl)-9-(5,6,7,8-tetrahydro-[1,8]-naphthyridin-2-yl)-nonanoic acid;

3(R)-(2-Methyl-pyrimidin-5-yl)-9-(5,6,7,8-tetrahydro-[1,8]-naphthyridin-2-yl)-nonanoic acid;

3(S)-(2-Methyl-pyrimidin-5-yl)-9-(5,6,7,8-tetrahydro-[1,8]-naphthyridin-2-yl)-nonanoic acid;

3-(2-Methoxy-pyrimidin-5-yl)-9-(5,6,7,8-tetrahydro-[1,8]-naphthyridin-2-yl)-nonanoic acid;

3(R)-(2-Methoxy-pyrimidin-5-yl)-9-(5,6,7,8-tetrahydro-[1,8]-naphthyridin-2-yl)-nonanoic acid;

3(S)-(2-Methoxy-pyrimidin-5-yl)-9-(5,6,7,8-tetrahydro-[1,8]-naphthyridin-2-yl)-nonanoic acid;

3-(6-Methoxy-pyridin-3-yl)-5-hydroxy-9-(5,6,7,8-tetrahydro-[1,8]-naphthyridin-2-yl)-nonanoic acid;

3(R)-(6-Methoxy-pyridin-3-yl)-5-hydroxy-9-(5,6,7,8-tetrahydro-[1,8]-naphthyridin-2-yl)-nonanoic acid;

3(S)-(6-Methoxy-pyridin-3-yl)-5-hydroxy-9-(5,6,7,8-tetrahydro-[1,8]-naphthyridin-2-yl)-nonanoic acid;

3-(6-Methoxy-pyridin-3-yl)-7-oxo-9-(5,6,7,8-tetrahydro-[1,8]-naphthyridin-2-yl)-nonanoic acid;

3(R)-(6-Methoxy-pyridin-3-yl)-7-oxo-9-(5,6,7,8-tetrahydro-[1,8]-naphthyridin-2-yl)-nonanoic acid;

3(S)-(6-Methoxy-pyridin-3-yl)-7-oxo-9-(5,6,7,8-tetrahydro-[1,8]-naphthyridin-2-yl)-nonanoic acid;

3-(6-Methoxy-pyridin-3-yl)-7-hydroxy-9-(5,6,7,8-tetrahydro-[1,8]-naphthyridin-2-yl)-nonanoic acid;

3(R)-(6-Methoxy-pyridin-3-yl)-7-hydroxy-9-(5,6,7,8-tetrahydro-[1,8]-naphthyridin-2-yl)-nonanoic acid;

3(S)-(6-Methoxy-pyridin-3-yl)-7-hydroxy-9-(5,6,7,8-tetrahydro-[1,8]-naphthyridin-2-yl)-nonanoic acid;

and the pharmaceutically acceptable salts thereof.

14. The compound of claim 13 selected from the group consisting of:

3(S)-(Pyridin-3-yl)-3-(5-(5,6,7,8-tetrahydro-[1,8] naphthyridin-2-yl)-pentanoylamino)-propionic acid;

2(S)-Benzenesulfonylamino-3-(5-(5,6,7,8-tetrahydro-[1,8]naphthyridin-2-yl)-pentanoylamino)-propionic acid trifluoroacetate;

3(S)-(Quinolin-3-yl)-3-(5-(5,6,7,8-tetrahydro-[1,8] naphthyridin-2-yl)-pentanoylamino)-propionic acid;

3(R)-(Quinolin-3-yl)-3-(5-(5,6,7,8-tetrahydro-[1,8] naphthyridin-2-yl)-pentanoylamino)-propionic acid;

2(S)-(2-Thienylsulfonylamino)-3-(5-(5,6,7,8-tetrahydro-[1,8]naphthyridin-2-yl)-pentanoylamino)-propionic acid trifluoroacetate;

2-(Benzenesulfonylamino)-9-(5,6,7,8-tetrahydro-[1,8]-naphthyridin-2-yl)-non4-enoic acid bis (trifluoroacetate);

and the pharmaceutically acceptable salts thereof.

15. The compound of claim 13 selected from the group consisting of:

3(R)-(Quinolin-3-yl)-9-(5,6,7,8-tetrahydro-[1,8]-naphthyridin-2-yl)-nonanoic acid;

3(S)-(Quinolin-3-yl)-9-(5,6,7,8-tetrahydro-[1,8]-naphthyridin-2-yl)-nonanoic acid;

3(R)-(Benzo[b]thiophen-2-yl)-9-(5,6,7,8-tetrahydro-[1,8]-naphthyridin-2-yl)-nonanoic acid;

3(S)-(Benzo[b]thiophen-2-yl)-9-(5,6,7,8-tetrahydro-[1,8]-naphthyridin-2-yl)-nonanoic acid;

3(R)-(Pyridin-3-yl)-9-(5,6,7,8-tetrahydro-[1,8]-naphthyridin-2-yl)-nonanoic acid;

3(S)-(Pyridin-3-yl)-9-(5,6,7,8-tetrahydro-[1,8]-naphthyridin-2-yl)-nonanoic acid;

3(R)-(3-Fluorophenyl)-9-(5,6,7,8-tetrahydro-[1,8]-naphthyridin-2-yl)-nonanoic acid;

3(S)-(3-Fluorophenyl)-9-(5,6,7,8-tetrahydro-[1,8]-naphthyridin-2-yl)-nonanoic acid;

3(R)-(2,3-Dihydro-benzofuran-6-yl)-9-(5,6,7,8-tetrahydro-[1,8]-naphthyridin-2-yl)-nonanoic acid;

3(S)-(2,3-Dihydro-benzofuran-6-yl)-9-(5,6,7,8-tetrahydro-[1,8]-naphthyridin-2-yl)-nonanoic acid;

3(R)-(2,3-Dihydro-furo[3,2-b]pyridin-5-yl)-9-(5,6,7,8-tetrahydro-[1,8] naphthyridin-2-yl)-nonanoic acid;

3(S)-(2,3-Dihydro-furo[3,2-b]pyridin-5-yl)-9-(5,6,7,8-tetrahydro-[1,8] naphthyridin-2-yl)-nonanoic acid;

3(R)-(Furo[2,3b]pyridin-5-yl)-9-(5,6,7,8-tetrahydro-[1,8] naphthyridin-2-yl)-nonanoic acid;

3(S)-(Furo[2,3b]pyridin-5-yl)-9-(5,6,7,8-tetrahydro-[1,8] naphthyridin-2-yl)-nonanoic acid;

3(R)-(2,3-Dihydro-furo[2,3-b]pyridin-5-yl)-9-(5,6,7,8-tetrahydro-[1,8] naphthyridin-2-yl)-nonanoic acid;

3(S)-(2,3-Dihydro-furo[2,3-b]pyridin-5-yl)-9-(5,6,7,8-tetrahydro-[1,8]naphthyridin-2-yl)-nonanoic acid;

3(R)-(6-Methoxy-pyridin-3-yl)-9-(5,6,7,8-tetrahydro-[1,8]-naphthyridin-2-yl)-nonanoic acid;

3(S)-(6-Methoxy-pyridin-3-yl)-9-(5,6,7,8-tetrahydro-[1,8]-naphthyridin-2-yl)-nonanoic acid;

3(R)-(6-Methoxy-pyridin-3-yl)-5-oxo-9-(5,6,7,8-tetrahydro-[1,8]-naphthyridin-2-yl)-nonanoic acid;

3(S)-(6-Methoxy-pyridin-3-yl)-5-oxo-9-(5,6,7,8-tetrahydro-[1,8]-naphthyridin-2-yl)-nonanoic acid;

3(R)-(6-Methoxy-pyridin-3-yl)-5-hydroxy-9-(5,6,7,8-tetrahydro-[1,8]-naphthyridin-2-yl)-nonanoic acid;

3(S)-(6-Methoxy-pyridin-3-yl)-5-hydroxy-9-(5,6,7,8-tetrahydro-[1,8]-naphthyridin-2-yl)-nonanoic acid;

3(R)-(6-Methoxy-pyridin-3-yl)-7-oxo-9-(5,6,7,8-tetrahydro-[1,8]-naphthyridin-2-yl)-nonanoic acid;

3(S)-(6-Methoxy-pyridin-3-yl)-7-oxo-9-(5,6,7,8-tetrahydro-[1,8]-naphthyridin-2-yl)-nonanoic acid;

3(R)-(6-Methoxy-pyridin-3-yl)-7-hydroxy-9-(5,6,7,8-tetrahydro-1,8]-naphthyridin-2-yl)-nonanoic acid;

3(S)-(6-Methoxy-pyridin-3-yl)-7-hydroxy-9-(5,6,7,8-tetrahydro-[1,8]-naphthyridin-2-yl)-nonanoic acid;

3(R)-(Pyrimidin-5-yl)-9-(5,6,7,8-tetrahydro-[1,8]-naphthyridin-2-yl)-nonanoic acid;

3(S)-(Pyrimidin-5-yl)-9-(5,6,7,8-tetrahydro-[1,8]-naphthyridin-2-yl)-nonanoic acid;

3(R)-(2-Methyl-pyrimidin-5-yl)-9-(5,6,7,8-tetrahydro-[1,8]-naphthyridin-2-yl)-nonanoic acid;

3(S)-(2-Methyl-pyrimidin-5-yl)-9-(5,6,7,8-tetrahydro-[1,8]-naphthyridin-2-yl)-nonanoic acid;

3(R)-(2-Methoxy-pyrimidin-5-yl)-9-(5,6,7,8-tetrahydro-[1,8]-naphthyridin-2-yl)-nonanoic acid;

3(S)-(2-Methoxy-pyrimidin-5-yl)-9-(5,6,7,8-tetrahydro-[1,8]-naphthyridin-2-yl)-nonanoic acid;

3(R)-(6-Amino-pyridin-3-yl)-9-(5,6,7,8-tetrahydro-[1,8]-naphthyridin-2-yl)-nonanoic acid;

3(S)-(6-Amino-pyridin-3-yl)-9-(5,6,7,8-tetrahydro-[1,8]-naphthyridin-2-yl)-nonanoic acid;

3(R)-(Benzo[b]thiazol-2-yl)-9-(5,6,7,8-tetrahydro-[1,8]-naphthyridin-2-yl)-nonanoic acid hydrochloride;

3(S)-(Benzo[b]thiazol-2-yl)-9-(5,6,7,8-tetrahydro-[1,8]-naphthyridin-2-yl)-nonanoic acid hydrochloride;

and the pharmaceutically acceptable salts thereof.

16. The compound of claim 15 selected from the group consisting of:

3(S)-(2-Methoxy-pyrimidin-5-yl)-9-(5,6,7,8-tetrahydro-[1,8]-naphthyridin-2-yl)-nonanoic acid;

3(R)-(2-Methoxy-pyrimidin-5-yl)-9-(5,6,7,8-tetrahydro-[1,8]-naphthyridin-2-yl)-nonanoic acid;

3(S)-(Pyrimidin-5-yl)-9-(5,6,7,8-tetrahydro-[1,8]-naphthyridin-2-yl)-nonanoic acid;

3(R)-(Pyrimidin-5-yl)-9-(5,6,7,8-tetrahydro-[1,8]-naphthyridin-2-yl)-nonanoic acid;

3(S)-(2-Methyl-pyrimidin-5-yl)-9-(5,6,7,8-tetrahydro-[1,8]-naphthyridin-2-yl)-nonanoic acid;

3(R)-(2-Methyl-pyrimidin-5-yl)-9-(5,6,7,8-tetrahydro-[1,8]-naphthyridin-2-yl)-nonanoic acid;

3(S)-(6-Methoxy-pyridin-3-yl)-7-oxo-9-(5,6,7,8-tetrahydro-[1,8]-naphthyridin-2-yl)-nonanoic acid;

3(R)-(6-Methoxy-pyridin-3-yl)-7-hydroxy-9-(5,6,7,8-tetrahydro-[1,8]-naphthyridin-2-yl)-nonanoic acid;

or a pharmaceutically acceptable salt thereof.

17. The compound of claim 16 which is

3(R)-(2-Methoxy-pyrimidin-5-yl)-9-(5,6,7,8-tetrahydro-[1,8]-naphthyridin-2-yl)-nonanoic acid;

or a pharmaceutically acceptable salt thereof.

18. The compound of claim 16 which is
3(R)-(Pyrimidin-5-yl)-9-(5,6,7,8-tetrahydro-[1,8]-naphthyridin-2-yl)-nonanoic acid;
or a pharmaceutically acceptable salt thereof.

19. The compound of claim 16 which is
3(R)-(2-Methyl-pyrimidin-5-yl)-9-(5,6,7,8-tetrahydro-[1,8]-naphthyridin-2-yl)-nonanoic acid;
or a pharmaceutically acceptable salt thereof.

20. The compound of claim 16 which is
3(S)-(2-Methoxy-pyrimidin-5-yl)-9-(5,6,7,8-tetrahydro-[1,8]-naphthyridin-2-yl)-nonanoic acid;
or a pharmaceutically acceptable salt thereof.

21. The compound of claim 1 which is
3(S)-(Pyrimidin-5-yl)-9-(5,6,7,8-tetrahydro-[1,8]-naphthyridin-2-yl)-nonanoic acid;
or a pharmaceutically acceptable salt thereof.

22. The compound of claim 1 which is
3(S)-(2-Methyl-pyrimidin-5-yl)-9-(5,6,7,8-tetrahydro-[1,8]-naphthyridin-2-yl)-nonanoic acid;
or a pharmaceutically acceptable salt thereof.

23. A pharmaceutical composition comprising a therapeutically effective amount of a compound of claim 1 and a pharmaceutically acceptable carrier.

24. A pharmaceutical composition made by combining a therapeutically effective amount of a compound of claim 1 and a pharmaceutically acceptable carrier.

25. A process for making a pharmaceutical composition comprising combining a therapeutically effective amount of a compound of claim 1 and a pharmaceutically acceptable carrier.

26. The composition of claim 13 which further comprises an active ingredient selected from the group consisting of
   a) an organic bisphosphonate or a pharmaceutically acceptable salt or ester thereof,
   b) an estrogen receptor modulator,
   c) a cytotoxic/antiproliferative agent,
   d) a matrix metalloproteinase inhibitor,
   e) an inhibitor of epidermal-derived, fibroblast-derived, or platelet-derived growth factors,
   f) an inhibitor of VEGF,
   g) an inhibitor of Flk-1/KDR, Flt-1, Tck/Tie-2, or Tie-1,
   h) a cathepsin K inhibitor, and
   i) a farnesyl transferase inhibitor or a geranylgeranyl transferase inhibitor or a dual farnesyl/geranylgeranyl transferase inhibitor;
and mixtures thereof.

27. The composition of claim 13 wherein said active ingredient is selected from the group consisting of
   a) an organic bisphosphonate or a pharmaceutically acceptable salt or ester thereof,
   b) an estrogen receptor modulator, and
   c) a cathepsin K inhibitor;
and mixtures thereof.

28. The composition of claim 27 wherein said organic bisphosphonate or pharmaceutically acceptable salt or ester thereof is alendronate monosodium trihydrate.

29. The composition of claim 26 wherein said active ingredient is selected from the group consisting of
   a) a cytotoxic/antiproliferative agent,
   b) a matrix metalloproteinase inhibitor,
   c) an inhibitor of epidermal-derived, fibroblast-derived, or platelet-derived growth factors,
   d) an inhibitor of VEGF,
   e) an inhibitor of Flk-1/KDR, Flt-1, Tck/Tie-2, or Tie-1, and
   f) a cathepsin K inhibitor;
and mixtures thereof.

30. A method of eliciting an integrin receptor antagonizing effect in a mammal in need thereof, comprising administering to the mammal a therapeutically effective amount of a compound according to claim 1.

31. The method of claim 30 wherein the integrin receptor antagonizing effect is an αvβ3 antagonizing effect.

32. The method of claim 31 wherein the αvβ3 antagonizing effect is selected from the group consisting of inhibition of bone resorption, restenosis, angiogenesis, diabetic retinopathy, macular degeneration, inflammation, viral disease, tumor growth, and metastasis.

33. The method of claim 32 wherein the αvβ3 antagonizing effect is the inhibition of bone resorption.

34. The method of claim 32 wherein the compound to be administered is
   3(S)-(2-Methoxy-pyrimidin-5-yl)-9-(5,6,7,8-tetrahydro-[1,8]-naphthyridin-2-yl)-nonanoic acid;
   3(S)-(Pyrimidin-5-yl)-9-(5,6,7,8-tetrahydro-[1,8]-naphthyridin-2-yl)-nonanoic acid; or
   3(S)-(2-Methyl-pyrimidin-5-yl)-9-(5,6,7,8-tetrahydro-[1,8]-naphthyridin-2-yl)-nonanoic acid;
or a pharmaceutically acceptable salt thereof.

35. The method of claim 30 wherein the integrin receptor antagonizing effect is an αvβ5 antagonizing effect.

36. The method of claim 35 wherein the αvβ5 antagonizing effect is selected from the group consisting of inhibition of restenosis, angiogenesis, diabetic retinopathy, macular degeneration, inflammation, tumor growth, and metastasis.

37. The method of claim 30 wherein the integrin receptor antagonizing effect is a dual αvβ3/αvβ5 antagonizing effect.

38. The method of claim 37 wherein the dual αvβ3/αvβ5 antagonizing effect is selected from the group consisting of inhibition of bone resorption, restenosis, angiogenesis, diabetic retinopathy, macular degeneration, inflammation, viral disease, tumor growth, and metastasis.

39. The method of claim 30 wherein the integrin receptor antagonizing effect is an αvβ6 antagonizing effect.

40. The method of claim 39 wherein the αvβ6 antagonizing effect is selected from the group consisting of angiogenesis, inflammatory response, and wound healing.

41. A method of eliciting an integrin receptor antagonizing effect in a mammal in need thereof, comprising administering to the mammal a therapeutically effective amount of the composition of claim 23.

42. A method of treating or preventing a condition mediated by antagonism of an integrin receptor in a mammal in need thereof, comprising administering to the mammal a therapeutically effective amount of the composition of claim 23.

43. A method of inhibiting bone resorption in a mammal in need thereof, comprising administering to the mammal a therapeutically effective amount of the composition of claim 23.

44. A method of inhibiting bone resorption in a mammal in need thereof, comprising administering to the mammal a therapeutically effective amount of the composition of claim 27.

45. A method of treating tumor growth in a mammal in need thereof, comprising administering to the mammal a therapeutically effective amount of the composition of claim 29.

46. A method of treating tumor growth in a mammal in need thereof, comprising administering to the mammal a therapeutically effective amount of a compound according to claim 1 in combination with radiation therapy.

47. The method of claim 46 wherein the compound to be administered is

3(S)-(2-Methoxy-pyrimidin-5-yl)-9-(5,6,7,8-tetrahydro-[1,8]-naphthyridin-2-yl)-nonanoic acid;

3(S)-(Pyrimidin-5-yl)-9-(5,6,7,8-tetrahydro-[1,8]-naphthyridin-2-yl)-nonanoic acid; or 3(S)-(2-Methyl-pyrimidin-5-yl)-9-(5,6,7,8-tetrahydro-[1,8]-naphthyridin-2-yl)-nonanoic acid;

or a pharmaceutically acceptable salt thereof.

* * * * *

UNITED STATES PATENT AND TRADEMARK OFFICE
CERTIFICATE OF CORRECTION

PATENT NO. : 6,048,861
DATED : 4/11/00
INVENTOR(S) : Ben C. Askew et al.

It is certified that error appears in the above-indentified patent and that said Letters Patent is hereby corrected as shown below:

IN THE CLAIMS:

Claims 21 and 22, Line 1 in each, cancel "1" and substitute therefor -- 16 --.

Claim 26, Line 1, cancel "13" and substitute therefor -- 23 --.

Claim 27, Line 1, cancel "13" and substitute therefor -- 26 --.

Signed and Sealed this

Twenty-seventh Day of March, 2001

Attest:

NICHOLAS P. GODICI

*Attesting Officer*    *Acting Director of the United States Patent and Trademark Office*